United States Patent
Achard et al.

(10) Patent No.: US 7,166,594 B2
(45) Date of Patent: Jan. 23, 2007

(54) STREPTOGRAMIN DERIVATIVES, THEIR PREPARATION AND COMPOSITIONS CONTAINING THEM

(75) Inventors: Daniel Achard, Thials (FR); Eric Bacque, Morsang sur Orge (FR); Jean-Claude Barriere, Bures sur Yvette (FR); Jean Bouquerel, Drancy (FR); Pascal Desmazeau, Tigery (FR); Serge Grisoni, Choisy le Roi (FR); Jean-Pierre Leconte, Brunoy (FR); Yves Ribeill, Raleigh, NC (US); Baptiste Ronan, Clamart (FR)

(73) Assignee: Aventis Pharma S.A., Antony Cedex (FR)

( * ) Notice: Subject to any disclaimer, the term of this patent is extended or adjusted under 35 U.S.C. 154(b) by 452 days.

(21) Appl. No.: 10/310,773

(22) Filed: Dec. 6, 2002

(65) Prior Publication Data

US 2003/0149004 A1 Aug. 7, 2003

Related U.S. Application Data

(62) Division of application No. 09/609,717, filed on Jun. 30, 2000, now Pat. No. 6,569,854.

(60) Provisional application No. 60/184,349, filed on Feb. 23, 2000.

(30) Foreign Application Priority Data

Jun. 30, 1999 (FR) .................................. 99 08375

(51) Int. Cl.
*A61K 31/535* (2006.01)
*A61K 31/655* (2006.01)
*A61K 31/42* (2006.01)

(52) U.S. Cl. .......................... 514/232.2; 514/2; 514/9; 514/151

(58) Field of Classification Search .................... None
See application file for complete search history.

(56) References Cited

U.S. PATENT DOCUMENTS 5,200,394 A 4/1993 Di Giambattista et al.
5,726,151 A * 3/1998 Anger et al. .................. 514/11

FOREIGN PATENT DOCUMENTS

WO WO 89/03843 5/1989
WO WO 99/05165 2/1999

OTHER PUBLICATIONS

U.S. Appl. No. 09/627,791, filed Jul. 27, 2000 (Eric Bacque et. al.); Amendment filed Nov. 30, 2001, which amends claims 1, 2, 3, 9, 10, 14, 16, 20, 22, 23, and 25.
U.S. Appl. No. 09/643,197, filed Aug. 22, 2000 (Pascal Desmazeau et. al.); preliminary amendment filed Jun. 21, 2001, cancels claims 1-17 and adds claims 18-34); amendment filed Mar. 11, 2002, which amends claims 18 and 31 in response to a restriction requirement).
U.S. Appl. No. 10/055,888, filed Jan. 28, 2002 (Eric Bacque et al.) (72 pages, including abstract and 16 claims).

* cited by examiner

*Primary Examiner*—B. Dell Chism
(74) *Attorney, Agent, or Firm*—Finnegan, Henderson, Farabow, Garrett & Dunner, L.L.P.

(57) ABSTRACT

Group A streptogramin derivatives of general formula (I) in which:

$R_1$ represents a halogen atom or an azido or thiocyanato radical, $R_2$ represents a hydrogen atom or a methyl or ethyl radical, $R_3$ represents a hydrogen atom, or the residue of an aliphatic, cycloaliphatic, aromatic, araliphatic, heterocyclic or heterocyclylaliphatic ester which may be substituted, and the bond --- represents a single bond (stereochemistry 27R) or a double bond, as well as its salts when they exist

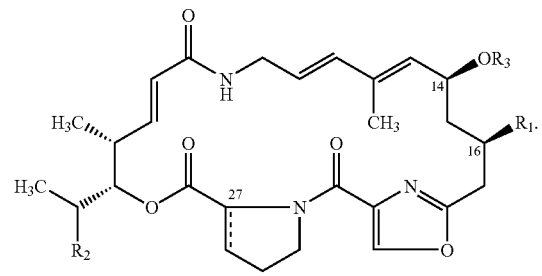

(I)

11 Claims, No Drawings

STREPTOGRAMIN DERIVATIVES, THEIR PREPARATION AND COMPOSITIONS CONTAINING THEM

This is a division of application Ser. No. 09/609,717, filed Jun. 30, 2000 now U.S. Pat. No. 6,569,854, which claims benefit of U.S. Provisional Application No. 60/184,349, filed Feb. 23, 2000, which is incorporated herein by reference. Under the provisions of 35 U.S.C. § 119, Applicants also claim the benefit of French Application No. 99/08375, Jun. 30, 1999, which is incorporated herein by reference.

The present invention relates to group A streptogramin derivatives of general formula:

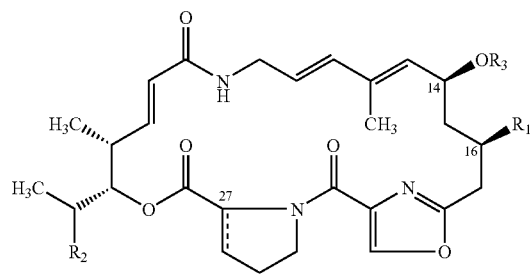

(I)

as well as their salts, which exhibit a particularly advantageous antibacterial activity.

Among the known streptogramins, pristinamycin (RP 7293), an antibacterial of natural origin produced by *Streptomyces pristinaespiralis* was first isolated in 1955. The pristinamycin marketed under the name Pyrostacine® consists mainly of pristinamycin IIA combined with pristinamycin IA.

Another antibacterial of the class of streptogramins: virginiamycin, has been prepared from *Streptomyces virginiae*, ATCC 13161 [Antibiotics and Chemotherapy, 5, 632 (1955)]. Virginiamycin (Staphylomycine®) consists mainly of factor $M_1$ combined with factor S (VS).

Semisynthetic derivatives of streptogramins of structure:

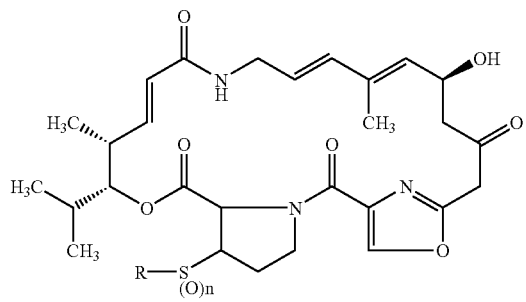

for which n is 0 to 2 have been described in patents EP 135410 and EP 191662. Combined with a semisynthetic component of group B streptogramins they manifest a synergistic action and can be used by the injection route.

In International Patent Application WO 99/05165, there have been described group A streptogramin derivatives of general formula:

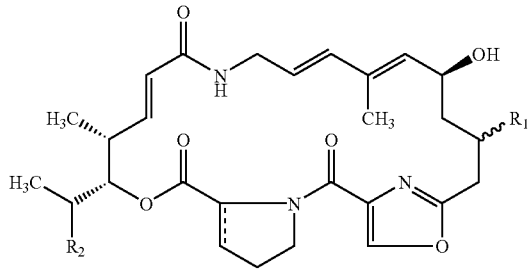

in which $R_1$ is a radical —NR'R" or —NR'OR'", $R_2$ is hydrogen, methyl or ethyl, and the bond --- is a single bond or a double bond, which are antimicrobial agents.

However, these derivatives do not achieve particularly high levels of activity and, moreover, do not always have a spectrum as broad as desired.

It has now been found that the group A streptogramin derivatives of general formula (I) in which:

$R_1$ represents a halogen atom or an azido or thiocyanato radical, $R_2$ represents a hydrogen atom or a methyl or ethyl radical, $R_3$ represents a hydrogen atom, or the residue of an aliphatic, cycloaliphatic, aromatic, araliphatic, heterocyclic or heterocyclylaliphatic ester which may be substituted, and the bond --- represents a single bond (stereochemistry 27R) or a double bond, and their salts when they exist, exhibit a particularly potent antibacterial activity, alone or combined with a group B streptogramin derivative, and/or also manifest a broadened spectrum compared with the usual spectrum for streptogramins.

According to the invention, when $R_1$ represents a halogen atom, it may be chosen from fluorine, chlorine, bromine or iodine;

when the radical $R_3$ represents the residue of an aliphatic, cycloaliphatic, aromatic, araliphatic, hydrocyclic or heterocyclylaliphatic ester which may be substituted, the latter may be chosen, by way of example, from $R'_3$—CO— radicals for which $R'_3$ is phenyl or phenylalkyl which are unsubstituted or which are substituted on the phenyl radical [with one or more radicals chosen from alkyl, optionally carrying a radical NR'R" in which the radicals R' and R", which are identical or different, may be hydrogen atoms or alkyl radicals which can form together with the nitrogen atom to which they are attached a 3- to 8-membered saturated or unsaturated heterocyclyl radical optionally comprising another heteroatom chosen from oxygen, sulfur or nitrogen, it being possible for the said heterocycle itself to be substituted with one or more radicals (alkyl, hydroxyalkyl, alkyloxyalkyl, alkyloxycarbonylalkyl, aryl, heterocyclyl, heterocyclylalkyl, which are saturated or unsaturated and have 3 to 8 members, or —CH$_2$—CO—NR'R"), or alternatively R' and/or R" may be a hydroxyalkyl radical, a phenyl radical, a 3- to 8-membered saturated or unsaturated heterocyclylalkyl radical, a radical —CO—NR'R" for which NR'R" is as defined above, or alkyl or acyl radicals which are substituted with NR'R" which is as defined above], or alternatively $R'_3$ may be chosen from phenyl or phenylalkyl radicals which are substituted on the phenyl radical with one or more radicals [chosen from alkyl, which may be substituted with an alkyloxy or alkylthio radical optionally carrying themselves a carboxyl radical or a radical NR'R" as defined above, or chosen from acyloxy which may be substituted with NR'R" as defined above], or alternatively R'$_3$ may be chosen from alkyl or cycloalkyl radicals which are optionally substituted; [with a carboxyl radical, a carboxyalkyldisulfanyl radical or with a radical NR'R", —CH$_2$—NR'R", or —CO—NR'R", or with an alkyloxycarbonyl, alkyloxy or alkyldi-sulfanyl radical which are optionally substituted with NR'R" or —CO—NR'R" for which NR'R" is as defined above], or alternatively R'$_3$ may be chosen from 3- to 8-membered-saturated or unsaturated heterocyclyl radicals which are optionally substituted [with alkyl or acyl which are themselves optionally substituted with NR'R"].

In general formula (I), unless otherwise stated, the alkyl or acyl radicals or portions are straight or branched and contain 1 to 12 carbon atoms, the heterocyclyl radicals may be chosen in particular from pyrrolidinyl, pyrrolyl, furyl, thienyl, imidazolyl, pyridyl, piperidinyl, piperazinyl, morpholinyl, thiomorpholinyl, pyrizanyl, pyrimidinyl, pyridazinyl and imidazolidinyl, and the aryl radicals may be chosen in particular from optionally substituted phenyl and more particularly from phenyl which is substituted with alkyl, alkyloxy or halogen, or with a radical —CH$_2$OH, —(CH$_2$)$_n$—NH$_2$, —(CH$_2$)$_n$—NHalkyl or —(CH$_2$)$_n$—N(alkyl)$_2$.

The streptogramin derivatives of general formula (I) may be prepared by halogenating, converting to an azide or converting to a thiocyanate, a streptogramin derivative of general formula:

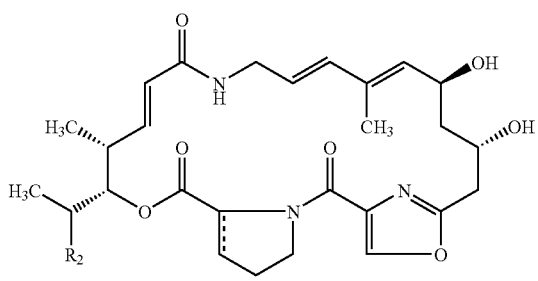

(II)

in which R$_2$ is as defined above, the bond --- represents a single bond (stereochemistry 27R) or a double bond, and in which the hydroxyl function at the 14-position has been previously protected, followed by the removal of the protecting radical and where appropriate, in order to obtain a derivative of general formula (I) for which R$_3$ is other than a hydrogen atom, introduction of the aliphatic, cycloaliphatic, aromatic, araliphatic, heterocyclic or heterocyclylaliphatic ester residue which may be substituted (R$_3$) according to the usual methods which do not alter the rest of the molecule.

The reactions for halogenating, converting to an azide or converting to a thiocyanate may be carried out in the presence of an aminosulfur trifluoride (for example diethylaminosulfur trifluoride, bis(2-methoxyethyl)aminosulfur trifluoride (Deoxofluor®), morpholinosulfur trifluoride) or alternatively in the presence of sulfur tetrafluoride, by means of a reagent such as a tetraalkylammonium, trialkylbenzylammonium or trialkylphenylammonium halide, azide or thiocyanate or by means of an alkali metal halide, azide or thiocyanate optionally supplemented with a crown ether. The fluorination reactions may also be carried out by the action of a fluorinating agent such as a sulfur fluoride [for example morpholinosulfur trifluoride, sulfur tetrafluoride (J. Org. Chem., 40, 3808 (1975)), diethylaminosulfur trifluoride (Tetrahedron, 44, 2875 (1988)), bis(2-methoxyethyl)aminosulfur trifluoride (Deoxofluor®). Alternatively, the fluorination reactions may also be carried out by means of a fluorinating agent such as hexafluoropropyldiethylamine (JP 2,039,546) or N-(2-chloro-1,1,2-trifluoroethyl)diethylamine.

While a tetraalkylammonium halide, azide or thiocyanate is used, the latter may be chosen, by way of example, from tetramethylammonium, tetraethylammonium, tetrapropylammonium, tetrabutylammonium (for example tetra-n-butylammonium), tetrapentylammonium, tetracyclohexylammonium, triethylmethylammonium, tributylmethylammonium or trimethylpropylammonium halides, azides or thiocyanates.

The procedure is carried out in an organic solvent such as a chlorinated solvent (for example dichloromethane, dichloroethane or chloroform) or in an ether (for example tetrahydrofuran) at a temperature of between −78 and 40° C. (preferably of between 0 and 30° C.). It is advantageous to carry out the procedure under argon or under nitrogen. It is understood that the use of the hydroxyl derivative of (16S) configuration leads to the derivative of (16R) configuration.

The protection and deprotection of the hydroxyl radical at the 14-position is carried out according to the usual methods which do not affect the rest of the molecule, in particular by application of the methods described by T. W. Greene and P. G. M. Wuts, Protective Groups in Organic Synthesis (2nd ed.), A. Wiley—Interscience Publication (1991), or by Mc Omie, Protective Groups in Organic Chemistry, Plenum Press (1973). For example, the procedure is carried out by protecting with a trialkylsilyl, alkyldiphenylsilyl (for example t-butyldiphenylsilyl and t-butyldimethylsilyl) or allyl radical which are introduced and removed as described below in the examples.

Where appropriate, when it is desired to prepare a product of general formula (I) for which R$_3$ is an aliphatic, cycloaliphatic, aromatic, araliphatic, heterocyclic or heterocyclylaliphatic ester which may be substituted, the subsequent esterification operation is carried out according to the usual methods which do not alter the rest of the molecule. More particularly, the esterification is carried out by the reaction of the acid or of a reactive derivative of the acid (for example acid chloride, reactive ester or anhydride), in the presence or otherwise of a coupling agent such as a carbodiimide (for example dicyclohexylcarbodiimide) and of a tertiary amine (trialkylamine such as triethylamine or diisopropylethylamine, or pyridine or a derivative) and optionally a catalyst such as 4-N-dimethylaminopyridine, at a temperature of between −40 and +80° C., in an organic solvent such as an amide (for example dimethylformamide or N-methyl-2-pyrrolidinone), pyridine, a halogenated solvent (for example dichloromethane, dichloroethane or chloroform) or an ether (tetrahydrofuran, dioxane or dimethoxyethane). It is understood that the functions which can interfere with the reaction are protected beforehand, and then released after the reaction.

The acid or the reactive acid derivative used is prepared as described below in the examples or by analogy with the methods described.

The dihydroxylated group A streptogramin derivative of general formula (II) may be obtained by selective reduction of the natural pristinamycin component of general formula:

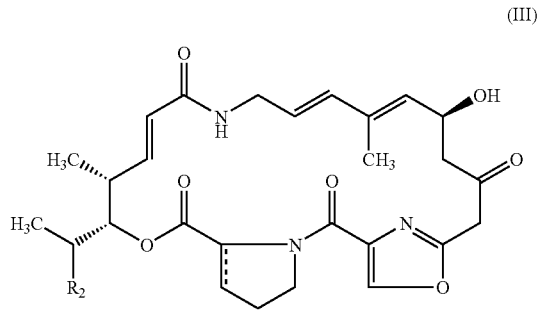

(III)

in which $R_2$ is as defined above and the bond ---represents a single bond (stereochemistry 27R) or a double bond, followed by the separation of the 16S epimer form.

The reduction is advantageously carried out in the presence of a reducing agent such as an alkali metal borohydride, for example sodium borohydride or sodium triacetoxyborohydride, in an organic solvent chosen from chlorinated solvents (for example dichloromethane, dichloroethane, chloroform), tetrahydrofuran, acetic acid and alcohols such as methanol, ethanol or 2-propanol, at a temperature of between −78 and 40° C.

The separation of the 16R epimer form and of the 16S epimer form is carried out according to the usual methods; for example, the separation of the epimer forms may be carried out by chromatography, flash chromatography, high-performance liquid chromatography (HPLC), on a chiral phase or otherwise, or centrifugal partition chromatography (CPC), from the mixture of the 16R and 16S epimers, or by crystallization.

In particular, (16S)-16-hydroxypristinamycin $II_A$ may be prepared according to F. Le Goffic et al.; Eur. J. Med.—Chimica Therapeutica; January-February, -16(1), 69–72 (1981).

The pristinamycin derivatives of general formula (III) correspond respectively to pristinamycin $II_A$ ($PII_A$), to pristinamycin $II_B$ ($PII_B$), to pristinamycin $II_C$ ($PII_C$), to pristinamycin $II_D$ ($PII_D$), to pristinamycin $II_F$ ($PII_F$), and to pristinamycin $II_G$ ($PII_G$), which are known components of natural pristinamycin. The components $PII_F$ and $PII_G$ have been described in European Patent EP 614910.

Pristinamycin $II_C$ ($PII_C$) and pristinamycin $II_D$ ($PII_D$) may be obtained as described by J. C. Barriére et al., Expert. Opin. Invest. Drugs, 3(2), 115–31 (1994).

The preparation and separation of the components of the natural group A streptogramins [streptogramins of general formula (III)] is carried out by fermentation a constituents from the fermentation: broth according to or by analogy with the method described by J. Preud'homme et al., Bull. Soc. Chim. Fr., vol. 2, 585 (1968) or in European Patent EP 614910. Alternatively, the preparation of the natural components of group A may be carried out by specific fermentation, as described in patent application FR 2,689,518.

The streptogramin derivatives of general formula (I) may be purified, where appropriate, by physical methods such as crystallization, chromatography or CPC.

Some of the streptogramin derivatives of general formula (I) may be converted to the state of addition salts with acids, by known methods. It is understood that these salts, when they exist, are also included within the scope of the present invention.

As examples of addition salts with pharmaceutically acceptable acids, there may be mentioned the salts formed with inorganic acids (hydrochlorides, hydrobromides, sulfates, nitrates, phosphates) or with organic acids (succinates, fumarates, tartrates, acetates, propionates, maleates, citrates, methanesulfonates, ethanesulfonates, phenyl-sulfonates, p-toluenesulfonates, isethionates, naphthylsulfonates or camphor-sulfonates, or with substitution derivatives of these compounds).

The streptogramin derivatives according to the present invention have antibacterial properties and properties synergizing the antibacterial activity of the group B streptogramin derivatives. They are particularly advantageous because of their potent activity, alone or combined.

When they are combined with a component or a derivative of the group B streptogramins, they may be chosen, depending on whether it is desired to obtain an orally or parenterally administrable form, from the natural components: pristinamycin $I_A$, pristinamycin $I_B$, pristinamycin $I_C$, pristinamycin $I_D$, pristinamycin $I_E$, pristinamycin $I_F$, pristinamycin $I_G$, virginiamycin $S_1$, $S_3$ or $S_4$, vernamycin B or C, etamycin or from the semisynthetic derivatives as described in patents or patent applications U.S. Pat. Nos. 4,618,599, 4,798,827, 5,326,782, EP 772630 or EP 770132, in particular the streptogramin derivatives of general formula:

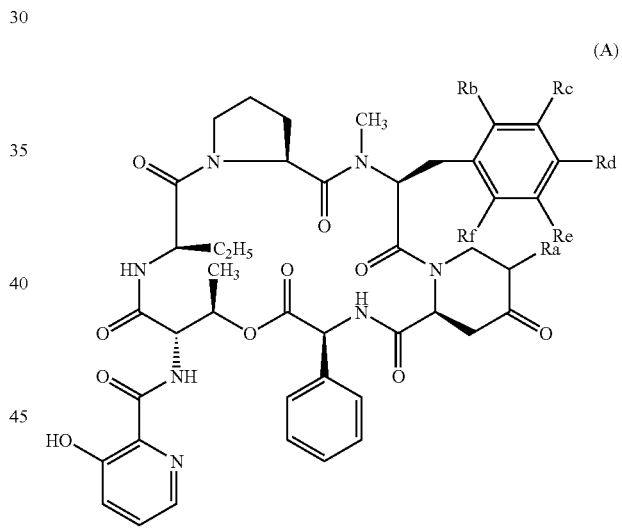

(A)

in which,

1. Rb, Rc, Re and Rf are hydrogen atoms, Rd is a hydrogen atom or a dimethylamino radical, and Ra is a radical of structure —CH$_2$R'a for which R'a is 3-pyrrolidinylthio or 3- or 4-piperidylthio which may be substituted with alkyl, or alkylthio substituted with 1 or 2 hydroxysulfonyl, alkylamino, dialkylamino (itself optionally substituted with mercapto or dialkylamino), or substituted with 1 or 2 optionally substituted piperazine rings, morpholino, thiomorpholino, piperidino, 1-pyrrolidinyl, 2-, 3- or 4-piperidyl or 2- or 3-pyrrolidinyl (which may be substituted with alkyl), or alternatively Ra is a radical of structure =CHR'a for which R'a is 3-pyrrolidinylamino, 3- or 4-piperidylamino, 3-pyrrolidinyloxy, 3- or 4-piperidyloxy, 3-pyrrolidinylthio, 3-or 4-piperidylthio which may be substituted with alkyl, or R'a is alkylamino, alkyloxy or alkylthio substituted with 1 or 2 hydroxysulfonyl, alkylamino, dialkylamino (itself optionally substituted with dialkylamino), or with trialkylammonio, 4- or 5-imidazolyl, or with 1 or 2 optionally substituted piperazine rings, morpholino, thiomorpholino, piperidino, 1-pyrrolidinyl, 2-, 3- or 4-piperidyl or 2- or 3-pyrrolidinyl (which may be substituted with alkyl), or Ra is a 3- or 4-quinuclidinylthiomethyl radical, or alternatively 2. Ra is a hydrogen atom and
a) either Rb, Re and Rf are hydrogen atoms, Rd is a radical —NHCH$_3$ or —N(CH$_3$)$_2$ and Rc is a chlorine or bromine atom, or represents an alkenyl radical containing 3 to 5 carbon atoms [if Rd is —N(CH$_3$)$_2$],
b) or Rb, Rd, Re and Rf represent a hydrogen atom and Rc is a halogen, or an aminomonoalkyl, aminodialkyl, alkyloxy, trifluoromethyloxy, thioalkyl, C$_1$ to C$_3$ alkyl or trihalomethyl radical,
c) or Rb, Rc, Re and Rf represent a hydrogen atom and Rd is a halogen, or an ethylamino, diethylamino or methylethylamino, alkyloxy or trifluoro-methyloxy, thioalkyl, C$_1$ to C$_6$ alkyl, aryl or trihalomethyl radical,
d) or Rb, Re and Rf represent a hydrogen atom and Rc is halogen or an aminomonoalkyl or aminodialkyl, alkyloxy or trifluoromethyloxy, thioalkyl or C$_1$ to C$_3$ alkyl radical, and Rd is halogen or an amino, aminomonoalkyl or aminodialkyl, alkyloxy or trifluoromethyloxy, thioalkyl, C$_1$ to C$_6$ alkyl or trihalomethyl radical,
e) or Rc, Re and Rf represent a hydrogen atom and Rb and Rd represent a methyl radical;

or alternatively from the semisynthetic derivatives of the group B streptogramins of general formula:

(B)

in which
Y is a nitrogen atom or a radical =CR$_3$—,
R$_1$ is a hydrogen atom, an alkyl radical (1 to 8 carbons), an alkenyl radical (2 to 8 carbons), a cycloalkyl radical (3 to 8 carbons), a saturated or unsaturated heterocyclyl radical (3 to 8 members), a phenyl radical, a phenyl radical which is substituted [with one or more halogen atoms or hydroxyl, alkyl, alkyloxy, alkylthio, alkylsulfinyl alkylsulfonyl, amino, alkylamino or dialkylamino radicals] or a radical NR'R", it being possible for R' and R", which are identical or different, to be hydrogen atoms or alkyl radicals (1 to 3 carbons) or to form together with the nitrogen atom to which they are attached a 3- to 8-membered heterocycle optionally containing another heteroatom chosen from oxygen, sulfur or nitrogen, optionally substituted [with an alkyl radical, an alkenyl radical (2 to 8 carbons), a cycloalkyl radical (3 to 6 carbons), a saturated or unsaturated heterocyclyl radical (4 to 6 members), a benzyl radical, a phenyl radical or a phenyl radical which is substituted as defined above for the definition of R$_1$]

or alternatively when Y is a radical =CR$_3$—, R$_1$ may also be halomethyl, hydroxymethyl, alkyloxymethyl, alkylthiomethyl in which the alkyl portion is optionally substituted with NR'R", alkylsulfinylmethyl, alkylsulfonylmethyl, acyloxymethyl, benzoyloxymethyl, cyclopropylaminomethyl or —(CH$_2$)$_n$NR'R" (n being an integer from 1 to 4 and R' and R" being as defined above)

or alternatively if R$_3$ is a hydrogen atom, R$_1$ may also be formyl, carboxyl, alkyloxycarbonyl, or —CONR'R" for which R' and R" are as defined above, or alternatively when Y is a nitrogen atom, R$_1$ may also be a radical —XR° for which X is an oxygen or sulfur atom, a sulfinyl or sulfonyl radical, or an NH radical and R° is an alkyl radical (1 to 8 carbons), a cycloalkyl radical (3 to 6 carbons), a saturated or unsaturated heterocyclyl radical (3 to 8 members), a heterocyclylmethyl radical (3 to 8 members) in which the heterocyclyl portion is attached to the methyl radical by a carbon atom, a phenyl radical, a phenyl radical which is substituted [with one or more halogen atoms or hydroxyl, alkyl, alkyloxy, alkylthio, alkylsulfiny, alkylsulfonyl, amino, alkylamino or dialkylamino radicals] or a radical —(CH$_2$)$_n$NR'R" for which R' and R" are as defined above and n is interger from 2 to 4, or alternatively, if X represents NH, R° may also represent a hydrogen atom, R$_2$ is a hydrogen atom or an alkyl radical (1 to 3 carbons),
R$_3$ is a hydrogen atom or an alkyl radical, a carboxyl radical, an alkyloxycarbonyl radical, or a carbamoyl radical of structure —CO—NR'R" in which R' and R" are as defined above,
Ra is a methyl or ethyl radical, and
Rb, Rc and Rd have the definitions below:
1) Rb and Rc are hydrogen atoms and Rd is a hydrogen atom or a methylamino or dimethylamino radical,
2) Rb is a hydrogen atom, Rc is a hydrogen, chlorine or bromine atom, or represents an alkenyl radical (3 to 5C), and Rd is a radical —NMe—R'" for which R'" represents a radical alkyl, hydroxyalkyl (2 to 4C), or alkenyl (2 to 8C) which is optionally substituted, with phenyl, cycloalkyl(3 to 6C)methyl, benzyl, benzyl which is substituted [with one or more halogen atoms or hydroxyl, alkyl, alkyloxy, alkylthio, alkylsulfinyl, alkylsulfonyl, amino, alkylamino or dialkylamino radicals], heterocyclylmethyl or heterocyclylethyl in which the heterocyclyl portion is saturated or unsaturated and contains 5 to 6 members and one or two heteroatoms chosen from sulfur, oxygen or nitrogen optionally substituted, [with an alkyl radical, an alkenyl radical (2 to 8 carbons), a cycloalkyl radical (3 to 6 carbons), a saturated or unsaturated heterocyclyl radical (4 to 6 members), a phenyl radical, a phenyl radical which is substituted as defined above for the definition of R$_1$ or a benzyl radical], or alternatively R'" represents a cyanomethyl radical, or —CH$_2$CORe for which either Re is —OR'e, R'e being hydrogen, alkyl (1 to 6 carbons), alkenyl (2 to 6 carbons), benzyl or heterocyclylmethyl in which the heterocyclyl portion contains 5 to 6 members and 1 or 2 heteroatoms chosen from sulfur, oxygen or nitrogen or Re is an alkylamino radical, an alkylmethylamino radical, a heterocyclylamino radical or a heterocyclylmethylamino radical in which the heterocyclyl portion is saturated and contains 5 to 6 members and one or two heteroatoms chosen from sulfur, oxygen or nitrogen optionally substituted with an alkyl, benzyl or alkyloxycarbonyl radical, 3) Rb is a hydrogen atom, Rd is a radical —NHCH$_3$ or —N(CH$_3$)$_2$ and Rc is a chlorine or bromine atom, or represents an alkenyl radical (3 to 5C), [if Rd is —N(CH$_3$)$_2$], 4) Rb and Rd are hydrogen atoms and Rc is a halogen atom, or an alkylamino or dialkylamino, alkyloxy, trifluoromethoxy, thioalkyl, alkyl (1 to 6C) or trihalomethyl radical, 5) Rb and Rc are hydrogen atoms and Rd is a halogen atom, or an ethylamino, diethylamino or methylethylamino, alkyloxy or trifluoromethoxy, alkylthio, alkylsulfinyl, alkylsulfonyl, alkyl (1 to 6C), phenyl or trihalomethyl radical, 6) Rb is a hydrogen atom and Rc is a halogen atom or an alkylamino or dialkylamino, alkyloxy or trifluoromethoxy, thioalkyl or alkyl (1 to 3C) radical and Rd is a halogen atom or an amino, alkylamino or dialkylamino, alkyloxy or trifluoromethoxy, thioalkyl, alkyl (1 to 6C) or trihalomethyl radical, 7) Rc is a hydrogen atom and Rb and Rd represent a methyl radical, as well as their salts.

It is understood that the combinations of the derivatives according to the invention and of the group B streptogramins are also included within the scope of the present invention.

The group B streptogramin derivatives of structure (B) may be prepared according to the methods described in International Application PCT/FR 99/00409.

In vitro on *Staphylococcus aureus* 209P, the streptogramin derivatives according to the invention have proved active at concentrations of between 0.015 and 32 µg/ml alone or combined with a group B derivative such as pristinamycin I$_B$ and at concentrations of between 0.015 et 32 µg/ml on *Staphylococcus aureus* Schiclia (resistant to meticillin) alone or combined with pristinamycin I$_B$; in vivo, they synergise the antimicrobial activity of pristinamycin I$_B$ on experimental infections of mice with *Staphylococcus aureus* IP8203 at doses of between 5 and 150 mg/kg by the subcutaneous route (CD$_{50}$) and the majority of them also by the oral route, at doses of between 30 and 150 mg/kg (CD$_{50}$).

Finally, the products according to the invention are particularly advantageous because of their low toxicity. None of the products manifested toxicity at doses of 150 mg/kg on *Staphylococcus aureus* IP8203, twice per day, by the subcutaneous route or by the oral route in mice.

Of particular interest are the products of general formula (I) for which:

R$_1$ represents a fluorine, chlorine, bromine or iodine atom or an azido or thiocyanato radical, R$_2$ represents a methyl radical, R$_3$ represents a hydrogen atom or a radical R'$_3$—CO— for which R'$_3$ is phenyl or phenylalkyl which are substituted or unsubstituted on the phenyl radical [with one or more radicals chosen from alkyl, optionally carrying a radical NR'R" in which the radicals R' and R", which are identical or different, may be hydrogen atoms or alkyl radicals which can form together with the nitrogen atom to which they are attached a 3- to 8-membered saturated or unsaturated heterocyclyl radical optionally comprising another hetero atom chosen from oxygen, sulfur or nitrogen, it being possible for the said heterocycle itself to be substituted with one or more radicals (alkyl, hydroxyalkyl, alkyloxyalkyl, alkyloxycarbonylalkyl, aryl, 3- to 8-membered saturated or unsaturated heterocyclyl or heterocyclylalkyl, or —CH$_2$—CO—NR'R"), or alternatively R' and/or R" may be a radical hydroxyalkyl, phenyl, 3- to 8-membered saturated or unsaturated heterocyclylalkyl, —CO—NR'R" for which NR'R" is as defined above, or alkyl or acyl which are substituted with NR'R" as defined above], or alternatively R'$_3$ may be a phenyl radical substituted with one or more radicals [chosen from alkyl, which may be substituted with an alkyloxy or alkylthio radical themselves optionally carrying a carboxyl radical or a radical NR'R" as defined above, or chosen from acyloxy which may be substituted with NR'R" as defined above], or alternatively R'$_3$ maybe chosen from alkyl or cycloalkyl radicals which are optionally substituted [with a carboxyl or carboxyalkyl-disulfanyl radical or with a radical NR'R", —CH$_2$—NR'R" or —CO—NR'R", or with an alkyloxycarbonyl, alkyloxy or alkyldisulfanyl radical which are optionally substituted with NR'R" or —CO—NR'R" for which NR'R" is as defined above], or alternatively R'$_3$ may be chosen from 3- to 8-membered saturated or unsaturated heterocycle radicals which are optionally substituted [with alkyl or acyl which are themselves optionally substituted with NR'RH"], it being understood that the heterocycles are chosen from pyrrolidinyl, imidazolyl, pyridyl, piperidinyl, piperazinyl or morpholinyl, and the bond ---represents a single bond (stereochemistry 27R) or a double bond, as well as their salts when they exist;

and among these products, more especially:

(16R)-16-deoxo-16-fluoropristinamycin II$_B$;

(16R)-16-deoxo-16-thiocyanatopristinamycin II$_B$;

(16R)-16-deoxo-16-chloropristinamycin II$_B$;

(16R)-16-azido-16-deoxopristinamycin II$_B$;

(16R)-16-deoxo-16-fluoropristinamycin II$_A$.

The following examples, given with no limitation being implied, illustrate the present invention.

In the following examples, the nomenclature 16-deoxopristinamycin II$_A$ (or II$_B$) means the replacement of the ketone function at the 16-position with 2 atoms of hydrogen. As the chromatography progresses, all the fractions are analyzed by thin-layer chromatography (TLC), on Merck 60F254 silica plates. The fractions corresponding to the same spot in TLC are grouped together and then concentrated to dryness under reduced pressure (30° C.; 2.7 kPa). The residues thus obtained are analyzed by the usual spectroscopic techniques (NMR; IR; MS), which makes it possible to identify the expected product.

EXAMPLE 1

(16R)-16-Deoxo-16-fluoropristinamycin II$_B$ 0.2 cm$^3$ of acetic acid and 0.6 g of tetra-n-butylammonium fluoride trihydrate are added, at 20° C., under an argon atmosphere, to 1.12 g of ((16R)-16-deoxo-16-fluoro-14-O-(tert-butyldiphenylsilyl) pristinamycin II$_B$ in solution in 10 cm$^3$ of tetrahydrofuran. After stirring for 168 hours, the reaction mixture is concentrated to dryness under reduced pessure (2.7 kPa) to give 1 g of a brown oil which is purified by flash chromatography, [eluent: dichloromethane/methanol/acetonitrile (90/5/5 by volume)]. 0.3 g of (16R)-16- deoxo-16-fluoropristinamycin II$_B$ is obtained in the form of a light beige solid melting at around 125° C. (dec.).

$^1$H NMR spectrum (400 MHz, CDCl$_3$, δ in ppm): 0.96 (d, J=6.5 Hz: 3H); 1.00 (d, J=6.5 Hz: 3H); 1.10 (d, J=6.5 Hz: 3H); from 1.55 to 2.05 (mt: 5H); 1.83 (s: 3H); from 2.10 to 2.30 (mt: 2H); 2.76 (mt: 1H); 2.98 (mt: 1H); 3.21 (mt: 1H); 3.48 (mt: 1H); 3.87 (mt: 1H); 4.07 (mt: 1H); 4.55 (mt: 1H); from 4.75 to 4.90 (mt: 3H); 5.14 (decoupled doublet, J$_{HF}$=48 Hz: 1H); 5.39 (d, J=9 Hz: 1H); 5.71 (mt: 1H); 5.82 (dd, J=17 and 2 Hz: 1H); 6.00 (mt: 1H); 6.21 (d, J=16 Hz: 1H); 6.52 (dd, J=17 and 5 Hz: 1H); 8.12 (s: 1H).

(16R)-16-Deoxo-16-fluoro-14-O-(tert-butyldiphenylsilyl)pristinamycin II$_B$ may be prepared in the following manner:

0.464 cm$^3$ of diethylaminosulfur trifluoride is slowly added, at 20° C., under an argon atmosphere, to 2 g of (16S)-16-hydroxy-14-O-(tert-butyidiphenylsilyl)pristinanycin II$_B$ in solution in 50 cm$^3$ of dichloromethane. After stirring for 2 hours, the reaction mixture is poured over 100 cm$^3$ of a saturated aqueous sodium bicarbonate solution. The organic phase is decanted off, washed with twice 100 cm$^3$ of water, dried over magnesium sulfate, filtered and then concentrated to dryness under reduced pressure (2.7 kPa) to give 2.1 g of an ocher-colored solid which is purified by flash chromatography (eluent: dichloromethane/acetonitrile/ methanol gradient (100/0/0; 99/0.5/0.5 and then 98/1/1 by volume)]. 1.35 g of (16R)-16-deoxo-16-fluoro-14-O-(tert-butyldiphenylsilyl)pristinamycin II$_B$ are obtained in the form of a white solid melting at around 116° C. (dec.).

$^1$H NMR spectrum (400 MHz, CDCl$_3$, δ in ppm): 0.96 (d, J=6.5 Hz: 3H); 0.99 (d, J=6.5 Hz: 3H); from 1.00 to 1.15 (mt: 12H); 1.29 (s: 3H); from 1:55 to 1.95 (mt: 4H); 1.96 (mt: 1H); 2.13 (mt: 1H); 2.24 (mt: 1H); 2.76 (mt: 1H); 2.85 (mt: 1H); 3.03 (mt: 1H); 3.39 (mt: 1H); 3.80 (mt: 1H); 4.01 (mt: 1H); 4.57 (mt: 1H); 4.72 (mt: 1H); from 4.75 to 4.85 (mt: 2H); 5.01 (decoupled doublet, J$_{HF}$=48 Hz: 1H); 5.38 (d, J=9 Hz: 1H); 5.50 (mt: 1H); 5.81 (dd, J=17 and 1.5 Hz: 1H); 5.97 (mt: 1H); 6.10 (d, J=15.5 Hz: 1H); 6.49 (dd, J=17 and 5 Hz: 1H); from 7.30 to 7.50 (mt: 6H); 7.63 (broad d, J=7 Hz: 2H); 7.68 (broad d, J=7 Hz: 2H); 8.08 (s: 1H).

(16S)-16-Hydroxy-14-O-(tert-butyldiphenylsilyl)pristinamycin II$_B$ may be prepared in the following manner:

To 22 g of (16S)-16-hydroxypristinamycin II$_B$ in solution in 200 cm$^3$ of dichloromethane, there are added, at 20° C., under an argon atmosphere, 29 cm$^3$ of diisopropylethylamine, 43.2 cm$^3$ of tert-butyldiphenylchlorosilane, dropwise, and 1.01 g of 4-dimethylaminopyridine. After stirring for 22 hours, the reaction mixture is poured over 600 cm$^3$ of a saturated aqueous sodium bicarbonate solution. The aqueous phase is decanted off and then extracted with twice 100 cm$^3$ of dichloromethane. The organic phases are combined, washed with 400 cm$^3$ of a saturated aqueous sodium chloride. solution, dried over sodium sulfate, filtered and then concentrated to dryness under reduced pressure (2.7 kPa) to give 70.6 g of an orange-colored viscous oil which is stirred in 600 cm$^3$ of diisopropyl ether for 16 hours. After filtration and drying under reduced pressure (2.7 kPa) at 20° C., 28 g of (16S)-16-hydroxy-14-O-(tert-butyldiphenylsilyl)pristinamycin II$_B$ are obtained in the form of a pink solid melting at around 133° C. (dec.).

$^1$H NMR spectrum (400 MHz, CDCl$_3$, δ in ppm); 0.95 (d, J=6.5 Hz: 3H); from 1.00 to 1.05 (mt: 9H); 1.08 (s: 9H); from 1.40 to 1.80 (mt: 3H); from 1.90 to 2.15 (mt: 3H); 2.23 (broad d, J=14 Hz: 1H); 2.75 (mt: 1H); 2.83 (dd, J=17 and 11 Hz: 1H); 3.10 (dd, J=17 and 2.5 Hz: 1H); 3.25 (mt: 1H); from 3.60 to 3.75 (mt: 2H); 4.49 (mt: 1H); 4.56 (mt: 1H); from 4.60 to 4.70 (mt: 2H); 4.87 (mt: 1H); 5.49 (mt: 1H); 5.74 (dd, J=17 and 2 Hz: 1H); 5.78 (d, J=9 Hz: 1H); 5.95 (mt: 1H); 6.04 (d, J=16 Hz: 1H); 6.41 (dd, J=17 and 4 Hz: 1H); from 7.30 to 7.50 (mt: 6H); 7.64 (dd, J=7 and 1.5 Hz: 2H); 7.69 (dd, J=7 and 1.5 Hz: 2H); 8.11 (s: 1H).

(16S)-16-Hydroxypristinamycin II$_B$ may be prepared in the following manner:

A suspension of 11.35 g of sodium borohydride in 550 cm$^3$ of dichloromethane is heated under reflux for 20 minutes. There are then added, dropwise, over about 30 minutes, 68.6 cm$^3$ of acetic acid followed by a solution (previously dried over sodium sulfate) of 52.75 g of pristinamycin II$_B$ in 230 cm$^3$ of dichloromethane, over about 45 minutes. The reaction mixture is stirred for 4.5 hours under reflux and then for 16 hours at 20° C. 500 cm$^3$ of dichloromethane and 1500 cm$^3$ of water are then added to the reaction mixture. The organic phase is decanted off and the aqueous phase is extracted with 500 cm$^3$ of dichloromethane. The organic phases are combined and the pH is adjusted to 8 by a slow addition of 1000 cm$^3$ of a saturated aqueous sodium bicarbonate solution. The resulting organic phase is washed successively with 1000 cm$^3$ of water and 1000 cm$^3$ of a saturated aqueous sodium chloride solution and then treated with 3S vegetable black, dried over sodium sulfate, filtered and concentrated to dryness under reduced pressure (2.7 kPa) to give 50 g of a light yellow solid. 378 cm3 of a 0.5 M aqueous ammonium hydroxide solution are added, at 20° C., to a solution of the preceding solid in 900 cm$^3$ of dichloromethane. After stirring for 16 hours at 20° C., the organic phase is decanted off, washed with 1000 cm$^3$ of water and then with 1000 cm$^3$ of a saturated aqeuous sodium chloride solution, dried over sodium sulfate, filtered and concentrated to dryness under reduced pressure (2.7 kPa) to give 46 g of a pale yellow solid which is purified by flash chromatography[eluent: dichloromethane/methanol gradient (98/2 and 97/3 by volume)]. 31.68 g of (16S)-16-hydroxypristinamycin II$_B$ are obtained in the form of an off-white solid melting at around 131° C. (dec.).

$^1$H NMR spectrum (400 MHz, CDCl$_3$, δ in ppm): 0.96 (d, J=6.5 Hz: 3H); 1.02 (d, J=6.5 Hz: 3H); 1.07 (d, J=6.5 Hz: 3H); from 1.70 to 1.90 (mt: 3H); 1.76 (s: 3H); 1.97 (mt: 2H); 2.12 (mt: 1H); 2.26 (broad d: 14.5 Hz: 1H); 2.56 (d, J=3 Hz: 1H); 2.76 (mt: 1H); 2.90 (dd, J=16 and 10 Hz: 1H); 3.08 (dd, J=16 and 3 Hz: 1H); 3.35 (mt: 1H); 3.82 (mt: 2H); 3.99 (d, J=2.5 Hz: 1H); from 4.40 to 4.55 (mt: 2H); from 4.65 to 4.75 (mt: 2H); 5.03 (mt: 1H); from 5.65 to 5.85 (mt: 3H); 6.01 (mt: 1H); 6.21 (d, J=16 Hz: 1H); 6.46 (dd, J=17 and 5 Hz: 1H); 8.13 (s: 1H).

EXAMPLE 2

(16R)-16-Deoxo-16-fluoropristinamycin II$_B$ 970 cm$^3$ of triethylamine trihydrofluoride are slowly added, over 40 minutes at 40° C., under an argon atmosphere, to 257 g of (16R)-16-deoxo-16-fluoro-14-O-(tert-butyldimethylsilyl)pristinamycin II$_B$ in solution in 2500 cm$^3$ of dichloromethane. After stirring for 2 hours at 40° C., the reaction mixture is cooled to 8° C. and then hydrolyzed by a slow addition, over 25 minutes, of 1940 cm$^3$ of water. After stirring for 10 minutes, the organic and aqueous phases are decanted off and the milky interface is taken up in 4000 cm$^3$ of water and 1000 cm$^3$ of dichloromethane. After stirring both phases, the organic phase is decanted off and the aqueous phases are combined and then extracted with 1000 cm$^3$ of dichloromethane. The organic phases are combined and added to 1500 cm$^3$ of water. The pH of the aqueous phase is adjusted to 7 by a slow addition, over 15 minutes at 10° C., of 400 cm³ of a saturated aqueous sodium bicarbonate solution. The organic phase is decanted off, diluted with 1500 cm³ of ethyl acetate and then washed with 1000 cm³ of water. The organic phase is decanted off and the aqueous phase is extracted with twice 1500 cm³ of ethyl acetate and then filtered on Celite® over sintered glass. The Celite® is rinsed with 3 times 400 cm³ of ethyl acetate. The organic phases are combined, dried over sodium sulfate and then filtered on Celite®9 over sintered glass. The Celite® is rinsed with 4 times 800 cm³ of ethyl acetate. The filtrate is concentrated to dryness under reduced pressure (2.7 kPa) to give, after drying to a constant weight at 25° C., 218.5 g of (16R)-16-deoxo-16-fluoropristinamycin $II_B$ in the form of a white crystalline powder melting at around 133° C. (dec.).

¹H NMR spectrum (400 MHz, CDCl₃, δ in ppm): 0.96 (d, J=6.5 Hz: 3H); 1.00 (d, J=6.5 Hz: 3H); 1.10 (d, J=6.5 Hz: 3H); from 1:55 to 2.05 (mt: 55H); 1.83 (s: 3H); from 2.10 to 2.30 (mt: 2H); 2.76 (mt: 1H); 2.98 (mt: 1H); 3.21 (mt: 1H); 3.48 (mt: 1H); 3.87 (mt: 1H); 4.07 (mt: 1H); 4.55 (mt: 1H); from 4.75 to 4.90(mt: 3H); 5.14 (decoupled doublet, $J_{HF}$=48 Hz: 1H); 5.39 (d, J=9 Hz: 1H); 5.71 (mt: 1H); 5.82 (dd, J=17 and 2 Hz: 1H); 6.00 (mt: 1H); 6.21 (d, J=16 Hz: 1H); 6.52 (dd, J=17 and 5Hz: 1H); 8.12 (s: 1H).

(16R)-16-Deoxo-16-fluoro-14-O-(tert-butyldimethylsilyl)pristinamycin $II_B$ may be prepared in the following manner:

Carrying out the procedure in a manner similar to that described in Example 1, but starting with 22 g of (16S)-16-hydroxy-14-O-(tert-butyldimethylsilyl)pristinamycin $II_B$ in solution in 500 cm³ of dichloromethane, 6.7 cm³ of diethylaminosulfur trifluoride are slowly added at 20° C., under an argon atmosphere. After stirring for 4 hours under a treatment similar to that in Example 1, 25 g of an orange-colored oil are obtained, which oil is purified by flash chromatography [eluent: dichloromethane/methanol/acetonitrile gradient (100/0/0; 99/0.5/0.5 to 96/2/21/by volume)]. 6.6 g of (16R)-16-deoxo-16-fluoro-14-O-(tert-butyldimethylsilyl)pristinamycin $II_B$ are obtained in the form of a light yellow solid melting at around 128° C. (dec.).

¹H NMR spectrum (400 MHz, CDCl₃, δ in ppm): 0.04 (s: 3H); 0.07 (s: 3H); 0.89 (s: 9H); 0.96 (d, J=6.5 Hz: 3H); 0.99 (d, J=6.5Hz: 3H); 1.09 (d, J=6.5 Hz: 3H); from 1.50 to 2.05 (mt: 5H); 1.79 (s: 3H); from 2.10 to 2.25 (mt: 2H); 2.76 (mt: 1H); 2.90 (mt: 1H); 3.15 (mt: 1H); 3.43 (mt: 1H); 3.88 (mt: 1H); 4.09 (mt: 1H); 4.59 (mt: 1H); 4.75 (mt: 1H); 4.79 (dd, J=10 and 1.5 Hz: 1H); 4.84 (dd, J=9 and 3 Hz: 1H); 5.12 (decoupled doublet, $J_{HF}$=48 Hz: 1H); 5.34 (d, J=9 Hz: 1H); 5.64 (mt: 1H); 5.82 (dd, J=17 and 2 Hz: 1H); 5.99 (mt: 1H); 6.20 (d, J=16 Hz: 1H); 6.50 (dd, J=17 and 5 Hz: 1H); 8.09 (s: 1H).

(16S)-16-Hydroxy-14-O-(tert-butyldimethylsilyl)pristinamycin $II_B$ may be prepared in the following manner:

44.4 cm³ of diisopropylethylamine and 39.6 g of tert-butyldimethylchlorosilane in solution in 140 cm³ of dichloromethane are added, at 20° C., under an argon atmosphere, to 27 g of (16S)-16-hydroxypristinamycin $II_B$ (prepared as described in Example 1) in solution in 270 cm³ of dichloromethane. After stirring for 17 hours, the reaction mixture is washed with three times 300 cm³ of water. The organic phase is dried over magnesium sulfate, filtered and then concentrated to dryness under reduced pressure (2.7 kPa) to give an orange-colored oil which is purified by flash chromatography [eluent: dichloromethane/methanol/acetonitrile (100/0/0; 99/0.5/0.5 to 96/2/2 by volume)]. 24 g of (16S)-16-hydroxy-14-O-(tert-butyldimethylsilyl)-pristinamycin $II_B$ are obtained in the form of a light yellow solid melting at around 139° C. (dec.).

¹H NMR spectrum (400 MHz, CDCl₃, δ in ppm): 0.05 (s: 3H); 0.10 (s: 3H); 0.91 (s: 9H); 0.96 (d, J=6.5 Hz: 3H); 1.02 (d, J=6.5 Hz: 3H); 1.06 (d, J=6.5 Hz: 3H); from 1.70 to 2.05 (mt: 5H); 1.71 (s: 3H); 2.12 (mt: 1H); 2.31 (broad d, J=14 Hz: 1H); from 2.70 to 2.80 (mt: 1H); 2.80 (dd, J=17 and 11 Hz: 1H); 3.06 (dd, J=17 and 2.5 Hz: 1H); 3.30 (mt: 1H); 3.79 (mt: 2H); 4.47 (broad t, J=10 Hz: 1H); 4.52 (s: 1H); 4.54 (mt: 1H); from 4.65 to 4.75 (mt: 2H); 4.99 (mt: 1H); 5.69 (mt: 1H); 5.76 (dd, J=17 and 2 Hz: 1H); 5.78 (d, J=9 Hz: 1H); 6.00 (mt: 1H); 6.20 (d, J=16 Hz: 1H); 6.43 (dd, J=17 and 4 Hz: 1H); 8.12 (s: 1H).

EXAMPLE 3

(16R)-16-Deoxo-16-fluoropristinamycin $II_B$ 0.5 cm³ of a 1N aqueous hydrochloric acid solution is added, at 0° C., under an argon atmosphere, to a suspension of 0.09 g of sodium para-toluenesulfinate in 6 cm³ of dichloromethane. After stirring for 15 minutes at 20° C., the organic phase is decanted off, dried over magnesium sulfate and filtered. 0.26 g of (16R)-14-O-allyl-16-deoxo-16-fluoropristinamycin $II_B$ and 0.04 g of tetrakis(triphenylphosphine)palladium are added to the filtrate, at 20° C. under an argon atmosphere. After stirring for two hours, 0.01 g of triethylamine is added. After stirring for an additional 30 minutes, the reaction mixture is concentrated to dryness and then purified by flash chromatography [eluent: dichloromethane/methanol/acetonitrile (90/5/5 by volume)] to give 0.2 g of (16R)-16-deoxo-16-fluoropristinamycin $II_B$.

¹H NMR spectrum (400 MHz, CDCl₃, δ in ppm): 0.96 (d, J=6.5 Hz: 3H); 1.00 (d, J=6.5 Hz: 3H); 1.10 (d, J=6.5 Hz: 3H); from 1.50 to 2.05 (mt: 5H); 1.62 (d, J=4 Hz: 1H); 1.83 (s: 3H); from 2.10 to 2.30 (mt: 2H); 2.77 (mt: 1H); 2.98 (mt: 1H); 3.21 (mt: 1H); 3.48 (mt: 1H); 3.87 (mt: 1H); 4.06 (mt: 1H); 4.55 (mt: 1H); from 4.75 to 4.85 (mt: 3H); 5.14 (decoupled doublet, $J_{HF}$=48 Hz: 1H); 5.39 (d, J=9 Hz: 1H); 5.72 (mt: 1H); 5.82 (dd, J=16 and 2 Hz: 1H); 5.98 (mt: 1H); 6.21 (d, J=16 Hz: 1H); 6.51 (dd, J=16 and 5 Hz: 1H); 8.11 (s: 1H).

(16R)-14-O-allyl-16-deoxo-16-fluoropristinamycin $II_B$ may be prepared in the following manner:

0.28 cm³ of diethylaminosulfur trifluoride in solution in 5 cm³ of dichloromethane is added dropwise, at 0° C. under argon atmosphere, to 0.8 g of (16S)-14-O-allyl-16-hydroxypristinamycin $II_B$ in solution in 25 cm³ of dichloromethane. After stirring for 45 minutes at 0° C. and then returning to 20° C., the reaction mixture is poured over 70 cm³ of a saturated aqueous sodium hydrogen carbonate solution at 0° C. The resulting mixture is extracted with 100 cm³ of dichloromethane. The organic phase is successively washed with 70 cm³ of a saturated aqueous sodium hydrogen carbonate solution and 70 cm³ of a saturated aqueous sodium chloride solution and then dried over magnesium sulfate. After filtration and concentrating to dryness under reduced pressure (2.7 kPa) at 20° C., 0.8 g of (16R)-14-O-allyl-16-deoxo-16-fluoropristinamycin $II_B$ is obtained in the form of a cream-colored solid.

¹H NMR spectrum (400 MHz, CDCl₃, δ in ppm): 0.96 (d, J=6.5 Hz: 3H); 1.00 (d, J=6.5 Hz: 3H); 1.09 (d, J=6.5 Hz: 3H); from 1.50 to 2.05 (mt: 5H); 1.81 (s: 3H); 2.16 (mt: 1H); 2.29 (mt: 1H); 2.76 (mt: 1H); 2.93 (mt: 1H); 3.18 (dt, J=17 and 7 Hz: 1H); 3.45 (mt: 1H); from 3.80 to 3.95 (mt: 2H); from 4.00 to 4.15 (mt: 2H); 4.47 (dt, J=9.5 and 4 Hz: 1H); 4.59 (mt: 1H); 4.78 (dd, J=10 and 1.5 Hz: 1H); 4.83 (dd, J=9 and 3 Hz: 1H); from 5.05 to 5.35 (mt: 4H); 5.69 (mt: 1H);

5.82 (dd, J=16 and 2 Hz: 1H); 5.90 (mt: 1H); 6.00 (mt: 1H); 6.25 (d, J=16 Hz: 1H); 6.51 (dd, J=16 and 4 Hz: 1H); 8.11 (s: 1H).

(16S)-14-O-allyl-16-hydroxypristinamycin $II_B$ may be prepared in the following manner:

19 g of potassium carbonate and 31.5 cm³ of allyl bromide are added to 10.6 g of (16S)-16-hydroxypristinamycin $II_B$ (prepared as described in Example 1) in solution in 500 cm³ of 2-butanone. The reaction mixture is heated under reflux for 90 hours. After cooling to 20° C. under filtration, the reaction mixture is concentrated under reduced prssure (2.7 kPa). The residue is taken up in 100 cm³ of distilled water and with 300 cm³ of dichloromethane. The organic phase is decanted off and then washed with 100 cm³ of distilled water, dried over magnesium sulfate, filtered and concentrated to dryness, under reduced pressure (2.7 kPa), to give 12.5 g of a residue which is purified by flash chromatography [eluent: dichloromethane/methanol (95/5 by volume)]. A solid is obtained which is stirred in diethyl ether, filtered and dried (2.7 kPa) at, 20° C., to give 1.4 g of (16S)-14-O-allyl-16-hydroxypristinamycin $II_B$ in the form of a white powder.

$^1$H NMR spectrum (400 MHz , CDCl$_3$, δ in ppm): 0.97 (d, J=6.5 Hz: 3H); 1.04 (d, J=6.5 Hz: 3H); 1.07 (d, J=6.5 Hz: 3H); from 1.70 to 2.05 (mt: 5H); 1.75 (s: 3H); 2.12 (mt: 1H); 2.34 (broad d, J=16 Hz: 1H); 2.77 (mt: 1H); 2.85 (dd, J=16 and 10 Hz: 1H); 3.09 (dd, J=16 and 3 Hz: 1H); 3.32 (mt: 1H ); from 3.75 to 3.90 (mt: 3H); from 4.05 to 4.15 (mt: 2H); 4.42 (mt: 1H ); 4.53 (mt: 1H); from 4.65 to 4.75 (mt: 3H); from 5.15 to 5.30 (mt: 2H); from 5.65 to 5.80 (mt: 1H); 5.70 (broad d, J=9 Hz: 1H); 5.80 (dd, J=16 and 1.5 Hz: 1H); 5.79 (mt: 1H); 5.98 (mt: 1H); 6.24 (d, J=16 Hz: 1H); 6.45 (dd, J=16 and 4Hz: 1H); 8.14 (s: 1H).

EXAMPLE 4

(16R)-16-Deoxo-16-thiocyanatopristinamycin $II_B$ 5 cm³ of triethylamine trihydrofluoride are added, at 20° C., to 0.85 g of (16R)-16-deoxo-16-thiocyanato-14-O-(tert-butyldiphenylsilyl)pristinamycin $II_B$ in solution in 40 cm³ of dichloromethane. After stirring for 20 hours under reflux, 3 cm³ of triethylamine trihydrofluoride are added and the reflux is maintained for another 3 hours. The reaction mixture is then poured over 80 cm³ of water and then neutralized by slow addition of sodium bicarbonate. The organic phase is decanted off, dried over magnesium sulfate, filtered and concentrated to dryness under reduced pressure (2.7 kPa) to give 0.61 g of a solid which is purified by flash chromatography [eluent: dichloromethane/methanol (96/4 by volume)]. 0.36 g of (16R)-16-deoxo16-20thiocyanato-pristinamycin $II_B$ is obtained in the form of a white solid melting at around 140° C. (dec.).

$^1$H NMR spectrum (400 M, CDCl$_3$, δin ppm): 0.96 (d, J=6.5 Hz: 3H); 1.00 (d, J=6.5 Hz: 3H); 1.09 (d, J=6.5 Hz: 3H); from 1.75 to 2.05 (mt: 5H); 1.85 (s: 3H); from 2.10 to 2.30 (mt: 2H ); 2.77 (mt: 1H); 3.15 (dd, J=17 and 7 Hz: 1H); 3.40 (dd, J=17 and 7Hz: 1H); 3.52(mt: 1H);3.62 (mt: 1H); 3.83(mt: 1H); 4.02 (mt: 1H); 4.52 (mt: 1H); from 4.75 to 4.85 (mt: 2H); 4.77 (dd, J=10 and 2 Hz: 1H); 5.36 (d, J=9 Hz: 1H); 5.77 (mt: 1H); 5.81 (mt: 1H); 5.81 (dd, J=16 and 2Hz: 1H); 6.05 (mt: 1H): 6.21 (d, J=16 Hz: 1H); 6.52 (dd, J=16 and 5 Hz: 1H); 8.14 (s: 1H).

(16R)-16-deoxo-16thiocyanato-14-O-(tert-butyldiphenylsilyl)pristinamycin $II_B$ may be prepared in the following manner:

To 5.85 g of tetra-n-butylammonium thiocyanate in solution in 70 cm³ of dichloromethane, there are added, at 20° C., under an argon atmosphere, 2.6 g of (16S)-16-hydroxy-14-O-(tert-butyldiphenylsilyl)pristinamycin $II_B$ (prepared as described in Example 1) and then, dropwise, 1.56 cm³ of diethylaminosulfur trifluoride. After stirring for 10 minutes, the reaction mixture is diluted with 100 cm³ of dichloromethane. The solution obtained is successively washed with twice 100 cm³ of water and 100 cm³ of a saturated aqueous sodium chloride solution and then dried over magnesium sulfate, filtered and concentrated to dryness under reduced pressure (2.7 kPa) to give 7.6 g of a dark yellow oil which is purified by flash chromatography [eluent: cyclohexane/ethyl acetate (6/4 by volume)]. 0.87 g of (16R)-16-deoxo-16-thiocyanato-14-O-(tert-butyldiphenylsilyl)pristinamycin $II_B$ is obtained in the form of a white solid.

$^1$H NMR spectrum (400 MHz, CDCl$_3$, δ in ppm): 0.96 (d, J=6.5 Hz: 3H); 1.00 (d, J=6.5 Hz: 3H); from 1.05 to 1.10 (mt: 3H); 1.06 (s: 9H); 1.28 (s: 3H); from 1.70 to 1.95 (mt: 4H); 1.96 (mt: 1H); from 2.10 to 2.25 (mt: 2H); 2.77 (mt: 1H); 3.04 (dd, J=17 and 6 Hz: 1H); 3.27 (dd, J=17 and 8 Hz: 1H); from 3.40 to 3.50 (mt: 2H); 3.75 (mt: 1H); 3.95 (mt: 1H); 4.53 (mt: 1H); 4.67 (mt: 1H); from 4.75 to 4.85 (mt: 2H); 5.35 (d, J=9 Hz: 1H); 5.56 (mt: 1H); 5.81 (dd, J=16 and 1.5 Hz: 1H); 6.04 (mt: 1H); 6.11 (d, J=16 Hz: 1H); 6.49 (dd, J=16 and 5 Hz: 1H); from 7.30 to 7.50 (mt: 6H); 7.63 (broad d, J=7 Hz: 2H); 7.69 (mt: 2H); 8.12 (s: 1H).

EXAMPLE 5

(16R)-16-Deoxo-16-bromopristinamycin $II_B$

Carrying out the procedure in a manner similar to that described in Example 4, but starting with 1.2 g of (16R)-16-deoxo-16-bromo-14-O-(tert-butyldiphenylsilyl)-pristinamycin $II_B$ in solution in 30 cm³ of dichloromethane, 7.5 -cm³ of triethylamine trihydrofluoride are added at 20° C. After stirring for 25 hours under reflux and a treatment similar to that in Example 4, an orange-colored solid is obtained, which solid is purified by flash chromatography [eluent: dichloromethane/methanol (97/3 by volume)]. 0.78 g of a white solid is obtained, which solid is recrystallized from 5 cm³ of acetonitrile to give 0.48 g of (16R)-16-deoxo-16-bromopristinamycin $II_B$ in the form of off-white crystals melting at around 146° C. (dec.).

$^1$H NMR spectrum (400 MHz, CDCl$_3$, δ in ppm): 0.96 (d, J=6.5 Hz: 3H); 1.01 (d, J=6.5 Hz: 3H); 1.09 (d, J=6.5 Hz: 3H); from 1.75 to 2.05 (mt: 5H); 1.90 (s: 3H); 2.15 (mt: 1H); 2.32 (mt: 1H); 2.77 (mt: 1H); 3.22 (dd, J=17 and 7 Hz: 1H); 3.44 (dd, J=17 and 7 Hz: 1H); 3.52 (mt: 1H); 3.83 (mt: 1H); 4.09 (mt: 1H); 4.37 (mt: 1H); 4.52 (mt: 1H); from 4.75 to 4.90 (mt: 2H); 4.79 (dd, J=10 and 1.5 Hz: 1H); 5.34 (d, J=9 Hz: 1H); 5.75 (mt: 1H); 5.82 (dd, J=17 and 1.5 Hz: 1H); 6.03 (mt: 1H); 6.22(d, J=16Hz: 1H);6.52(dd, J=17and 5Hz: 1H); 8.11 (s: 1H).

(16R)-16-deoxo-16-bromo-14-O-(tert-butyldiphenylsilyl)pristinamycin $II_B$ may be prepared in the following manner:

Carrying out the procedure in a manner similar to that described in Example 4, but starting with 5.25 g of tetra-n-butylammonium bromide in solution in 60 cm³ of dichloromethane, there are added, at 20° C., under an argon atmosphere, 2.5 g of (16S)-16-hydroxy-14-O-(tert-butyldiphenylsilyl)pristinamycin $II_B$ (prepared as described in Example 1) and then, slowly, 1.5 cm³ of diethylaminosulfur trifluoride. After stirring for 10 minutes under a treatment similar to that in Example 4, 4.6 g of a yellow solid are obtained, which solid is purified by flash chromatography [eluent: cyclohexane/ethyl acetate (6/4 by volume)]. 1.38 g of (16R)-16-deoxo-16-bromo-14-O-(tert-butyldiphenylsilyl)pristinamycin II$_B$ are obtained in the form of a white solid.

¹H NMR spectrum (400 MHz, CDCl₃, δ in ppm): 0.96 (d, J=6.5 Hz: 3H); 1.00 (d, J=6.5 Hz: 3H); 1.07 (s: 9H); 1.10 (d, J=6.5 Hz: 3H); 1.37 (s: 3H); from 1.70 to 2.05 (mt: 5H); 2.14 (mt: 1H); 2.31 (mt: 1H); 2.77 (mt: 1H); 3.12 (dd, J=17 and 5.5 Hz: 1H); 3.30 (dd, J=17 and 8 Hz: 1H); 3.45 (mt: 1H); 3.77 (mt: 1H); 4.03 (mt: 1H); 4.23 (mt: 1H); 4.55 (mt: 1H); from 4.75 to 4.85 (mt: 3H); 5.33 (d, J=9 Hz: 1H); 5.54 (mt: 1H); 5.82 (broad d, J=16 Hz: 1H); 6.00 (mt: 1H); 6.12 (d, J=16 Hz: 1H); 6.50 (dd, J=16 and 5 Hz: 1H); from 7.30 to 7.45 (mt: 6H); 7.63 (broad d, J=7 Hz: 2H); 7.69 (broad d, J=7 Hz: 2H); 8.08 (s: 1H).

EXAMPLE 6

(16R)-16-Deoxo-16-chloropristinamycin II$_B$

Carrying out the procedure in a manner similar to that described in Example 4, but starting with 1.4 g of (16R)-16-deoxo-16-chloro-14-O-(tert-butyldiphenylsilyl)-pristinamycin II$_B$ in solution in 35 cm³ of dichloromethane, 11 cm³ of triethylamine trihydrofluoride are added at 20° C. After stirring for 20 hours under reflux and a treatment similar to that in Example 4, an orange-colored solid is obtained which is purified by flash chromatography [eluent: dichloromethane/methanol (97/3 by volume)]. 1 g of a white solid is obtained to which 0.5 g obtained from an identical experiment is added. After recrystallization from 10 cm³ of acetonitrile, 1.12 g of (16R)-16-deoxo-16-chloropristinamycin II$_B$ are obtained in the form of white crystals melting at around 142° C. (dec.).

¹H NMR spectrum (400 MHz, CDCl₃, δ in ppm): 0.96 (d, J=6.5 Hz: 3H); 1.00 (d, J=6.5 Hz: 3H); 1.10 (d, J=6.5 Hz: 3H); from 1.75 to 2.05 (mt: 5H); 1.88 (s: 3H); from 2.10 to 2.25 (mt: 2H); 2.75 (mt: 1H); 3.10 (dd, J=17 and 7 Hz: 1H); 3.30 (dd, J=17 and 6.5 Hz: 1H); 3.53 (mt: 1H); 3.84 (mt: 1H); 4.06 (mt: 1H); 4.37 (mt: 1H); 4.49 (mt: 1H); from 4.75 to 4.90 (mt: 3H); 5.35 (d, J=9 Hz: 1H); 5.76 (mt: 1H); 5.83 (dd, J=17 and 2 Hz: 1H); 5.99 (mt: 1H); 6.22 (d, J=15.5 Hz: 1H); 6.51 (dd, J=17 and 5 Hz: 1H); 8.09 (s: 1H).

(16R)-16-deoxo-16-chloro-14-O-(tert-butyldiphenylsilyl) pristinamycin II$_B$ may be prepared in the following manner:

Carrying out the procedure in a manner similar to that described in Example 4, but starting with 7.27 g of tetra-n-butylammonium chloride in solution 50 m³ of dichloromethane, there are added, at 20° C., under an argon atmosphere, 4 g of (16S)-16-hydroxy-14-O-(tert-butyldiphenylsilyl)pristinamycin II$_B$ (prepared as described in Example 1) and then, dropwise, 2.44 cm³ of diethylaminosulfur trifluoride. After stirring for 10 minutes and a treatment similar to that in Example 4, 4.45 g of a yellow solid are obtained, which solid is purified by flash chromatography [eluent: cyclohexane/ethyl acetate (55/45 by volume)]. 0.51 g of (16R)-16-deoxo-16-chloro-14-O-(tert-butyldiphenylsilyl)pristinamycin II$_B$ is obtained in the form of a white solid.

¹H NMR spectrum (400 MHz, CDCl₃, δ in ppm): 0.96 (d, J=6.5 Hz: 3H); 1.00 (d, J=6.5 Hz: 3H); 1.07 (s: 9H); 1.10 (d, J=6.5 Hz: 3H); 1.33 (s: 3H); from 1.70 to 1.90 (mt: 4H); 1.96 (mt: 1H); from 2.05 to 2.25 (mt: 2H); 2.77 (mt: 1H); 2.98 (dd, J=17 and 5.5 Hz: 1H); 3.16 (dd, J=17 and 8 Hz: 1H); 3.45 (mt: 1H); 3.76 (mt: 1H); 4.03 (mt: 1H); 4.25 (mt: 1H); 4.55 (mt: 1H); from 4.75 to 4.85 (mt: 3H); 5.34 (d, J=9 Hz: 1H); 5.54 (mt: 1H); 5.82 (dd, J=16 and 2 Hz: 1H); 5.99 (mt: 1H); 6.11 (d, J=16 Hz: 1H); 6.50 (dd, J=16 and 5 Hz: 1H); from 7.30 to 7.45 (mt: 6H); 7.63 (dd, J=7 and 1.5 Hz: 2H); 7.68 (dd, J=7 and 1.5 Hz: 2H); 8.08 (s: 1H).

EXAMPLE 7

(16R)-16-Deoxo-16-iodopristinamycin II$_B$

Carrying out the procedure in a manner similar to that described in Example 4, but starting with 0.83 g of (16R)-16-deoxo-16-iodo-14-O-(tert-butyldiphenylsilyl)-pristinamycin II$_B$ in solution in 15 cm³ of dichloromethane, 6.2 cm³ of triethylamine trihydrofluoride are added at 20° C. After stirring for 23 hours under reflux and a treatment similar to that in Example 4, 0.9 g of an off-white solid is obtained, which solid is purified by flash chromatography [eluent: dichloromethane/methanol/acetonitrile (98/1/1 by volume)]. 0.41 g of a yellow solid is obtained, which solid is purified by high-performance liquid chromatography on a 5 μl KROMASIL)® C18 silica column (column diameter=2 cm, column length=25 cm), [eluent: water/acetonitrile gradient (80/20 to 60/40 by volume)]. 0.18 g of a white solid is obtained to which 0.12 g obtained from equivalent trials is added to give 0.3 g of (16R)-16-deoxo-16-iodopristinamycin II$_B$, in the form of a beige solid melting at around 140° C. (dec.).

¹H NMR spectrum (400 MHz, CDCl₃, δ in ppm): 0.96 (d, J=6.5 Hz: 3H); 1.01 (d, J=6.5 Hz: 3H); 1.09 (d, J=6.5 Hz: 3H); 1.67 (d, J=3 Hz: 1H); 1.73 (mt: 1H); from 1.80 to 2.05 (mt: 4H); 1.94 (s: 3H); 2.17 (mt: 1H); 2.36 (mt: 1H); 2.77 (mt: 1H); 3.31 (dd, J=17 and 7 Hz: 1H); from 3.45 to 3.60 (mt: 1H); 3.53 (dd, J=17 and 7 Hz: 1H); 3.85 (mt: 1H); 4.10 (mt: 1H); 4.32 (mt: 1H); 4.53 (mt: 1H); from 4.75 to 4.85 (mt: 3H); 5.31 (d, J=9 Hz: 1H); 5.76 (mt: 1H); 5.82 (dd, J=17 and 1.5 Hz: 1H); 6.00 (mt: 1H); 6.21 (d, J=16 Hz: 1H); 6.51 (dd, J=17 and 5 Hz: 1H); 8.11 (s: 1H).

(16R)-16-deoxo-16-iodo-14-O-(tert-butyldiphenylsilyl) pristinamycin II$_B$ may be prepared in the following manner:

Carrying out the procedure in a manner similar to that described in Example 4, but starting with 7.2 g of tetra-n-butylammonium iodide in a solution in 60 cm³ of dichloromethane, there are added, at 20° C., under an argon atmosphere, 3 g of (16S)-16-hydroxy-14-O-(tert-butyldiphenylsilyl)pristinamycin II$_B$ (prepared as described in Example 1) and then, dropwise at 0° C., 1.8 cm³ of diethylaminosulfur trifluoride. After stirring for 20 minutes at 0° C. and a similar treatment to that in Example 4, 10.5 g of an orange-colored oil is obtained, which oil is stirred for 15 minutes in 30 cm³ of a cyclohexane/ethyl acetate mixture (60/40). After filtration and concentrating the filtrate under reduced pressure (2.7 kPa), 5.5 g of a yellow solid are obtained, which solid is purified by flash chromatography [eluent: cyclohexane/ethyl acetate (60/40 by volume)]. 1.81 g of (16R)-16-deoxo-16-iodo-14-O-(tert-butyldiphenylsilyl)-pristinamycin pristinamycin II$_B$ are obtained in the form of a white solid melting at around 105° C. (dec.).

¹H NMR spectrum (400 MHz, CDCl₃, δ in ppm): 0.96 (d, J=6.5 Hz: 3H); 1.00 (d, J=6.5 Hz: 3H); 1.05 (s: 9H); 1.09 (d, J=6.5 Hz: 3H); 1.41 (s: 3H); from 1.70 to 1.95 (mt: 4H); 1.96 (mt: 1H); 2.14 (mt: 1H); 2.33 (mt: 1H); 2.77 (mt: 1H); 3.20 (dd, J=17 and 6 Hz: 1H); 3.38 (dd, J=17 and 8 Hz: 1H); 3.45 (mt: 1H); 3.79 (mt: 1H); 4.03 (mt: 1H); 4.17 (mt: 1H); 4.54 (mt: 1H); 4.71 (dt, J=9 and 3 Hz: 1H); 4.78 (dd, J=10 and 2.5 Hz: 1H); from 4.75 to 4.85 (mt: 1H); 5.30 (d, J=9 Hz:

1H); 5.55 (mt: 1H); 5.81 (dd, J=17 and 2 Hz: 1H); 5.99 (mt: 1H); 6.11 (d, J=16 Hz: 1H); 6.49 (dd, J=17 and 5 Hz: 1H); from 7.30 to 7.45 (mt: 6H); 7.63 (dd, J=7 and 1.5 Hz: 2H); 7.69 (dd, J=7 and 1.5 Hz: 2H); 8.08 (s: 1H).

EXAMPLE 8

(16R)-16-Deoxo-16-fluoropristinamycin $II_A$ 0.2 cm$^3$ of acetic acid and 0.6 g of tetra-n-butylammonium fluoride trihydrate are added, at 20° C., under an argon atmosphere, to 0.97 g of (16R)-16-deoxo-16-fluoro-14-O-(tert-butyldiphenylsilyl)pristinamycin $II_A$ in solution in 8 cm$^3$ of tetrahydrofuran. After stirring for 168 hours, the reaction mixture is poured over 50 cm$^3$ of a saturated aqueous sodium bicarbonate solution. The organic phase is decanted off and the aqeuous phase is extracted with 30 cm$^3$ of dichloromethane. The organic phases are combined, dried over magnesium sulfate, filtered and then concentrated to dryness under reduced pressure (2.7 kPa) to give a residue which is purified by flash chromatography [eluent: dichloromethane/methanol/acetonitrile (95/2.5/2.5 by volume)]. 0.38 g of a yellow solid is obtained to which 0.21 g obtained from an identical experiment is added. After stirring in ether, filtration and drying under reduced pressure (2.7 kPa) at 20° C., 0.58 g of (16R)-16-deoxo-16-fluoro-pristinamycin $II_A$ is obtained in the form of a light yellow solid melting at around 110° C. (dec.).

$^1$H NMR spectrum (400 MHz, CDCl$_3$, δ in ppm): 0.99 (mt: 6H); 1.14 (d, J=6.5 Hz: 3H) 1.77 (s: 3H); from 1.85 to 2.10 (mt: 2H); 2.28 (mt: 1H); from 2.65 to 2.90 (mt: 3H); 3.08 (mt: 1H); 3.25 (mt: 1H); 3.98 (broad d, J=17 Hz: 1H); from 4.10 to 4.25 (mt: 2H); 4.31 (mt: 1H); from 4.55 to 4.80 (mt: 2H); from. 4.90 to 5.00 (mt: 2H); 5.69 (mt: 1H); 5.96 (d, J=16 Hz: 1H); 5.99 (d, J=16 Hz: 1H); 6.17 (broad t, J=3 Hz: 1H); 6.61 (dd, J=16 and 7 Hz: 1H); 7.06 (mt: 1H); 7.93 (s: 1H).

(16R)-16-deoxo-16-fluoro-14-O-(tert-butyldiphenylsilyl) pristinamycin $II_A$ may be prepared in the following manner:

20.5 cm$^3$ of diethylaminosulfur trifluoride are slowly added, at 20° C., under an argon atmosphere, to 65 g of (16S)-16-hydroxy-14-O-(tert-butyldiphenylsilyl)pristinamycin $II_A$ in solution in 700 cm$^3$ of dichloromethane. After stirring for 3 hours, the reaction mixture is slowly poured over 1000 cm$^3$ of a saturated aqueous sodium bicarbonate solution. The organic phase is decanted off and the aqueous phase is extracted with twice 500 cm$^3$ of dichloromethane. The organic phases are combined and dried over magnesium sulfate, filtered and then concentrated to dryness under reduced pressure (2.7 kPa) to give 67.62 g of an orange-colored solid. After stirring this solid in pentane, filtration and drying under reduced pressure (2.7 kPa) at 20° C., 65.55 g of (16R)-16-deoxo-16-fluoro-14-O-(tert-butyldiphenylsilyl)pristinamycin $II_A$ are obtained in the form of an orange-yellow solid.

$^1$H NMR spectrum (400 MHz, CDCl$_3$, δ in ppm): from 0.95 to 1.05 (mt: 6H); 1.05 (s: 9H); 1.13 (d, J=6.5 Hz: 3H); 1.28 (s: 3H); from 1.80 to 2.10 (mt: 2H); from 2.10 to 2.30 (mt: 1H); from 2.65 to 2.85 (mt: 3H); from 2.90 to 3.15 (mt: 2H); from 3.95 to 4.10 (mt: 2H); 4.16 (mt: 1H); 4.28 (mt: 1H); from 4.40 to 4.60 (mt: 2H); 4.99 (dd, J=10 and 1.5 Hz: 1H); 5.05 (d, J=9 Hz: 1H); 5.50 (mt: 1H); 5.90 (d, J=16 Hz: 1H); 6.00 (broad d, J=17 Hz: 1H); 6.16 (t, J=3 Hz: 1H); 6.61 (dd, J=17 and 7 Hz: 1H); 7.02 (t, J=5.5 Hz: 1H); from 7.25 to 7.50 (mt: 6H); 7.58 (broad d, J=7 Hz: 2H); 7.67 (broad d, J=7 Hz: 2H); 7.89 (s: 1H).

(16S)-16-hydroxy-14-O-(tert-butyldiphenylsilyl)pristinamycin $II^A$ may be prepared in the following manner:

Carrying out the procedure in a manner similar to that described in Example 1, but starting with 10 g of (16S)-16-hydroxypristinamycin $II_A$ in solution in 100 cm$^3$ of dichloromethane, there are added, at 20° C., under an argon atmosphere, 13.2 cm$^3$ of diisopropylethylamine, 19.7 cm$^3$ of tert-butyldiphenylchlorosilane dropwise and 0.46 g of 4-dimethylaminopyridine. After stirring for 20 hours and a treatment similar to that in Example 1, 35 g of a brown oil are obtained, which oil is purified by flash chromatography [eluent: dichloromethane/methanol/acetonitrile (96/2/2 by volume)]. 10.5 g of (16S)-16-hydroxy-14-O-(tert-butyldiphenylsilyl)pristinamycin $II_A$ are obtained in the form of a beige solid.

$^1$H NMR spectrum (400 MHz, CDCl$_3$, δ in ppm): from 0.90 to 1.05 (mt: 6H); from 1.05 to 1.15 (mt: 15H); from 1.90 to 2.05 (mt: 3H); 2.54 (mt: 1H); 2.66 (mt: 1H); 2.76 (mt: 1H); 2.82 (dd, J=16 and 11 Hz: 1H); 3.11 (dd, J=16 and 3 Hz: 1H); 3.28 (mt: 1H); 3.83 (broad s: 1H); from 4.00 to 4.15 (mt: 2H); 4.50 (mt: 1H); 4.57 (mt: 1H); 4.81 (mt: 1H); 4.94 (dd, J=10 and 2 Hz: 1H); 5.38 (mt: 1H); 5.63 (d, J=9Hz: 1H);5.88(dd, J=16and 1.5Hz: 1H); 5.94(d, J=16Hz: 1H); 6.01 (t, J=3 Hz: 1H); 6.34 (mt: 1H); 6.47 (dd, J=16 and 5 Hz: 1H); from 7.25 to 7:50 (mt: 6H); 7.62 (dd, J=7 and 1.5 Hz: 2H); 7.68 (dd, J=7 and 1.5 Hz: 2H); 8.06 (s: 1H).

(16S)-16-Hydroxypristinamycin $II_A$ may be prepared according to F. Le Goffic et al.; Eur. J. Med.—Chimica Therapeutica; January–February,—16(1), 69–72 (1981).

EXAMPLE 9

(16R)-16-Deoxo-16-fluoro-14-O-[4-(morpholin4-ylmethyl)benzoyl]pristinamycin $II_B$ methanesulfonate 2 cm$^3$ of a 0.1 N ethanolic solution of methanesulfonic acid is added, at 20° C., to 0.15 g of (16R)-16-deoxo-16-fluoro-14-O-[4-(morpholin4-ylmethyl)benzoyl]-pristinamycin $II_B$ in solution in 5 cm$^3$ of methanol. After stirring for 10 minutes, the reaction mixture is concentrated to dryness under reduced pressure (2.7 kPa) to give a white residue which is stirred in 10 cm$^3$ of ether. After filtration, rinsing of the solid with 10 cm$^3$ of diethyl ether and drying under reduced pressure (2.7 kPa) at 20° C., 0.15 g of (16R)-16-deoxo-16-fluoro-14-O-[4-(morpholin4-ylmethyl)benzoyl]-pristinamycin $II_B$ methanesulfonate is obtained in the form of a white solid melting at around 150° C. (dec.).

$^1$H NMR spectrum (400 MHz, (CD$_3$)$_2$SO d6, δ in ppm): 0.85 (d, J=6:5 Hz: 3H); 0.95 (d, J=6.5 Hz: 3H); 1.05 (d, J=6.5 Hz: 3H); 1.54 (mt: 1H); from 1.75 to 2.00 (mt: 3H); 1.86 (s: 3H); from 2.05 to 2.25 (mt: 2H); from 2.30 to 2.45 (mt: 1H); 2.32 (s: 3H); 2.78 (mt: 1H); from 3.05 to 3.45 (mt: 6H); from 3.55 to 3.70 (mt: 3H); 3.72 (mt: 1H); 3.84 (mt: 1H); from 3.90 to 4.05 (mt: 3H); 4.47 (unresolved complex: 2H); from 4.70 to 4.80 (mt: 2H); 5.18 (decoupled doublet, $J_{HF}$=48 Hz: 1H); 5.55 (d, J=9.5 Hz: 1H); 5.66 (mt: 1H); 5.81 (broad d, J=16 Hz: 1H); 6.00 (mt: 1H); 6.21 (d, J=16 Hz: 1H); 6.64 (dd, J=16 and 5 Hz: 1H); 7.68 (broad d, J=7.5 Hz: 2H); 8.08 (broad d, J=7.5 Hz: 2H); 8.16 (mt: 1H); 8.55 (s: 1H); 9.95 (unresolved complex: 1H).

(16R)-16-Deoxo-16-fluoro-14-O-[4-(morpholin-4-ylmethyl)benzoyl ] pristinamycin $II_B$ may be prepared in the following manner:

0.44 g of sodium iodide and 0.5 cm$^3$ of morpholine are added, at 20° C., to 2 g of (16R)-16-deoxo-16-fluoro-14-O-[4-(chloromethyl)benzoyl]pristinamycin $II_B$ in solution in 50 cm³ of tetrahydrofuran. After stirring for 17 hours under reflux, the reaction mixture is poured over 50 cm³ of water and then extracted with twice 50 cm³ of dichloromethane. The organic phases are combined, washed with twice 100 cm³ of water, dried over magnesium sulfate, filtered and concentrated to dryness under reduced pressure (2.7 kPa) to give 2.5 g of a residue which is purified by flash chromatography [eluent: dichloromethane/methanol gradient (100/0, 99/1 and 98/2 by volume)]. A solid is obtained which is stirred in pentane, filtered and dried (90 Pa) at 30° C. to give 1.69 g of (16R)-16-deoxo-16-fluoro-14-O-[4-(morpholin4-yl-methyl)benzoyl]pristinamycin $II_B$, in the form of an off-white solid melting around 120° C. (dec.).

$^1$H NMR spectrum (400 MHz, CDCl₃, δ in ppm): 0.96 (d, J=6.5 Hz: 3H); 1.01 (d, J=6.5 Hz: 3H); 1.10 (d, J=6.5 Hz: 3H); from 1.75 to 2.05 (mt: 5H); 1.95 (s: 3H); 2.16 (mt: 1H), from 2.30 to 2.50 (mt: 1H); 2.44 (mt: 4H); 2.76 (mt: 1H); 3.05 (dt, J=17 and 6 Hz: 1H); 3.29 (mt: 1H); 3.49 (mt: 1H); 3.55 (s: 2H); 3.71 (mt: 4H); 3.89 (mt: 1H); 4.09 (mt: 1H); 4.52 (mt: 1H); 4.79 (broad d, J=10 Hz: 1H); 4.83 (dd, J=9 and 3 Hz: 1H); 5.18 (decoupled doublet, $J_{HF}$=48 Hz: 1H); 5.45 (d, J=9.5 Hz: 1H); from 5.70 to 5.85 (mt: 1H); 5.82 (broad d, J=17 Hz: 1H); 5.94 (mt: 1H); 6.06 (dt, J=9.5 and 5 Hz: 1H); 6.22 (d, J=16 Hz: 1H); 6.52 (dd, J=17 and 5 Hz: 1H); 7.41 (d, J=8 Hz: 2H); 7.98 (d, J=8Hz: 2H); 8.14 (s: 1H).

(16R)-16-deoxo-16-fluoro-14-O-[4-(chloromethyl)benzoyl]pristinamycin $II_B$ may be prepared in the following manner:

2.84 g of 4-(chloromethyl)benzoyl chloride and 0.095 g of 4-dimethylaminopyridine are added, at 10° C., to 5.32 g of (16R)-16-deoxo-16-fluoropristinamycin $II_B$ (prepared as described in Example 1) in solution in 150 cm³ of dichloromethane and 2.1 cm³ of triethylamine. After stirring for 20 hours at 20° C., the reaction mixture is successively washed with 50 cm³ of water, 50 cm³ of a 5% aqueous sodium bicarbonate solution, 30 cm³ of water and 30 cm³ of a saturated aqueous sodium chloride solution. The organic phase is dried over magnesium sulfate, filtered and then concentrated to dryness under reduced pressure (2.7 kPa) to give 7.2 g of a beige residue which is purified by flash chromatography [eluent: dichloromethane/methanol/acetonitrile gradient (99/0.5/0.5 and 98/1/1 by volume)]. 4.5 g of (16R)-16-deoxo-16-fluoro-14-O-[4-(chloromethyl)benzoyl]pristinamycin $II_B$ are obtained in the form of a light yellow solid.

$^1$H NMR spectrum (400 MHz, CDCl₃, δ in ppm): 0.96 (d, J=6.5 Hz: 3H); 1.01 (d, J=6.5 Hz: 3H); 1.10 (d, J=6.5 Hz: 3H); from 1.75 to 2.05 (mt: 5H); 1.95 (s: 3H); 2.16 (mt: 1H); 2.40 (mt: 1H); 2.76 (mt: 1H); 3.04 (dt, J=17 and 6 Hz: 1H); 3.29 (mt: 1H); 3.49 (mt: 1H); 3.88 (mt: 1H); 4.09 (mt: 1H); 4.53 (mt: 1H); 4.62 (s: 2H); 4.78 (dd, J=10 and 2 Hz: 1H); 4.83 (dd, J=9 and 3 Hz: 1H); 5,18 (decoupled doublet, $J_{HF}$=48 Hz: 1H); 5.44 (d, J=9.5 Hz: 1H); from 5.75 to 5.85 (mt: 1H); 5.82 (dd, J=17 and 2 Hz: 1H); 5.94 (mt: 1H); 6.06 (dt, J=9.5 and 5 Hz: 1H); 6.22 (d, J=16Hz: 1H);6.52(dd, J=17and 5 Hz: 1H); 7.47(d, J=8Hz: 2H);8.02(d, J=8 Hz: 2H); 8.14 (s: 1H).

EXAMPLE 10

(16R)-16-Deoxo-16-fluoro-14-O-[4-(imidazol-1-ylmethyl)benzoyl]pristinamycin $II_B$ Carrying out the procedure in a manner similar to that described in Example 9, but starting with 0.499 g of (16R)-16-deoxo-16-fluoro-14-O-[4-(chloromethyl)benzoyl]-pristinamycin $II_B$ (prepared as described in Example 9) in solution in 30 cm³ of tetrahydrofuran, 0.11 g of sodium iodide and 0.099 g of imidazole are added at 20° C. After stirring for 17 hours under reflux and a treatment similar to that in Example 9, 0.5 g of a yellow solid is obtained, which solid is purified by flash chromatography [eluent: dichloromethane/methanol (97/3 by volume)]. A solid is obtained which is stirred in ether, filtered and dried (90 Pa) at 20° C., to give 0.289 g of (16R)-16-deoxo-16-fluoro-14-O-[4-(imidazol-1-ylmethyl)benzoyl]pristinamycin $II_B$, in the form of a yellow solid melting at around 136° C. (dec.).

$^1$H NMR spectrum (400 MHz, CDCl₃, δ in ppm): 0.96 (d, J=6.5 Hz: 3H); 1.01 (d, J=6.5 Hz: 3H); 1.10 (d, J=6.5 Hz: 3H); from 1.75 to 2.05 (mt: 5H); 1.95 (s: 3H); 2.16 (mt: 1H); 2.39 (mt: 1H); 2.76 (mt: 1H); 3.04 (td, J=17 and 6 Hz: 1H); 3.28 (mt: 1H); 3.49 (mt: 1H); 3.87 (mt: 1H); 4.08 (mt: 1H); 4.53 (mt: 1H); 4.78 (broad d, J=10 Hz: 1H); 4.83 (dd, J=9 and 3 Hz: 1H); 5.17 (decoupled doublet, $J_{HF}$=48 Hz: 1H); 5.19 (s: 2H); 5.43 (d, J=9 Hz: 1H); 5.78 (mt: 1H); 5.82 (dd, J=17 and 1.5 Hz: 1H); 5.94 (mt: 1H); 6.05 (mt: 1H); 6.22 (d, J=16 Hz: 1H); 6.52(dd, J=17 and 5 Hz: 1H); 6.90 (s: 1H); 7.13 (s: 1H); 7.20 (d, J=8 Hz: 2H); 7.58 (s: 1H); 8.01 (d, J=8 Hz: 2H); 8.14 (s: 1H).

EXAMPLE 11

(16R)-16-Deoxo-16-fluoro-14-O-[4-(4-methylpiperazin-1-ylmethyl)benzoyl]-pristinamycin $II_B$ Carrying out the procedure in a manner similar to that described in Example 9, but starting with 2 g of (16R)-16-deoxo-16-fluoro-14-O-[4-(chloromethyl)benzoyl]-pristinamycin $II_B$ (prepared as described in Example 9) in solution in 90 cm³ of tetrahydrofuran, 0.44 g of sodium iodide and 0.65 cm³ of methylpiperazine in solution in 10 cm³ of tetrahydrofuran are added at 20° C. After stirring for 20 hours under reflux and a treatment similar to that in Example 9, 2.4 g of a residue are obtained, which residue is purified by flash chromatography [eluent: dichloromethane/methanol (99/1 by volume)]. A solid is obtained which is stirred in 15 cm³ of ether, filtered and dried (90 Pa) at 20° C. to give 1 g of (16R)-16-deoxo-16-fluoro-14-O-[4-(4-methylpiperazin-1-ylmethyl)benzoyl]prostinamycin $II_B$, in the form of a pale yellow solid melting at around 160° C. (dec.).

$^1$H NMR spectrum (400 MHz, CDCl₃, δ in ppm): 0.96 (d, J=6.5 Hz: 3H); 1.01 (d, J=6.5 Hz: 3H); 1.10 (d, J=6.5 Hz: 3H); from 1.75 to 2.25 (mt: 6H); 1.95 (s: 3H); from 2.30 to 2.50 (mt: 1H); 2.40 (s: 3H); 2.62 (unresolved complex: 8H); 2.76 (mt: 1H); 3.04 (dt, J=17 and 6 Hz: 1H); 3.29 (mt: 1H); 3.49 (mt: 1H); 3.59 (s: 2H); 3.88 (mt: 1H); 4.08 (mt: 1H); 4.52 (mt: 1H); 4.79 (broad d, J=10 Hz: 1H); 4.83 (dd, J=9 and 3 Hz: 1H); 5.18 (decoupled doublet, $J_{HF}$=48 Hz: 1H); 5.44 (d, J=9.5 Hz: 1H); from 5.70 to 5.85 (mt: 1H); 5.82 (dd, J=17 and 1.5 Hz: 1H); 5.95 (mt: 1H); 6.05 (dt, J=9.5 and 6 Hz: 1H); 6.22 (d, J=16 Hz: 1H); 6.52 (dd, J=17 and 5 Hz: 1H); 7.40 (d, J=8.5 Hz: 2H); 7.97 (d, J=8.5 Hz: 2H); 8.14 (s: 1H).

EXAMPLE 12

(16R)-16-Deoxo-16-fluoro-14-O-[4-(diethylaminomethyl)benzoyl]pristinamycin $II_B$ Carrying out the procedure in a manner similar to that described in Example 9, but starting with 0.55 g of (16R)-16-deoxo-16-fluoro-14-O-[4-(chloromethyl)benzoyl]-pristinamycin $II_B$ (prepared as described in Example 9) in solution in 30 cm³ of tetrahydrofuran, 0.12 g of sodium iodide and 0.17 cm³ of diethylamine are added at 20° C. After stirring for 15.5 hours under reflux and a treatment similar to that in Example 9, a residue is obtained which is purified by flash chromatography [eluent: dichloromethane/methanol (95/5 by volume)]. A solid is obtained which is stirred in 20 cm³ of pentane, filtered and dried (90 Pa) at 20° C., to give 0.14 g of (16R)-16-deoxo-16-fluoro-14-O-[4-(diethylaminomethyl)benzoyl]pristinamycin $II_B$ in the form of a pale yellow solid melting at around 150° C. (dec.).

¹H NMR spectrum (400 MHz, CDCl₃, δ in ppm): 0.96 (d, J=6.5 Hz: 3H); 1.03 .(mt: 9H) 1.09 (d, J=6.5 Hz: 3H); from 1.75 to 2.05 (mt: 5H); 1.95 (s: 3H); 2.16 (mt: 1H); 2.40 (mt: 1H); 2.52 (q, J=7 Hz: 4H); 2.77 (mt: 1H); 3.05 (td, J=17 and 6 Hz: 1H); 3.28 (mt: 1H); 3.48 (mt: 1H); 3.61 (s: 2H); 3.89 (mt: 1H); 4.09 (mt: 1H); 4.53 (mt: 1H); 4.79 (broad d, J=10 Hz: 1H); 4.82 (dd, J=9 and 3 Hz: 1H); 5.17 (decoupled doublet, $J_{HF}$=48 Hz: 1H); 5.44 (d, J=9 Hz: 1H); 5.77 (mt: 1H); 5.82 (dd, J=17 and 1.5 Hz: 1H); 5.92 (mt: 1H); 6.05 (mt: 1H); 6.21 (d, J=6 Hz: 1H); 6.50 (dd, J=16 and 5 Hz: 1H); 7.42 (d, J=8 Hz: 2H); 7.96(d, J=8 Hz: 2H); 8.14 (s: 1H).

EXAMPLE 13

(16R)-16-Deoxo-16-fluoro-14-O-{4-[((2S)-2-hydroxymethyl)pyrrolidin-1-ylmethyl]-benzoyl}prostinamycin $II_B$ Carrying out the procedure in a manner similar to that described in Example 9, but starting with 1 g of (16R)-16-deoxo-16-fluoro-14-O-[4-(chloromethyl)benzoyl]-pristinamycin $II_B$ (prepared as described in Example 9) in solution in 45 cm³ of tetrahydrofuran, 0.22 g of sodium iodide and 0.29 cm³ of L-prolinol in solution in 5 cm³ of tetrahydrofuran are added at 20° C. After stirring for 12 hours under reflux and a treatment similar to that in Example 9, 1.25 g of a residue is obtained which is purified by flash chromatography [eluent: dichloromethane/methanol (98/2 by volume)]. A solid is obtained which is stirred in 10 cm³ of ether, filtered and dried (90 Pa) at 20° C., to give 0.4 g of (16R)-16-deoxo-16-fluoro-14-O-{44-[((2S)-2-hydroxymethyl)pyrrolidin-1-ylmethyl]benzoyl}prostinamycin $II_B$, in the form of a white solid melting at around 158° C. (dec.).

¹H NMR spectrum (400 MHz, CDCl₃, δ in ppm): 0.96 (d, J=6.5 Hz: 3H); 1.01 (d, J=6.5 Hz: 3H); 1.10 (d, J=6.5 Hz: 3H); from 1.55 to 2.05 (mt: 8H); 1.96 (s: 3H); 2.17 (mt: 1H); 2.29(mt: 1H); 2.41 (mt: 1H); 2.77 (mt: 2H); 2.96 (mt: 1H); 3.05 (td, J=17 and 6 Hz: 1H); 3.29 (mt: 1H); from 3.40 to 3.55 (mt: 3H ); 3.66 (dd, J=11 and 4 Hz: 1H); 3.88 (mt: 1H); 4.02 (d, J=13 Hz: 1H); 4.09 (mt: 1H); 4.53 (mt: 1H); 4.79 (dd, J=10 and 2 Hz: 1H); 4.83 (dd, J=9 and 3 Hz: 1H); 5.18 (decoupled doublet, $J_{HF}$=48 Hz: 1H); 5.45 (d, J=9.5 Hz: 1H); 5.78 (mt: 1H); 5.82 (dd, J=16 and 2 Hz: 1H); 5.95 (mt: 1H); 6.05 (mt: 1H); 6.22 (d, J=16 Hz: 1H); 6.52 (dd, J=16 and 5 Hz: 1H); 7.38 (d, J=8Hz: 2H); 7.98 (d, J=8 Hz: 2H); 8.14 (s: 1H).

EXAMPLE 14

(16R)-16-Deoxo-16-fluoro-14-O-[4-(2-picolylaminomethyl)benzoyl]pristinamycin $II_B$ Carrying out the procedure in a manner similar to that described in Example 9, but starting with 2 g of (16R)-16-deoxo-16-fluoro-14-O-[4-(chloromethyl)benzoyl]-pristinamycin $II_B$ (prepared as described in Example 9) in solution in 20 cm³ of tetrahydrofuran, 0.44 g of sodium iodide and 1.2 cm³ of 2-(aminomethyl)pyridine are added at 20° C. After stirring for 17 hours under reflux and a treatment similar to that in Example 9, 2.1 g of a dark yellow solid are obtained, which solid is purified by two successive flash chromatographies [eluent: respectively dichloromethanel-methanol/acetonitrile (92/4/4 and 95/2.5/2.5, by volume)]. A solid is obtained which is stirred in ether, filtered and dried (90 Pa) at 20° C., to give 1.59 g of (16R)-16-deoxo-16-fluoro-14-O-[4-(2-picolylaminomethyl)benzoyl]pristinamycin $II_B$, in the form of a white solid melting at around 106° C. (dec.).

¹H NMR spectrum (400 MHz, CDCl₃, δ in ppm): 0.96 (d, J=6.5 Hz: 3H); 1.01 (d, J=6.5 Hz: 3H); 1.10 (d, J=6.5 Hz: 3H); from 1.75 to 2.05 (mt: 5H); 1.95 (s: 3H); 2.16 (mt: 1H); 2.40 (mt: 1H); 2.77 (mt: 1H); 3.05 (dt, J=17 and 6 Hz: 1H); 3.29 (mt: 1H); 3.49 (mt: 1H); 3.90 (mt: 1H); 3.92 (s: 2H); 3.93 (s: 2H); 4.10 (mt: 1H); 4.53 (mt: 1H); 4.79 (dd, J=10 and 2 Hz: 1H); 4.83 (dd, J=9 and 3.5 Hz: 1H); 5.18 (decoupled doublet, $J_{HF}$=48 Hz: 1H); 5.45 (d, J=9 Hz: 1H); 5.79 (mt: 1H); 5.82 (dd, J=16 and 2 Hz: 1H); 5.92 (mt: 1H); 6.06 (mt: 1H); 6.22 (d, J=16 Hz: 1H); 6.51 (dd, J=16 and 5 Hz: 1H); 7.18 (dd, J=8 and 5 Hz: 1H); 7.30 (d, J=8 Hz: 1H); 7.45 (d, J=9 Hz: 2H); 7.65 (dt, J=8 and 2 Hz: 1H); 7.99 (d, J=8 Hz: 2H); 8.14 (s: 1H); 8.58 (broad d, J=5 Hz: 1H).

EXAMPLE 15

(16R)-16-Deoxo-16-fluoro-14-O-[4-(pyrrolidin-1-yl)benzoyl]pristinamycin $II_B$

Carrying out the procedure in a manner similar to that described in Example 9, but starting with 1 g of (16R)-16-deoxo-16-fluoro-14-O-[4-(chloromethyl)benzoyl]-pristinamycin $II_B$ (prepared as described in Example 9) in solution in 50 cm³ of tetrahydrofuran, 0.22 g of sodium iodide and 0.24 cm³ of pyrrolidine are added at 20° C. After stirring for 7 hours under reflux and a treatment similar to that in Example 9, a residue is obtained which is purified by flash chromatography [eluent: dichloromethane/methanol (99/1 by volume)]. After stirring in 10 cm³ of pentane, filtration and drying (90 Pa) at 20° C., 0.4 g of (16R)-16-deoxo-16-fluoro-14-O-[4-(pyrrolidin-1-yl)benzoyl]-pristinamycin $II_B$ is thus obtained in the form of a yellow solid melting at around 170° C. (dec.).

¹H NMR spectrum (400 MHz, CDCl₃, δ in ppm): 0.96 (d, J=6.5 Hz: 3H); 1.01 (d, J=6.5 Hz: 3H); 1.10 (d, J=6.5 Hz: 3H); from 1.70 to 2.05 (mt: 5H); 1.81 (mt: 4H); 1.95 (s: 3H); 2.16 (mt: 1H); 2.40 (mt: 1H); 2.53 (mt: 4H); 2.76 (mt: 1H); 3.04 (td, J=17 and 6 Hz: 1H); 3.28 (mt: 1H); 3.48 (mt: 1H); 3.68 (s: 2H); 3.88 (mt: 1H); 4.09 (mt: 1H); 4.53 (mt: 1H); 4.79 (dd, J=10 and 1 Hz: 1H); 4.83 (dd, J=9 and 3 Hz: 1H); 5.17 (decoupled doublet, $J_{HF}$=48 Hz: 1H); 5.45 (d, J=9.5 Hz: 1H); 5.77 (mt: 1H); 5.81 (dd, J=17 and 1.5 Hz: 1H); 5.95 (mt: 1H); 6.05 (mt: 1H); 6.22 (d, J=16 Hz: 1H); 6.51 (dd, J=17 and 5 Hz: 1H); 7.42 (d, J=8 Hz: 2H); 7.97 (d, J=8Hz: 2H); 8.14(s: 1H).

EXAMPLE 16

(16R)-16-Deoxo-16-fluoro-14-O-[4-(piperidin-1-yl)benzoyl]pristinamycin $II_B$

Carrying out the procedure in a manner similar to that described in Example 9, but starting with 0.75 g of (16R)-16-deoxo-16-fluoro-14-O-[14-(chloromethyl)benzoyl]-pristinamycin $II_B$ (prepared as described in Example 9) in solution in 20 cm3 of tetrahydrofuran, 0.16 g of sodium iodide and 0.22 cm³ of piperidine are added at 20° C. After stirring for 15 hours at 66° C. and a treatment similar to that in Example 9, 1 g of a yellow solid is obtained, which solid is purified by flash chromatography [eluent: dichloromethane/methanol (97/3 by volume)]. After stirring in diethyl ether and then in pentane, filtration and drying (90 Pa) at 20° C., 0.33 g of (16R)-16-deoxo-16-fluoro-14-O-[4-(piperidin-1-yl)benzoyl]pristinamycin $II_B$ is thus obtained in the form of a white solid melting at around 110° C. (dec.).

$^1$H NMR spectrum (400 MHz, $CDCl_3$, δ in ppm):0.96 (d, J=6.5 Hz: 3H); 1.01 (d, J=6.5 Hz: 3H); 1.10 (d, J=6.5 Hz: 3H); from 1.35 to 1.70 (mt: 6H); from 1.75 to 2.05 (mt: 5H); 1.95 (s: 3H); 2.16 (mt: 1H); from 2.30 to 2.50 (mt: 5H); 2.76 (mt: 1H); 3.05 (td, J=17 and 6 Hz: 1H); 3.29 (mt: 1H); 3.49 (mt: 1H); 3.52 (s: 2H); 3.89 (mt: 1H); 4.09 (mt: 1H); 4.53 (mt: 1H); 4.79 (dd, J=10 and 1.5 Hz: 1H); 4.83 (dd, J=9 and 3 Hz: 1H); 5.18 (decoupled doublet, $J_{HF}$=48 Hz: 1H); 5.45 (d, J=9.5 Hz: 1H); 5.77 (mt: 1H); 5.82 (dd, J=16 and 2 Hz: 1H); 5.93 (mt: 1H); 6.05 (mt: 1H); 6.22 (d, J=16 Hz: 1H); 6.51 (dd, J=16 and 5 Hz: 1H); 7.40 (d, J=8 Hz: 2H); 7.97 (d, J=8 Hz: 2H); 8.14 (s: 1H).

EXAMPLE 17

(16R)-16-Deoxo-16-fluoro-14-O-{4-[(2-hydroxyethyl)aminomethyl]benzoyl}-pristinamycin $II_B$ Carrying out the procedure in a manner similar to that described in Example 9, but starting with 0.8 g of (16R)-16-deoxo-16-fluoro-14-O-[4-(chloromethyl)benzoyl]-pristinamycin $II_B$ (prepared as described in Example 9) in solution in 20 $cm^3$ of tetrahydrofuran, 0.17 g of sodium iodide and 0.14 $cm^3$ of ethanolamine and, after stirring for 16 hours under reflux and a treatment similar to that in Example 9, 0.8 g of a beige solid is obtained, which solid is purified by flash chromatography [eluent: dichloromethane/methanol gradient (95/5 and 90/10 by volume)]. After stirring in ether, filtration and drying (90 Pa), 0.36 g of a white solid is obtained, which solid is purified by high-performance liquid chromatography on a 5 μm Hypersil® column (column diameter=2 cm, column height=25 cm) [eluent: dichloromethane/methanol gradient (97/3 by volume)]. 0.129 g of (16R)-16-deoxo-16-fluoro-14-O-{4-[(2-hydroxyethyl)aminomethyl]benzoyl}pristinamycin $II_B$ is obtained in the form of a white solid melting at around 194° C. (dec.).

$^1$H NMR spectrum (400 MHz, $CDCl_3$, δ in ppm): 0.96 (d, J=6.5 Hz: 3H); 1.00 (d, J=6.5 Hz: 3H); 1.09 (d, J=6.5 Hz: 3H); from 1.70 to 2.05 (mt: 5H); 1.95 (s: 3H); 2.16 (mt: 1H); 2.39 (mt: 1H); 2.76 (mt: 1H); 2.81 (t, J=5.5 Hz: 2H); 3.04 (td, J=17 and 6 Hz: 1H); 3.28 (mt: 1H); 3.48 (mt: 1H); 3.67 (t, J=5.5 Hz: 2H ); from 3.85 to 3.95 (mt: 1H); 3.88 (s: 2H); 4.09 (mt: 1H); 4.52 (mt: 1H); 4.78 (broad d, J=10 Hz: 1H); 4.82 (dd, J=9 and 3 Hz: 1H); 5.17 (decoupled doublet, $J_{HF}$=48 Hz: 1H); 5.44 (d, J=9.5 Hz: 1H); 5.78 (mt: 1H); 5.81 (broad d, J=16 Hz: 1H); 5.93 (mt: 1H); 6.05 (mt: 1H); 6.22 (d, J=16 Hz: 1H); 6.51 (dd, J=16 and 5 Hz: 1H); 7.40 (d, J=8 Hz: 2H); 7.99 (d, J=8 Hz: 2H); 8.13 (s: 1H).

EXAMPLE 18

(16R)-16-Deoxo-16-fluoro-14-O-{4-[(2-diethylamino)ethylthiomethyl]benzoyl }-pristinamycin $II_B$ 0.82 $cm^3$ of a butyllithium solution (2.5 M in hexane) is added, at 0° C., to 0.46 $cm^3$ of 2-diethylaminoethanethiol in solution in 10 $cm^3$ of tetrahydrofuran. After stirring for 15 minutes, 1.4 g of (16R)-16-deoxo-16-fluoro-14-O-[4-(chloromethyl)benzoyl]-pristinamycin $II_B$ (prepared as described in Example 9) in solution in 15 $cm^3$ of tetrahydrofuran are added dropwise over 15 minutes. After stirring for 6.5 hours at 0° C. and for 15 hours at 20° C., a solution is added, dropwise, which has been prepared beforehand as above but from 0.153 $cm^3$ of 2-diethylaminoethananethiol and 0.205 $cm^3$ of a butyllithium solution (2.5 M in hexane) in 0.5 $cm^3$ of tetrahydrofuran. After stirring for 3.5 hours at 20° C., the reaction mixture is concentrated to dryness under reduced pressure (2.7 kPa) to give a residue which is taken up in 20 $cm^3$ of dichloromethane. This solution is washed with 50 $cm^3$ of water and then separated after settling. The aqueous phase is extracted with 20 $cm^3$ of dichloromethane. The organic phases are combined, washed with twice 70 $cm^3$ of water, dried over magnesium sulfate, filtered and concentrated to dryness under reduced pressure (2.7 kPa) to give 1.6 g of a yellow solid which is purified by flash chromatography [eluent: dichloromethane/methanol/acetonitrile (92/4/4 by volume)]. After stirring in pentane, filtration and drying (2.7 kPa) at 20° C., 0.926 g of (16R)-16-deoxo-16-fluoro-14-O-{4-[(2-diethylamino)ethylthiomethyl]benzoyl) pristinamycin $II_B$ is thus obtained in the form of a beige solid melting at around 84° C. (dec.).

$^1$H NMR spectrum (400 MHz, $CDCl_3$, δ in ppm): from 0.90 to 1.05 (mt: 12H); 1.10 (d, J=6.5 Hz: 3H); from 1.75 to 2.05 (mt: 5H); 1.96 (s: 3H); 2.16 (mt: 1H); 2.40 (mt: 1H); 2.50 (mt: 6H); 2.62 (mt: 2H); 2.76 (mt: 1H); 3.05 (dt, J=17 and 6 Hz: 3.29 (mt: 1H); 3.49 (mt: 1H); 3.77 (s: 2H); 3.89 (mt: 1H); 4.09 (mt: 1H); 4.53 (mt: 1H); 4.78 (dd, J=10 and 1.5 Hz: 1H); 4.83 (dd, J=9 and 3 Hz: 1H); 5.17 (decoupled doublet, $J_{HF}$=48 Hz: 1H); 5.45 (d, J=9 Hz: 1H); 5.78 (mt: 1H); 5.82 (dd, J=17 and 1.5 Hz: 1H); 5.92 (mt: 1H); 6.05 (mt: 1H); 6.22 (d, J=16 Hz: 1H); 6.52 (dd, J=17 and 5 Hz: 1H); 7.40 (d, J=8.5 Hz: 2H); 7.97 (d, J=8.5 Hz: 2H); 8.14 (s: 1H).

EXAMPLE 19

(16R)-16-Deoxo-16-fluoro-14-O-[4-(carboxymethylthiomethyl)benzoyl]pristinamycin $II_B$ 4.64 $cm^3$ of a butyllithium solution (2.5 M in hexane) are added, at 0° C., to 0.4 $cm^3$ of mercaptoacetic acid in solution in 10 $cm^3$ of tetrahydrofuran. After stirring for 15 minutes, the temperature of the reaction mixture is reduced to −50° C. and 2 g of (16R)-16-deoxo-16-fluoro-14-O-[4-(chloromethyl)benzoyl]pristinamycin $II_B$ (prepared as described in Example 9) in solution in 10 $cm^3$ of tetrahydrofuran are slowly added dropwise. After stirring for 3 hours at −50° C. and for 15 hours at 20° C., the temperature of the reaction mixture is again reduced to −50° C. and a solution is added, dropwise, which has been previously prepared as above at −50° C., but from 0.2 $cm^3$ of mercaptoacetic acid and 2.32 $cm^3$ of a butyllithium solution (2.5 M in hexane) in 5 $cm^3$ of tetrahydrofuran. After stirring for 5 hours at −50° C., the reaction mixture is poured over 100 $cm^3$ of water and the pH is adjusted to 3–4 by addition of a 0.1 N aqueous hydrochloric acid solution. After addition of 20 $cm^3$ of dichloromethane and 20 $cm^3$ of a saturated aqueous sodium chloride solution, the organic phase is decanted off and the aqueous phase is extracted with 20 $cm^3$ of dichloromethane. The organic phases are combined, dried over magnesium sulfate, filtered and concentrated to dryness under reduced pressure (2.7 kPa) to give 2.1 g of a yellow solid which is purified by flash chromatography [eluent: dichloromethane/ methanol/acetonitrile (90/5/5 by volume)]. After stirring in ether, filtration and drying (90 Pa) at 20° C., 0.21 g of (16R)-16-deoxo-16-fluoro-14-O-[4-(carboxymethylthiomethyl)benzoyl]-pristinamycin II$_B$ is thus obtained in the form of a yellow solid melting at around 142° C. (dec.).

$^1$H NMR spectrum (400 MHz, CDCl$_3$, δ in ppm): 0.96 (d, J=6.5 Hz: 3H); 1.00 (d, J=6.5 Hz: 3H); 1.10 (d, J=6.5 Hz: 3H); from 1.75 to 2.05 (mt: 5H); 1.95 (s: 3H); 2.17 (mt: 1H); 2.39 (mt: 1H); 2.76 (mt: 1H); 3.05 (dt, J=17 and 6 Hz: 1H); 3.08 (s: 2H); 3.28 (mt: 1H); 3.50 (mt: 1H); 3.88 (mt: 1H); 3.88 (s: 2H); 4.10 (mt: 1H); 4.52 (mt: 1H); 4.78 (dd, J=10 and 2 Hz: 1H); 4.83 (dd, J=9 and 3.5 Hz: 1H); 5.19 (decoupled doublet, J$_{HF}$=48 Hz: 1H); 5.44 (d, J=9 Hz: 1H); 5.78 (mt: 1H); 5.83 (dd, J=16 and 2 Hz: 1H); 6.00 (mt: 1H); 6.05 (mt: 1H); 6.22 (d, J=16 Hz: 1H); 6.52 (dd, J=16 and 5 Hz: 1H); 7.41 (d, J=8 Hz: 2H); 7.97 (d, J=8 Hz: 2H); 8.16 (s: 1H).

EXAMPLE 20

(16R)-16-Deoxo-16-fluoro-14-O-{4-[(2-diethylamino)ethoxymethyl]benzoyl}-pristinamycin II$_B$ 0.6 g of 4-((2-diethylamino)ethoxymethyl)benzoic acid, 0.05 g of 4-dimethylaminopyridine, 0.43 g of N,N'-dicyclohexylcarbodiimide and 2 g of magnesium sulfate are added, at 20° C., to 1 g of (16R)-16-deoxo-16-fluoropristinamycin II$_{B_3}$ (prepared as described in Example 1) in solution in 15 cm$^3$ of dichloromethane. After stirring for 40 hours at 20° C., 0.24 g of 4-((2-diethylamino)ethoxymethyl)benzoic acid, 0.025 g of 4-dimethylaminopyridine and 0.2 g of N,N'-dicyclohexylcarbodiimide are added. After stirring for an additional 3 hours at 20° C., the reaction mixture is filtered and the insoluble matter is rinsed with 20 cm$^3$ of dichloromethane. The filtrate is washed with 3 times 100 cm$^3$ of water, dried over magnesium sulfate, filtered and then concentrated to dryness under reduced pressure (2.7 kPa) to give 1.5 g of a beige solid which is purified by flash chromatography [eluent: dichloromethane/methanol/acetonitrile gradient (90/5/5 and 84/8/8 by volume)]. After stirring in 20 cm$^3$ of ether, filtration and drying, 0.86 g of a white solid is thus obtained, which solid is dissolved in 20 cm$^3$ of dichloromethane. The solution obtained is washed with twice 50 cm$^3$ of a saturated aqueous sodium bicarbonate solution, dried over magnesium sulfate, filtered and then concentrated under reduced pressure (2.7 kPa) at 20° C., to give 0.67 g of (16R)-16-deoxo-16-fluoro-14-O-{4-[(2-diethylamino) ethoxymethyl]benzoyl }pristinamycin II$_B$, in the form of a white solid melting at around 76° C. (dec.).

$^1$H NMR spectrum (400 MHz, CDCl$_3$, δ in ppm): 0.96 (d, J=6.5 Hz: 3H); 1.01 (d, J=6.5 Hz: 3H); 1.05 (t, J=7 Hz: 6H); 1.10 (d, J=6.5 Hz: 3H); from 1.75 to 2.05 (mt: 5H); 1.95 (s: 3H); 2.16 (mt: 1H); 2.40 (mt: 1H); 2.60 (q, J=7 Hz: 4H); 2.72 (t, J=6.5 Hz: 2H); 2.77 (mt: 1H); 3.04 (dt, J=17.5 and 6 Hz: 1H); 3.29 (mt: 1H); 3.49 (mt: 1H); 3.59 (t, J=6.5 Hz: 2H); 3.89 (mt: 1H); 4.09 (mt: 1H); 4.53 (mt: 1H) 4.59 (s: 2H); 4.79 (dd, J=10 and 2 Hz: 1H); 4.83 (dd, J=9 and 3.5 Hz: 1H); 5.18 (decoupled doublet, J$_{HF}$=48 Hz: 1H); 5.45 (d, J=9 Hz: 1H); 5.78 (mt: 1H); 5.82 (dd, J=17 and 2 Hz: 1H); 5.92 (mt: 1H); 6.05 (mt: 1H); 6.22 (d, J=16 Hz: 1H); 6.51 (dd, J=17 and 5 Hz: 1H); 7.41 (d, J=8 Hz: 2H); 7.99 (d, J=8 Hz: 2H); 8.14 (s: 1H).

4-[(2-Diethylamino)ethoxymethyl]benzoic acid may be prepared in the following manner:

28 cm$^3$ of a 1N aqueous sodium hydroxide solution are added, at 20° C., to 3.67 g of methyl 4-[(2-diethylamino) ethoxymethyl]benzoate in solution in 50 cm$^3$ of methanol. After stirring for 2.5 hours at 20° C., the pH of the reaction mixture is adjusted to 5 by addition of 29 cm$^3$ of a 1 N aqueous hydrochloric acid solution. The reaction mixture is concentrated to dryness under reduced pressure (2.7 kPa) to give a residue which is stirred in 50 cm$^3$ of methanol. After filtration of the insoluble matter, the filtrate is concentrated to dryness under reduced pressure (2.7 kPa) to give a residue which is stirred in 50 cm$^3$ of dichloromethane. After filtration of the insoluble matter, the filtrate is concentrated to dryness under reduced pressure (2.7 kPa), at 20° C., to give 3.5 g of 4-[(2-diethylamino)ethoxymethyl]benzoic acid in the form of a yellow oil.

$^1$H NMR spectrum (300 MHz, (CD$_3$)$_2$SO d6, δ in ppm): 1.07 (t, J=7.5 Hz: 6H); 2.79 (q, J=7.5 Hz: 4H); 2.93 (t, J=6.5 Hz: 2H); 3.66 (t, J=6.5 Hz: 2H); 4.57 (s: 2H); 7.42 (d, J=8 Hz: 2H); 7.92 (d, J=8 Hz: 2H).

Methyl 4-[(2-diethylamino)ethoxymethyl]benzoate may be prepared in the following manner:

2.64 g of sodium hydride (at 60% by weight in liquid paraffin) are added, at 0° C., to 5.8 cm$^3$ of N,N-diethylethanolamine in solution in 15 cm$^3$ of dimethylformamide. After stirring for 1 hour at 0° C., there are added dropwise over 20 minutes 10 g of methyl 4-(bromomethyl)benzoate in solution in 10 cm$^3$ of dimethylformamide, and then 50 cm$^3$ of dimethylformamide. After stirring for 17 hours at 20° C., 100 cm$^3$ of methanol are added and then the reaction mixture is concentrated to dryness under reduced pressure (2.7 kPa) to give a yellow oil which is diluted in 200 cm$^3$ of ethyl acetate. The solution obtained is washed with 300 cm$^3$ of water. The aqueous phase is separated after settling and then extracted with 100 cm$^3$ of ethyl acetate. The organic phases are combined, washed with twice 500 cm$^3$ of water, dried over magnesium sulfate, filtered and concentrated to dryness under reduced pressure (2.7 kPa) to give 10 g of a yellow oil which is purified by flash chromatography [eluent: dichloromethane/methanol gradient ((96/4 and 90/10 by volume)]. 3:67 g of methyl 4-[(2-diethylamino)ethoxymethyl]benzoate are thus obtained in the form of a yellow oil.

$^1$H NMR spectrum (400 MHz, CDCl$_3$, δ in ppm): 1.02 (t, J=7.5 Hz: 6H); 2.58 (q, J=7.5 Hz: 4H); 2.70 (t, J=6 Hz: 2H); 3.57 (t, J=6 Hz: 2H); 3.88 (s: 3H); 4.56 (s: 2H); 7.38(d, J=8Hz :2H);7.99(d, J=8Hz: 2H).

EXAMPLE 21

(16R)-16-Deoxo-16-fluoro-14-O-[3-(morpholin-4-ylmethyl)benzoyl]pristinamycin II$_B$ Carrying out the procedure in a manner similar to that described in Example 9, but starting with 1 g of (16R)-16-deoxo-16-fluoro-14-O[3-(chloromethyl)benzoyl]-pristinamycin II$_B$ in solution in 25 cm$^3$ of tetrahydrofuran, 0.212 g of sodium iodide and 0.253 cm$^3$ of morpholine are added at 20° C. After stirring for 16 hours under reflux and a treatment similar to that in Example 9, 1 g of a yellow solid is obtained which is purified by flash chromatography [eluent: dichloromethane/methanol/acetonitrile gradient (100/ 0/0 and then 98/1/1 by volume)]. 0.8 g of a yellow solid is thus obtained which gives, after stirring in 10 cm$^3$ of ether, filtration and drying (90 Pa) at 20° C., 0.68 g of (16R)-16-deoxo-16-fluoro-14-O-[3-(morpholin4-ylmethyl)benzoyl] pristinamycin II$_B$, in the form of a white solid melting at around 198° C. (dec.).

$^1$H NMR spectrum (400 MHz, CDCl$_3$, δ in ppm): 0.96 (d, J=6.5 Hz: 3H); 1.01 (d, J=6.5 Hz: 3H); 1.10 (d, J=6.5 Hz: 3H); from 1.75 to 2.05 (mt: 5H); 1.96 (s: 3H); 2.17 (mt: 1H); from 2.35 to 2.50 (mt: 1H); 2.46 (mt: 4H); 2.76 (mt: 1H); 3.05 (td, J=17 and 6 Hz: 1H); 3.29 (mt: 1H); from 3.45 to 3.60 (mt: 1H); 3.54 (s: 2H); 3.72 (mt: 4H); 3.88 (mt: 1H); 4.10 (mt: 1H); 4.53 (mt: 1H); 4.79 (dd, J=10 and 1.5 Hz:

1H); 4.83 (dd, J=9 and 3 Hz: 1H); 5.18 (decoupled doublet, $J_{HF}$=48 Hz: 1H); 5.45 (d, J=9 Hz: 1H); 5.79 (mt: 1H); 5.82 (dd, J=17 and 2 Hz: 1H); 5.93 (mt: 1H); 6.06 (mt: 1H); 6.22 (d, J=16 Hz: 1H); 6.52 (dd, J=17 and 5 Hz: 1H); 7.40 (t, J=8 Hz: 1H); 7.56 (broad d, J=8 Hz: 1H); 7.92 (broad d, J=8 Hz: 1H); 7.96 (broad s: 1H); 8.14 (s: 1H).

(16R)-16-Deoxo-16-fluoro-14-O-[3-(chloromethyl)benzoyl]pristinamycin II$_B$ may be prepared in the following manner:

2 cm$^3$ of triethylamine, 2 cm$^3$ of 3-(chloromethyl)benzoyl chloride and 0.23 g of 4-dimethylaminopyridine are added, at 20° C., to 5 g of (16R)-16-deoxo-16-fluoropristinamycin II$_B$ (prepared as described in Example 1) in solution in 250 cm$^3$ of dichloromethane. After stirring for 24 hours at 20° C., the reaction mixture is washed with three times 120 cm$^3$ of water, dried over magnesium sulfate, filtered and then concentrated to dryness under reduced pressure (2.7 kPa) to give a yellow solid which is stirred in 50 cm$^3$ of ether. After filtration, rinsing of the solid with twice 10 cm$^3$ of diethyl ether and drying under reduced pressure (2.7 kPa) at 20° C., 5.56 g of (16R)-16-deoxo-16-fluoro-14-O-[3-(chloromethyl)benzoyl]pristinamycin II$_B$ are obtained in the form of a white solid melting at around 190° C. (dec.).

$^1$H NMR spectrum (400 MHz, CDCl$_3$, δ in ppm): 0.96 (d, J=6.5 Hz: 3H); 1.01 (d, J=6.5 Hz: 3H); 1.10 (d, J=6.5 Hz: 3H); from 1.80 to 2.05 (mt: 5H); 1.96 (s: 3H); 2.17 (mt: 1H); 2.40 (mt: 1H); 2.76 (mt: 1H); 3.05 (dt, J=17 and 6 Hz: 1H); 3.29 (mt: 1H); 3.50 (mt: 1H); 3.88 (mt: 1H); 4.10 (mt: 1H); 4.53 (mt: 1H); 4.63 (s: 2H); 4.79 (dd, J=10 and 2 Hz: 1H); 4.84 (dd, J=9 and 3 Hz: 1H); 5.18 (decoupled doublet, $J_{HF}$=48 Hz: 1H); 5.45 (d, J=9.5 Hz: 1H); from 5.75 to 5.85 (mt: 1H); 5.82 (dd, J=16 and 1.5 Hz: 1H); 5.92 (mt: 1H); 6.07 (dt, J=9.5 and 5 Hz: 1H); 6.23 (d, J=16 Hz: 1H); 6.52 (dd, J=16 and 5 Hz: 1H); 7.46 (t, J=8 Hz: 1H); 7.61 (broad d, J=8 Hz: 1H); 7.99 (broad d, J=8 Hz: 1H); 8.04 (broad s: 1H); 8.14 (s: 1H).

EXAMPLE 22

(16R)-16-Deoxo-16-fluoro-14-O-[3-(imidazol-1-ylmethyl)benzoyl]pristinamycin II$_B$ methanesulfonate 6.28 cm$^3$ of a 0.1 N ethanolic methanesulfonic acid solution are added, at 20° C., to 0.450 g of (16R)-16-deoxo-16-fluoro-14-O-[3-(imidazol-1-ylmethyl)benzoyl]-pristinamycin II$_B$ cm$^3$ of ethanol. After stirring for 10 minutes, the reaction mixture is concentrated to dryness under reduced pressure (2.7 kPa) to give a residue which is stirred in 7 cm$^3$ of ether. After filtration, washing of the solid with twice 2 cm$^3$ of diethyl ether and drying under reduced pressure (2.7 kPa), 0.479 g of (16R)-16-deoxo-16-fluoro-14-O-[3-(imidazol-1-yl methyl)benzoyl]pristinamycin II$_B$ methanesulfonate is obtained in the form of a white solid melting at around 160° C. (dec.).

$^1$H NMR spectrum (400 MHz, CDCl$_3$, δ in ppm): 0.96 (d, J=6.5 Hz: 3H); 1.00 (d, J=6.5 Hz: 3H); 1.11 (d, J=6.5 Hz: 3H); from 1.75 to 2.05 (mt: 5H); 1.96 (s: 3H); 2.17 (mt: 1H); 2.37 (mt: 1H); 2.77 (mt: 1H); 2.86 (s: 3H); 3.05 (mt: 1H); 3.29 (mt: 1H); 3.53 (mt: 1H); 3.85 (mt: 1H); 4.11 (mt: 1H); 4.53 (mt: 1H); 4.80 (broad d, J=10 Hz: 1H); 4.84 (dd, J=9 and 3 Hz: 1H); 5.18 (decoupled doublet, $J_{HF}$=48 Hz: 1H); from 5.35 to 5.50 (mt: 3H); 5.82 (mt: 1H); 5.86 (broad d, J=17 Hz: 1H); 6.07 (mt: 1H); 6.11 (mt: 1H); 6.22 (d, J=16 Hz: 1H); 6.55 (dd, J=17 and 5 Hz: 1H); 7.10 (broad s: 1H); 7.43 (broad s: 1H); 7.54 (mt: 2H); 7,95 (broad s: 1H); 8.09 (mt: 1H); 8.12 (s: 1H); 9.11 (broad s: 1H).

(16R)-16-Deoxo-16-fluoro-14-O-[3-(imidazol -1ylmethyl)benzoyl]pristinamycin II$_B$ may be prepared in the following manner:

Carrying out the procedure in a manner similar to that described in Example 9, but starting with 1.2 g of (16R)-16-deoxo-16-fluoro-14-O-[3-(chloromethyl)benzoyl]-pristinamycin II$_B$ (prepared as described in Example 21) in solution in 30 cm$^3$ of tetrahydrofuran, 0.263 g of sodium iodide and 0.238 g of imidazole are added at 20° C. After stirring for 16 hours under reflux and a treatment similar to that in Example 9, 0.9 g of a yellow solid is obtained, which solid is purified by flash chromatography [eluent: dichloromethane/methanol/acetonitrile gradient (98/1/1 and then 96/2/2 and then 90/5/5 by volume)]. 0.53 g of (16R)-16-deoxo-16-fluoro-14-O-[3-(imidazol-1-ylmethyl)benzoyl] pristinamycin II$_B$ is thus obtained in the form of a yellow solid melting at around 125° C. (dec.).

$^1$H NMR spectrum (400 MHz, CDCl$_3$, δ in ppm): 0.96 (d, J=6.5 Hz: 3H); 1.00 (d, J=6.5 Hz: 3H); 1.10 (d, J=6.5 Hz: 3H); from 1.75 to 2.05 (mt: 5H); 1.95 (s: 3H); 2.16 (mt: 1H); 2.38 (mt: 1H); 2.76 (mt: 1H); 3.04 (dt, J=17 and 6 Hz: 1H); 3.28 (mt: 1H); 3.50 (mt: 1H); 3.86 (mt: 1H); 4.10 (mt: 1H); 4.53 (mt: 1H); 4.79 (dd, J=10 and 2 Hz: 1H); 4.83 (dd, J=9 and 4 Hz: 1H); 5.17 (s: 2H); 5.17 (decoupled doublet, $J_{HF}$=48 Hz: 1H); 5.43 (d, J=9 Hz: 1H); 5.79 (mt: 1H); 5.82 (dd, J=16 and 2 Hz: 1H); 5.97 (mt: 1H); 6.06 (mt: 1H); 6.22 (d, J=16 Hz: 1H); 6.52 (dd, J=16 and 5 Hz: 1H); 6.91 (unresolved complex: 1H); 7.11 (broad s: 1H); 7.32 (broad d, J=8 Hz: 1H); 7.44 (t, J=8 Hz: 1H); 7.57 (broad s: 1H); 7.88 (broad s: 1H); 7.99 (broad d, J=8 Hz: 1H); 8.14 (s: 1H).

EXAMPLE 23

(16R)-16-Deoxo-16-fluoro-14-O-[3-(diethylaminomethyl)benzoyl]pristinamycin II$_B$ Carrying out the procedure in a manner similar to that described in Example 9, but starting with 1 g of (16R)-16-deoxo-16-fluoro-14-O-[3-(chloromethyl)benzoyl]-pristinamycin 18 (prepared as described in Example 21) in solution in 25 cm$^3$ of tetrahydrofuran, 0.217 g of sodium iodide and 0.3 cm$^3$ of diethylamine are added at 20° C. After stirring for 16 hours under reflux and a treatment similar to that in Example 9, 1 g of a yellow solid is obtained, which solid is purified by flash chromatography [eluent: dichloromethane/methanol/acetonitrile gradient (100/0/0 and then 98/1/1 by volume)]. A solid is obtained which is stirred in pentane, filtered and dried (2.7 kPa) at 20° C. to give 0.313 g of (16R)-16-deoxo-16-fluoro-14-O-[3-(diethylaminomethyl)benzoyl]pristinamycin II$_B$, in the form of a yellow solid melting at around 115° C. (dec.).

$^1$H NMR spectrum (400 MHz, CDCl$_3$, δ in ppm): 0.96 (d, J=6.5 Hz: 3H); 1.01 (d, J=6.5 Hz: 3H); from 1.05 to 1.15 (mt: 9H); from 1.75 to 2.05 (mt: 5H); 1.97 (s: 3H); 2.16 (mt: 1H); 2.41 (mt: 1H); 2.56 (mt: 4H); 2.77 (mt: 1H); 3.05 (td, J=17 and 6 Hz: 1H); 3.29 (mt: 1H); 3.49 (mt: 1H); 3.64 (broad s: 2H); 3.89 (mt: 1H); 4.10 (mt: 1H); 4.53 (mt: 1H); 4.79 (dd, J=10 and 1.5 Hz: 1H); 4.83 (dd, J=9 and 3 Hz: 1H); 5.19 (decoupled doublet, $J_{HF}$=48 Hz: 1H); 5.46 (d, J=9.5 Hz: 1H); 5.78 (mt: 1H); 5.82 (dd, J=16 and 2 Hz: 1H); 5.94 (mt: 1H); 6.06 (mt: 1H); 6.23 (d, J=16Hz: 1H); 6.52 (dd, J=16 and 5 Hz: 1H); 7.40 (t, J=8 Hz: 1H); 7.62(mt: 1H); 7.91 (d, J=8 Hz: 1H); 7.97 (broad s: 1H); 8.14 (s: 1H).

EXAMPLE 24

(16R)-16-Deoxo-16-fluoro-14-O-[4-(morpholin4-ylmethyl)phenylacetyl]-pristinamycin $II_B$ 0.25 cm$^3$ of morpholine and a few crystals of sodium iodide are added, at 20° C., to 0.87 g of (16R)-16-deoxo-16-fluoro-14-O-[4-(halomethyl)phenylacetyl]pristinamycin $II_B$ (mixture of the chlorinated and brominated derivatives) in solution in 5 cm$^3$ of dimethylformamide. After stirring for 15 minutes at 85° C., the reaction mixture is poured over 90 cm$^3$ of water. The aqueous phase is separated after settling and then extracted with twice 50 cm$^3$ of ethyl acetate. The organic phases are combined, washed successively with 30 cm$^3$ of water and 30 cm$^3$ of a saturated aqueous sodium chloride solution, and then dried over magnesium sulfate, filtered and concentrated to dryness under reduced pressure (2.7 kPa). 0.91 g of an orange-brown solid is thus obtained, which solid is purified by flash chromatography [eluent: dichloromethane/methanol/acetonitrile (92/4/4 by volume)) to give 0.46 g of a yellow solid which is taken up in 5 cm$^3$ of dichloromethane. After filtration on Celite®, the Celite® is rinsed with dichloromethane. The filtrate is concentrated to dryness under reduced pressure (2.7 kPa) to give 0.42 g of a yellow solid which is stirred for 15 minutes in 5 cm$^3$ of water. After filtration and drying under reduced pressure (2.7 kPa) at 20° C., 0,38 g of (16R)-16-deoxo-16-fluoro-14-O-14-(morpholin-4-ylmethyl)phenylacetyl]-pristinamycin $II_B$ is obtained in the form of a yellow solid melting at around 100° C. (dec.).

$^1$H NMR spectrum (400 MHz, CDCl$_3$, δ in ppm): 0.96 (d, J=6.5 Hz: 3H); 1.01 (d, J=6.5 Hz: 3H); 1.09 (d, J=6.5 Hz: 3H); from 1.60 to 2.05 (mt: 5H); 1.85 (s: 3H); from 2.10 to 2.30 (mt: 2H); 2.44 (mt: 4H); 2.76 (mt: 1H); 2.97 (dt, J=17 and 6 Hz: 1H); 3.22 (mt: 1H); from 3.40 to 3.55 (mt: 1H); 3.48 (s: 2H); 3.59 (s: 2H); 3.71 (mt: 4H); 3.85 (mt: 1H); 4.04 (mt: 1H); 4.52 (mt: 1H); 4.78 (broad d, J=10 Hz: 1H); 4.82 (dd, J=9 and 3 Hz: 1H); 5.06 (decoupled doublet, $J_{HF}$=48 Hz: 1H); 5.31 (d, J=9 Hz: 1H); from 5.75 to 5.85 (mt: 1H); 5.75 (mt: 1H); 5.81 (broad d, J=17 Hz: 1H); 5.93 (mt: 1H); 6.18 (d, J=16 Hz: 1H); 6.51 (dd, J=17 and 4 Hz: 1H); 7.22 (d, J=8Hz: 2H); 7.29 (d, J=8 Hz: 2H); 8.12 (s: 1H).

(16R)-16-Deoxo-16-fluoro-14-O-[4-(halomethyl)phenylacetyl]pristinamycin $II_B$ (mixture of the chlorinated and brominated derivatives) may be prepared in the following manner:

1.3 cm$^3$ of diisopropylethylamine and 1.75 g of 4-(bromomethyl)phenylacetyl chloride are added over 5 minutes, at 20° C., under an argon atmosphere, to 2 g of (16R)-16-deoxo-16-fluoropristinamycin $II_B$ (prepared as described in Example 1) in solution in 60 cm$^3$ of dichloromethane. After stirring for 16 hours at 20° C., the reaction mixture is successively washed with twice 25 cm$^3$ of water and 25 cm$^3$ of a saturated aqueous sodium chloride solution, and then dried over magnesium sulfate, filtered and concentrated to dryness under reduced pressure (2.7 kPa). 2.79 g of an orange-colored solid are thus obtained, which solid is purified by flash chromatography [eluent: dichloromethane/methanol (97/3 by volume)] to give 1.3 g of a yellow solid which is taken up in 50 cm$^3$ of ethyl acetate. The solution obtained is washed with twice 25 cm$^3$ of a saturated aqueous sodium bicarbonate solution and then dried over magnesium sulfate, filtered and concentrated to dryness under reduced pressure (2.7 kPa) at 20° C. to give 1.04 g of (16R)-16-deoxo-16-fluoro-14-O-[4-(halomethyl)-phenylacetyl]pristinamycin $II_B$ (mixture of the chlorinated and brominated derivatives) in the form of a yellow solid.

4-(Bromomethyl)phenylacetyl chloride may be prepared according to Patent Application EP 274 999.

EXAMPLE 25

(16R)-16-Deoxo-16-fluoro-14-O-[(2-imidazol-1-ylethoxy)acetyl]pristinamycin $II_B$ methanesulfonate 0.26 cm$^3$ of a 1.09 N ethanolic methanesulfonic acid solution is added, at 20° C., to 0.19 g of (16R)-16-deoxo-16-fluoro-14-O-[(2-imidazol-1-ylethoxy)acetyl]-pristinamycin $II_B$ in solution in 8 cm$^3$ of ethanol. After stirring for 10 minutes, the reaction mixture is concentrated to dryness under reduced pressure (2.7 kPa) to give an oily residue which is stirred in 5 cm$^3$ of diethyl ether. The solvent is then removed under reduced pressure (2.7 kPa). The solid thus obtained is stirred in 5 cm$^3$ of diethyl ether and then filtered, rinsed with diethyl ether and dried under reduced pressure (2.7 kPa) to give 0.189 g of (16R)-16-deoxo-16-fluoro-14-O-[(2-imidazol-1-ylethoxy)acetyl]pristinamycin $II_B$ methanesulfonate in the form of a melting at around 115° C. (dec.).

$^1$H NMR spectrum (400 MHz, CDCl$_3$, δ in ppm): 0.95 (mt: 6H); 1.12 (d, J=6.5 Hz: 3H); from 1.50 to 2.25 (mt: 7H); 1.86 (s: 3H); 2.79 (mt: 1H); 2.83 (s: 3H); 3.02 (mt: 1H); 3.26 (mt: 1H); 3.58 (mt: 1H); 3.72 (mt: 1H); from 3.80 to 3.90 (mt: 2H); from 4.00 to 4.15 (mt: 3H); 4.34 (mt: 1H); from 4.50 to 4.60 (mt: 2H); from 4.80 to 4.90 (mt: 2H); from 4.90 to 5.00 (mt: 1H); 4.94 (broad d, J=10 Hz: 1H); from 5.75 to 5.95 (mt: 2H); 6.06 (broad d, J=16 Hz: 1H); 6.12 (d, J=16 Hz: 1H); 6.65 (dd, J=16 and 5 Hz: 1H); 6.95 (mt: 1H); 7.30 (broad s: 1H); 7.36 (broad s: 1H); 8.12 (s: 1H); 9.18 (broad s: 1H); 14.73 (broad unresolved complex: 1H).

(16R)-16-Deoxo-16-fluoro-14-O-[(2-imidazol-1-ylethoxy)acetyl]pristinamycin $II_B$ may be prepared in the following manner:

0.41 g of imidazole and a few crystals of sodium iodide are added, at 20° C., to 1.3 g of (16R)-16-deoxo-16-fluoro-14-O-[2-chloroethoxyacetyl]pristinamycin $II_B$ in solution in 6.5 cm$^3$ of dimethyl sulfoxide. After stirring for 4 hours at 60° C., 0.3 g of sodium iodide is added. After stirring for another 4 hours at 60° C., for 72 hours at 85° C. and then for 60 hours at 20° C., the reaction mixture is poured over a mixture of 35 cm$^3$ of water and ice and then supplemented with 0.17 g of sodium bicarbonate. After filtration, washing of the solid with water and then air-drying, an oily residue is obtained which is diluted in 30 cm$^3$ of dichloromethane. After concentrating under reduced pressure (2.7 kPa), 1.23 g of a yellow solid is obtained, which solid is purified by flash chromatography on 20–40 Å Amicon_____® silica [eluent: dichloromethane/methanol/acetonitrile (88/6/6 by volume)]. 0.64 g of (16R)-16-deoxo-16-fluoro-14-O-[(2-imidazol-1-ylethoxy)acetyl]pristinamycin $II_B$ is thus obtained in the form of a pale yellow solid.

$^1$H NMR spectrum (400 MHz, CDCl$_3$, δ in ppm): 0.96 (d, J=6.5 Hz: 3H); 1.00 (d, J=6.5 Hz: 3H); 1.10 (d, J=6.5 Hz: 3H); from 1.65 to 2.05 (mt: 5H); 1.89 (s: 3H); from 2.10 to 2.30 (mt: 2H); 2.76 (mt: 1H); 2.99 (dt, J=17 and 6.5 Hz: 1H); 3.24 (mt: 1H); 3.51 (mt: 1H); from 3.75 to 3.90 (mt: 3H); 4.03 (limiting AB: 2H); 4.07 (mt: 1H); 4.17 (t, J=5 Hz: 2H); 4.55 (mt: 1H); from 4.75 to 4.85 (mt: 2H); 5.10 (decoupled doublet, $J_{HF}$=48 Hz: 1H); 5.24 (d, J=9 Hz: 1H); 5.78 (mt: 1H); from 5.80to5.95 (mt: 1H); 5.87 (dd, J=16 and 2 Hz: 1H); 6.18 (d, J=16 Hz: 1H); 6.31 (mt: 1H); 6.56 (dd, J=16 and 5Hz: 1H); 7.01 (s: 1H); 7.08 (s: 1H); 7.59 (s: 1H); 8.12 (s: 1H).

(16R)-16-Deoxo-16-fluoro-14-O-[2-chloroethoxyacetyl] pristinamycin II$_B$ may be prepared in the following manner:

3.1 g of N,N∝O-dicyclohexylcarbodiimide, 0.61 g of 4-dimethylaminopyridine and 2.08 g of 2-chloroethoxyacetic acid in solution in 20 cm$^3$ of dichloromethane are added, at 20° C., to 5,32 g of (16R)-16-deoxo-16-fluoropristinamycin II$_B$ (prepared as described in Example 1) in solution in 130 cm$^3$ of dichloromethane. After stirring for 1 hour at 20° C., the reaction mixture is filtered and the residue is rinsed with dichloromethane. The filtrate is concentrated to dryness under reduced pressure (2.7 kPa) to give 7.68 g of an orange-colored solid which is purified by flash chromatography on 20–40 Å Amicon® _____ silica [eluent: dichloromethane/ethyl acetate (50/50 by volume)]. 4.68 g of (16R)-16-deoxo-16-fluoro-14-O-t2-chloroethoxyacetyl) pristinamycin II$_B$ are thus obtained in the form of a white powder.

$^1$H NMR spectrum (400 MHz, CDCl$_3$, δ in ppm): 0.96 (d, J=6.5 Hz: 3H); 1.00 (d, J=6.5 Hz: 3H); 1.09 (d, J=6.5 Hz: 3H); from 1.70 to 2.05 (mt: 5H); 1.90 (s: 3H); 2.15 (mt: 1H); 2.26 (mt: 1H); 2.76 (mt: 1H); 2.99 (dt, J=17 and 6 Hz: 1H); 3.24 (mt: 1H); 3.50 (mt: 1H); 3.67 (t, J=6 Hz: 2H); from 3.80 to 3.90 (mt: 1H); 3.83 (t, J=6 Hz: 2H); 4.05 (mt: 1H); 4.14 (limiting AB, J=13 Hz: 2H); 4.52 (mt: 1H); 4.78 (dd, J=10 and 1.5 Hz: 1H); 4.82 (dd, J=9 and 3 Hz: 1H); 5.12 (decoupled doublet, J$_{HF}$=48Hz: 1H); 5.31 (broad d, J=9Hz: 1H); 5.78 (mt: 1H); 5.82(dd, J=16 and 2 Hz: 1H); from 5.85 to 5.95 (mt: 2H); 6.19(d, J=16 Hz: 1H); 6.52(dd, J=16 and 5 Hz: 1H); 8.12 (s: 1H).

2-Chloroethoxyacetic acid may be prepared according to E. J. Corey and Christopher J. Helal, Tetrahedron Letters, Vol. 37, No. 28, pp. 4837–4840, 1996.

EXAMPLE 26

(16R)-14-O-{3,3-Dimethyl-3-[4,6-dimethyl-2-(4-morpholin4-ylbutyryloxy)phenyl]-propionyl}-16-deoxo-6-fluoropristinamycin II$_B$ 0.48 cm$^3$ of morpholine is added, at 20° C. and under an argon atmosphere, to 1.6 g of (16R)-14-O-{3-[2-(4-bromobutyryloxy)-4,6-dimethylphenyl]-3,3-dimethylpropionyl}-16-deoxo-16-fluoropristinamycin II$_B$ in solution in 8 cm$^3$ of dimethyl sulfoxide. After stirring for 30 minutes at 60° C., the reaction mixture is poured over 300 cm$^3$ of a water-ice mixture. The precipitate is isolated by filtration, rinsed with twice 20 cm$^3$ of distilled water and then dissolved in 150 cm$^3$ of dichloromethane. The solution obtained is washed with three times 20 cm$^3$ of distilled water, dried over magnesium sulfate, filtered and then concentrated to dryness under reduced pressure (2.7 kPa) to give 1.7 g of a residue which is purified by flash chromatography [eluent: dichloromethane/methanol (94/6 by volume)]. A solid is obtained which, after stirring in diisopropyl ether, filtration and drying (2.7 kPa) at 20° C., gives 0.52 g of (16R)-14-O-{3,3 -dimethyl-3-[4,6-dimethyl-2-(4-morpholin34-ylbutyryloxy)phenyl]propionyl}-16-deoxo-16-fluoropristinamycin II$_B$, in the form of a white solid melting at around 88° C. (dec.).

$^1$H NMR spectrum (400 MHz, CDCl$_3$, δ in ppm): 0.96 (d, J=6.5 Hz: 3H); 1.01 (d, J=6.5 Hz: 3H); 1.09 (d, J=6.5 Hz: 3H); from 1.40 to 1.60 (mt: 1H); 1.56 (s: 3H); 1.58 (s: 3H); from 1.75 to 2.05 (mt: 7H); 1.80 (s: 3H); 2.14 (mt: 1H); 2.25 (s: 3H); from 2.40 to 2.50 (mt: 6H); 2.54 (s: 3H); 2.63 (t, J=7.5 Hz: 2H); from 2.70 to 2.80 (mt: 1H); 2.75 (d, J=15 Hz: 1H); 2.85 (d, J=15 Hz: 1H); 2.91 (mt: 1H); 3.15 (mt: 1H); 3.45 (mt: 1H); 3.73 (t, J=5 Hz: 4H); 3.86 (mt: 1H); 4.01 (mt: 1H); 4.53 (mt: 1H); from 4.70 to 4.95 (mt: 1H); 4.77 (dd, J=10 and 1.5 Hz: 1H); 4.80 (dd, J=9 and 3 Hz: 1H); 5.11 (d, J=9 Hz: 1H); 5.66 (mt: 1H); 5.71 (mt: 1H); 5.81 (dd, J=17 and 2 Hz: 1H); 5.93 (mt: 1H); 6.12 (d, J=16 Hz: 1H); 6.50 (dd, J=17 and 5 Hz: 1H); 6.61 (d, J=1.5 Hz: 1H); 6.81 (broad s: 1H); 8.12 (s: 1H).

(16R)-14-O-{3-[2-(4-Bromobutyryloxy)4,6-dimethylphenyl]-3,3-dimethyl-propionyl}-16-deoxo-16-fluoro-pristinamycin II$_B$ may be prepared in the following manner:

1.2 g of N,N'-dicyclohexylcarbodiimide, 2.06 g of (16R)-16-deoxo-16-fluoropristinamycin II$_B$ (prepared as described in Example 1) and 0.07 g of 4-dimethylaminopyridine are added, at 20° C., under an argon atmosphere, to 2.7 g of 3-[2-(4-bromobutyryloxy4,6-dimethylphenyl]-3,3-dimethylpropionic acid in solution in 150 cm$^3$ of dichloromethane. After stirring for 18 hours, the reaction mixture is filtered to remove the insoluble matter. The filtrate is washed with four times 25 cm$^3$ of distilled water, dried over magnesium sulfate, filtered and then concentrated to dryness under reduced pressure (2, 7 kPa) to give 4.6 g of a residue which is purified by two successive flash chromatographies (eluent: dichloromethane/methanol, 96/4 and then 97/3 by volume). 1.6 g of (16R)-14-O-13-[2-(4-bromobutyryloxy)-4,6-dimethylphenyl]-3,3-dimethylpropionyl}-16-deoxo-16-fluoro-pristinamycin II$_B$ are obtained in the form of a cream-colored solid.

$^1$H NMR spectrum (400 MHz, CDCl$_3$, δ in ppm): 0.96 (d, J=6.5 Hz: 3H); 1.00 (d, J=6.5 Hz: 3H); 1.09 (d, J=6.5 Hz: 3H); from 1.45 to 2.05 (mt: 12H); 1.79 (s: 3H); 2.13 (mt: 1H); 2.24 (s: 3H); 2.29 (mt: 2H); 2.54 (s: 3H); from 2.70 to 2.90 (mt: 5H); 2.91 (mt: 1H); 3.15 (mt: 1H); 3.45 (mt: 1H); 3.56 (t, J=6.5 Hz: 2H); 3.86 (mt: 1H); 4.01 (mt: 1H); 4.53 (mt: 1H); from 4.75 to 4.95 (mt: 1H); 4.77 (dd, J=10 and 2 Hz: 1H); 4.80 (dd, J=9 and 3 Hz: 1H); 5.12 (d, J=9 Hz: 1H); from 5.60 to 5.75 (mt: 2H); 5.81 (dd, J=16 and 2 Hz: 1H); 5.92 (mt: 1H); 6.13 (d, J=16 Hz: 1H); 6.50 (dd, J=16 and 5 Hz: 1H); 6.59 (d, J=1.5 Hz: 1H); 6.82 (d, J=1.5 Hz: 1H); 8.12 (s: 1H).

3-[2-(4-Bromobutyryloxy)4,6-dimethylphenyl]-3,3-dimethylpropionic acid may be prepared in the following manner:

A solution of 1 g of potassium permanganate in a mixture of 46 cm$^3$ of distilled water and 30 cm$^3$ of acetone is added dropwise, at 20° C., to 2.3 g of 3-[2-(4-bromobutyryloxy) 4,6-dimethylphenyl]-3,3-dimethylpropanal in solution in 200 cm$^3$ of acetone. After stirring for 24 hours, the reaction mixture is supplemented with 100 cm$^3$ of distilled water, acidified to pH 1–2 by addition of a 1 N aqeuous hydrochloric acid solution, and then extracted with five times 100 cm$^3$ of dichloromethane. The organic phases are combined, dried over magnesium sulfate, filtered and then concentrated to dryness under reduced pressure (2.7 kPa). 2.7 g of 3-[2-(4-bromobutyryloxy)4,6-dimethylphenyl]-3,3-dimethylpropionic acid are obtained in the form of a colorless oil.

$^1$H NMR spectrum (400 MHz, CDCl$_3$, δ in ppm); (2 conformers in the proportions 80–20): 1.58 and 1.59 (2 s: 6H in total); 2.23 and 2.24 (2 s: 3H in total); 2.29 (mt: 2H); 2.54 and 2.55 (2 s: 3H in total); 2.78 (t, J=7 Hz: 2H); 2.84 and 2.87 (2 s: 2H in total); 3.55 (t, J=6.5 Hz: 2H); 6.57 and 6.59 (2 broad s: 1H in total); 6.81 and 6.83 (2 broad s: 1H in total).

3-[2-(4-Bromobutyryloxy)-4,6-dimethylphenyl]-3,3-dimethylpropanal may be prepared in the following manner:

2.5 g of 3-[2-(4-bromobutyryloxy)-4,6-dimethylphenyl)-3,3-dimethylpropan-1-ol in solution in 160 cm$^3$ of dichloromethane are added dropwise, at 24° C., to 3.1 g of pyridinium chlorochromate in suspension in 900 cm$^3$ of dichloromethane. After stirring for 2 hours at 24° C., the reaction mixture is filtered on 630 g of silica (particle size 0.063–0.2 mm), eluting successively with pure dichloromethane, and then a mixture of dichloromethane and ethyl acetate (80/20 by volume). 2.4 g of 3-[2-(4-bromobutyryloxy)4,6-dimethylphenyl]-3,3-dimethylpropanal are thus obtained in the form of a colorless viscous oil.

$^1$H NMR spectrum (400 MHz, CDCl$_3$, δ in ppm); (2 conformers in the proportions 80–20): 1.57 (s: 6H); 2.25 (s: 3H); 2.29 (mt: 2H); 2:55 (s: 3H); 2.78 (t, J=7 Hz: 2H); from 2.80 to 2.90 (mt: 2H); 3.56 (t, J=6 Hz: 2H); 6.59 and 6.61 (2 broad s: 1H in total); 6.85 and 6.87 (2 broad s: 1H in total); 9,55 (broad s: 1H).

3-[2-(4-Bromobutyryloxy)4,6-dimethylphenyl]-3,3-dimethylpropan-1-ol may be prepared in the following manner:

2.24 cm$^3$ of triethylamine trihydrofluoride are added dropwise, at 0° C., under an argon atmosphere, to 5.4 g of 2-{3-(tert-butyldimethylsilyloxy])-1,1-dimethylpropyl}-3, 5-dimethylphenol 4-bromobutyrate in solution in 60 cm$^3$ of dichloromethane. After stirring for 42 hours at 20° C., the reaction mixture is filtered on 750 g of silica (particle size 0.063–0.2 mm), eluting successively with dichloromethane and then with a dichloromethane/ethyl acetate mixture (90/10 by volume). 2.6 g of 3-[2-(4-bromobutyryloxy)-4,6-dimethylphenyl]-3,3-dimethylpropan-1-ol are thus obtained in the form of a colorless viscous oil.

$^1$H NMR spectrum (400 MHz, CDCl$_3$, δ in ppm); (2 conformers in the proportions 80–20): 1.50 and 1.52 (2 s: 6H in total); from 2.00 to 2.10 (mt: 2H); 2.23 and 2.24 (2 s: 3H in total); 2.30 (mt: 2H); 2.54 (s: 3H); 2.78 (t, J=7 Hz: 2H); from 3.50 to 3.60 (mt: 4H); 6.55 and 6.56 (2 broad s: 1H in total); 6.82 and 6.84 (2 broad s: 1H in total).

2-{3-(tert-Butyldimethylsilyloxy)-1,1 -dimethylpropyl}-3,5-dimethylphenol 4-bromo-butyrate may be prepared in the following manner:

To 3.22 g of 2-{3-(tert-butyldimethylsilyloxy)-1,1-dimethylpropyl}-3,5-dimethyl-phenol in solution in 60 cm$^3$ of tetrahydrofuran, there are added, at 20° C. under an argon atmosphere and in small portions, 0.32 g of sodium hydride (at 75% in mineral oil), and then 15 minutes later 1.16 cm$^3$ of 4-bromobutyryl chloride. After stirring for 40 minutes, 100 cm$^3$ of ether, 10 cm$^3$ of distilled water and 10 cm$^3$ of a saturated aqueous sodium chloride solution are added. After stirring, the organic phase is decanted off, dried over magnesium sulfate, filtered and then concentrated to dryness under reduced pressure (2.7 kPa) to give a residue which is filtered on 75 g of silica (particle size 0.063–0.2 mm), eluting successively with cyclohexane and then with a cyclohexane/ethyl acetate mixture (90/10 by volume). 2 g of 2-{3-(tert-butyldimethyl-silyloxy)-1,1-dimethylpropyl}-3, 5-dimethylphenol 4-bromobutyrate are thus obtained in the form of a colorless oil.

$^1$H NMR spectrum (300 MHz, CDCl$_3$, δ in ppm); (2 conformers in the proportions)80–20): 0.00 and 0.03 (2 s: 6H in total); 0.87 and 0.89 (2 s: 9H in total); from 1.45 to 1.55 (mt: 6H); 2.05 (t, J=7.5 Hz: 2H); 2.24 and 2.25 (2 s: 3H in total); 2.31 (mt: 2.54 (s: 3H); 2.77 (t, J=7.5 Hz: 2H); from 3.40 to 3.65 (mt: 4H); 6.56 and 6.58 (2 broad s: 1H in total); 6,81 and 6.83 (2 broad s: 1H in total).

2-{3-(tert-Butyldimethylsilyloxy)-1,1 -dimethylpropyl}-3,5-dimethylphenol may be prepared according to Amsberry K. L., Gerstenberger A. E., Borchardt R. T., Pharm. Res. 1991,8(4), 455–61.

EXAMPLE 27

(16R)-16-Deoxo-16-fluoro-14-O-[4-(morpholin-4-yl)butyryl]pristinamycin II$_B$ methanesulfonate 6.58 cm$^3$ of a 0.1 N ethanolic methanesulfonic acid solution are added, at 20° C., to 0.453 g of (16R)-16-deoxo-16-fluoro-14-O-[4-(morpholin4-yl)butyryl]pristinamycin II$_B$ in solution in 10 cm$^3$ of ethanol. After stirring for 10 minutes, the reaction mixture is concentrated to dryness under reduced pressure (2.7 kPa) to give a residue which is stirred in 10 cm$^3$ of ethyl ether. After filtration, rinsing of the solid with 4 cm$^3$ of diethyl ether and drying under reduced pressure (2.7 kPa) at 20° C., 0.506 g of (16R)-16-deoxo-16-fluoro-14-O-[4-(morpholin-4-yl)butyryl]pristinamycin II$_B$ methane-sulfonate is obtained in the form of a white solid melting at around 122° C. (dec.).

$^1$H NMR spectrum (400 MHz, CDCl$_3$, δ in ppm): 0.96 (d, J=6.5 Hz: 3H); 0.99 (d, J=6.5 Hz: 3H); 1.10 (d, J=6.5 Hz: 3H); from 1.60 to 2.00 (mt: 5H); 1.89 (s: 3H); from 2.10 to 2.30 (mt: 4H); 2.48 (t, J=7 Hz: 2H); 2.77 (mt: 1H); 2.82 (s: 3H); 2.88 (mt: 2H); 2.99 (dt, J=17 and 6 Hz: 1H); 3.13 (mt: 2H); 3.23 (dt, J=17 and 6 Hz: 1H); from 3.45 to 3.60 (mt: 3H); 3.82 (mt: 1H); from 3.95 to 4.20 (mt: 5H); 4.53 (mt: 1H); 4.79 (dd, J=10 and 2 Hz: 1H); 4.83 (dd, J=9 and 3.5 Hz: 1H); 5.11 (decoupled doublet, J$_{HF}$=48 Hz: 1H); 5.28 (d, J=10 Hz: 1H); from 5.75 to 5.85 (mt: 2H); 5.84 (dd, J=17 and 2 Hz: 1H); 6.09 (mt: 1H); 6.19 (d, J=16 Hz: 1H); 6.53(dd, J=17and5Hz: 1H);8.11 (s: 1H).

(16R)-16-Deoxo-16-fluoro-14-O-[4-(morpholin4-yl)butyryl]pristinamycin II$_B$ may be prepared in the following manner:

0.512 g of 4-(morpholin4-yl)butyric acid hydrochloride and 0.343 cm$^3$ of triethylamine in solution in 35 cm$^3$ of dichloromethane, 0.503 g of N,N'-dicyclohexylcarbodiimide and 0.03 g of 4-dimethylaminopyridine are added, at 20° C., to 1.3 g of (16R)-16-deoxo-16-fluoropristinamycin II$_B$ (prepared as described in Example 1) in solution in 35 cm$^3$ of dichloromethane. After stirring for 16 hours at 20° C., the reaction mixture is concentrated to dryness under reduced pressure (2.7 kPa). The residue is taken up in 10 cm$^3$ of dichloromethane and then filtered. The filtrate is diluted with 40 cm$^3$ of dichloromethane, washed with 50 cm$^3$ of water and then dried over magnesium sulfate, filtered and concentrated to dryness under reduced pressure (2.7 kPa) to give 1 g of a yellow solid which is purified by flash chromatography [eluent: dichloromethane/methanol/acetonitrile gradient (98/1/1 and then 96/2/2 and then 94/3/3 by volume)]. 0.584 g of a white solid is thus obtained, which solid is taken up in 20 cm$^3$ of dichloromethane. Tie solution obtained is washed with 20 cm$^3$ of water, dried over magensium sulfate, filtered and then concentrated to dryness under reduced pressure (2.7 kPa) to give, after stirring in pentane, filtration and drying (2.7 kPa) at 20° C., 0.524 g of (16R)-16-deoxo-16-fluoro-14-O-[4-(morpholin-4-yl)butyryl]pristinamycin II$_B$, in the form of a white solid melting at around 100° C. (dec.).

$^1$H NMR spectrum (400 MHzr, CDCl$_3$, δ in ppm): 0.96 (d, J=6.5 Hz: 3H); 1.00 (d, J=6.5 Hz: 3H); 1.10 (d, J=6.5 Hz: 3H); from 1.60 to 2.05 (mt: 7H); 1.89 (s: 3H); 2.16 (mt: 1H); 2.23 (mt: 1H); 2.35 (mt: 4H); 2.43 (mt: 4H); 2.76 (mt: 1H); 2.99 (dt, J=17 and 6 Hz: 1H); 3.24 (mt: 1H); 3.49 (mt: 1H); 3.71 (mt: 4H); 3.85 (mt: 1H); 4.07 (mt: 1H); 4.54 (mt: 1H); 4.78 (dd, J=10 and 1.5 Hz: 1H); 4.82 (dd, J=9 and 3 Hz: 1H); 5.11 (decoupled doublet, J$_{HF}$=48 Hz: 1H); 5.30 (d, J=9 Hz: 1H); from 5.75 to 5.85 (mt: 1H); 5.76 (mt: 1H); 5.81 (dd, J=17 and 1.5 Hz: 1H); 5.95 (mt: 1H); 6.19 (d, J=16 Hz: 1H); 6.51 (dd, J=17 and 5 Hz: 1H); 8.12(s: 1H).

4-(Morpholin-4-yl)butyric acid hydrochloride may be prepared according to Raj K. Razdan, Barbara Zitko Terris, Harry G. Pars, J. Med. Chem. 1976, 19 (4), 454–461.

EXAMPLE 28

(16R)-16-Deoxo-16-fluoro-14-O (4-imidazol-1-yl-butyryl)pristinamycin II$_B$ 150 mg of imidazole are added to 600 mg of (16R)-14-O-(4-bromobutyryl)-16-deoxo-16-fluoropristinamycin II$_B$ in solution in 2.5 cm$^3$ of dimethylformamide. After stirring for 4 hours at 60° C., an additional 0.5 g of imidazole is added and the stirring is continued for 2 hours at 65° C. The mixture is concentrated under reduced pressure (2.7 kPa) to give a residue which is taken up in 20 cm$^3$ of distilled water and 25 cm$^3$ of dichloromethane. The organic phase is decanted off and then washed with twice 20 cm$^3$ of distilled water. The organic phase is dried over magnesium sulfate, filtered and then concentrated to dryness under reduced pressure (2.7 kPa) to give 1.13 g of a solid which is purified by flash chromatography [eluent: dichloromethane-methanol (98-2 by volume and then 95-5 by volume)]. 325 mg of a product are thus obtained, which product is stirred in diethyl ether, filtered and then dried at 20° C. (90 Pa) to give 248 mg of (16R)-16-deoxo-16-fluoro-14-O-(4-imidazol-1-ylbutyryl)pristinamycin II$_B$, in the form of a beige solid melting at 125° C.

$^1$H NMR spectrum (400 MHz, CDCl$_3$, δ in ppm): 0.96 (d, J=6.5 Hz: 3H); 1.00 (d, J=6.5 Hz: 3H); 1.10 (d, J=6.5 Hz: 3H); from 1.60 to 2.05 (mt: 5H); 1.90 (s: 3H); from 2.00 to 2.35 (mt: 2H); 2.08 (mt: 2H); 2.26 (mt: 2H); 2.76 (mt: 1H); 2.99 (dt, J=17 and 6.5 Hz: 1H); 3.24 (mt: 1H); 3.50 (mt: 1H); 3.94 (mt: 1H); 4.01 (t, J=7 Hz: 2H); 4.06 (mt: 1H); 4.54 (mt: 1H); 4.79 (dd, J=10 and 2 Hz: 1H); 4.82 (dd, J=9 and 3 Hz: 1H); 5.11 (decoupled doublet, J$_{HF}$=48 Hz: 1H); 5.28 (d, J=9 Hz: 1H) from 5.75 to 5.90 (mt: 1H); 5.78 (mt: 1H); 5.84 (dd, J=16 and 1.5 Hz: 1H); 6.09 (mt: 1H); 6.20 (d, J=16 Hz: 1H); 6.53 (dd, J=16 and 5 Hz: 1H); 6.91 (s: 1H); 7.07 (s: 1H); 7.44 (s: 1H); 8.12 (s: 1H).

(16R)-14-O-(4-Bromobutyryl)-16-deoxo-16-fluoropristinamycin II$_B$ may be prepared in the following manner:

2.64 cm$^3$ of triethylamine and then 2.3 cm$^3$ of 4-bromobutyric acid chloride are added to 5 g of (16R)-16-deoxo-16-fluoropristinamycin II$_B$ (prepared as described in Example 1) in solution in 150 cm$^3$ of dichloromethane. After stirring for 18 hours at 25° C., an additional 1.32 cm$^3$ of ethylamine and 1.15 cm$^3$ of 4-bromobutyric acid chloride are added. The reaction mixture is stirred for 2 hours at 25° C. and then washed with twice 100 cm$^3$ of distilled water. The organic phase is dried over magnesium sulfate, filtered and then concentrated to dryness under reduced pressure (2.7 kPa) to give 8.19 g of a brown oil which is purified by flash chromatography [eluent: dichloromethane-methanol (97-3 by volume)]. 3.4 g of a product are obtained, which product is stirred in diisopropyl ether, filtered, dried and then repurified by flash chromatography [eluent: dichloromethane-methanol (98-2 by volume)]. After stirring in diisopropyl ether, filtration and drying after 20° C. (90 Pa), 1.32 g of (16R)-14-O-(4-bromobutyryl)-16-deoxo-16-fluoropristinamycin II$_B$ are thus obtained in the form of an off-white solid which is used as it is.

$^1$H NMR spectrum (400 MHz, CDCl$_3$, δ in ppm): 0.96 (d, J=6.5 Hz: 3H); 1.00 (d, J=6.5 Hz: 3H); 1.10 (d, J=6.5 Hz: 3H); from 1.65 to 2.05 (mt: 5H); 1.89 (s: 3H); from 2.10 to 2.35 (mt: 2H); 2.17 (mt: 2H); 2.49 (mt: 2H); 2.77 (mt: 1H); 2.99 (mt: 1H); 3.24 (mt: 1H); from 3.45 to 3.55 (mt: 1H); 3.47 (t, J=6.5 Hz: 2H); 3.86 (mt: 1H); 4.06 (mt: 1H); 4.54 (mt: 1H); 4.78 (dd, J=10 and 1.5 Hz: 1H); 4.82 (dd, J=9 and 3 Hz: 1H); 5.13 (decoupled doublet, J$_{HF}$=48 Hz: 1H); 5.31 (d, J=9 Hz: 1H); from 5.75 to 5.90 (mt: 1H); 5.77 (mt: 1H); 5.82 (dd, J=16 and 2 Hz: 1H); 5.93 (mt: 1H); 6.20 (d, J=15 Hz: 1H); 6.52 (dd, J=16 and 5 Hz: 1H); 8.12 (s: 1H).

EXAMPLE 29

(16R)-16-Deoxo-16-fluoro-14-O-{4-[4-(pyrrolidin-1-ylcarbonylmethyl)piperazin-1-yl]butyryl}pristinamycin II$_B$ 590 mg of 1-(pyrrolidinocarbonylmethyl)piperazine are added to 680 mg of (16R)-14-O-(4-bromobutyryl)-16-deoxo-16-fluoropristinamycin II$_B$ (prepared as described in Example 28) in solution in 3 cm$^3$ of dimethylformamide. After stirring for 4 hours at 60° C., the mixture is concentrated under reduced pressure (2.7 kPa) to give a residue which is taken up in 40 cm$^3$ of distilled water and 20 cm$^3$ of dichloromethane. After addition of sodium chloride, the aqueous phase is separated after settling and then extracted with twice 20 cm$^3$ of dichloromethane. The organic phases are combined, dried over magnesium sulfate, filtered and then concentrated to dryness under reduced pressure (2.7 kPa) to give 1 g of a brown solid which is purified by flash chromatography [eluent: dichloromethane-methanol (95-5 by volume)]. 650 mg of a product are thus obtained, which product is stirred in diethyl ether for one hour, filtered and then dried at 20° C. (90 Pa), to give 413 mg of (16R)-16-deoxo-16-fluoro-14-O-{4-[4-(pyrrolidin-1-ylcarbonylmethyl)piperazin-1-yl]butyryl}pristinamycin II$_B$, in the form of an off-white solid melting at 128° C.

$^1$H NMR spectrum (400 MHz, CDCl$_3$, δ in ppm): 0.96 (d, J=6.5 Hz: 3H); 1.00 (d, J=6.5 Hz: 3H); 1.10 (d, J=6.5 Hz: 3H); from 1.60 to 2.05 (mt: 11H); 1.88 (s: 3H); from 2.10 to 2.35 (mt: 2H); 2.32 (t, J=7.5 Hz: 2H); 2.40 (unresolved complex: 2H); from 2.50 to 2.70 (unresolved complex: 8H); 2.75 (mt: 1H); 2.99 (dt, J=17 and 6 Hz: 1H); 3.12 (s: 2H); 3.24 (mt: 1H); from 3.40 to 3.55 (mt: 5H); 3.86 (mt: 1H); 4.06 (mt: 1H); 4.53 (mt: 1H); 4.78 (dd, J=10 and 1.5 Hz: 1H); 4.82 (dd, J=9 and 3 Hz: 1H); 5.09 (decoupled doublet, J$_{HF}$=48 Hz: 1H); 5.29 (d, J=9 Hz: 1H); from 5.75 to 5.85 (mt: 1H); 5.75 (mt: 1H); 5.83 (dd, J=17 and 1.5 Hz: 1H); 6.05 (mt: 1H); 6.18 (d, J=16 Hz: 1H); 6.52 (dd, J=17 and 5 Hz: 1H); 8.12 (s: 1H).

EXAMPLE 30

(16R)-16-Deoxo-16-fluoro-14-O-[5-(morpholin-4-yl)pentanoyl]pristinamycin II$_B$ methanesulfonate 11 cm$^3$ of a 0.1 N ethanolic methanesulfonic acid solution are added, at 20° C., to 0.79 g of (16R)-16-deoxo-16-fluoro-14-O-[5-(morpholin-4-yl)pentanoyl]-pristinamycin II$_B$ in solution in 15 cm$^3$ of ethanol. After stirring for 20 minutes, the reaction mixture is concentrated to dryness under reduced pressure (2.7 kPa) to give a residue which is stirred in 10 cm$^3$ of ether. After filtration, rinsing of the solid with 5 cm$^3$ of diethyl ether and drying under reduced pressure (2.7 kPa) at 20° C., 0.89 g of (16R)-16-deoxo-16-fluoro-14-O-[5-(morpholin-4-yl)pentanoyl]pristinamycin II$_B$ methanesulfonate is obtained in the form of an off-white solid melting at around 120° C. (dec.).

$^1$H NMR spectrum (400 Mz, (CD$_3$)$_2$SO d6, δ in ppm): 0.85 (d, J=6.5 Hz: 3H); 0.94 (d, J=6.5 Hz: 3H); 1.03 (d, J=6.5 Hz: 3H); from 1.45 to 1.70 (mt: 5H); from 1.70 to 2.25 (mt: 6H); 1.77 (s: 3H); 2.32 (s: 3H); 2.39 (t, J=7 Hz: 2H); 2.77 (mt: 1H); from 2.95 to 3.50 (mt: 8H); from 3.50 to 3.70 (mt: 4H); 3.80 (mt: 1H); from 3.90 to 4.05 (mt: 3H); from 4.70 to 4.80 (mt: 2H); 5.09 (decoupled doublet, $J_{HF}$=48 Hz: 1H); 5.42 (d, J=9.5 Hz: 1H); 5.62 (mt: 1H); 5.75 (mt: 1H); 5.80 (broad d, J=16 Hz: 1H); 6.18 (d, J=16 Hz: 1H); 6.62 (dd, J=16 and 4 Hz: 1H); 8.15 (mt: 1H); 8.52 (s: 1H); 9.46 (broad unresolved complex: 1H).

(16R)-16-Deoxo-16-fluoro-14-O-[5-(morpholin-4-yl) pentanoyl]pristinamycin $II_B$ may be prepared in the following manner:

0.46 g of sodium iodide and 0.54 cm$^3$ of morpholine are added, at 20° C., to 2 g of (16R)-16-deoxo-16-fluoro-14-O-(5-chloropentanoyl)pristinamycin $II_B$ in solution in 30 cm$^3$ of tetrahydrofuran. After stirring for 27 hours under reflux, an additional 0.54 cm$^3$ of morpholine is added. After stirring for an additional 16 hours under reflux, 1 cm$^3$ of dimethylformamide and 0.54 cm$^3$ of morpholine are added. After stirring for another 24 hours under reflux, the reaction mixture is diluted with 20 cm$^3$ of dichloromethane and washed with 50 cm$^3$ of water. The organic phase is decanted off and the aqueous phase is extracted with 50 cm$^3$ of dichloromethane. The organic phases are combined, washed with three times 150 cm$^3$ of water, dried over magnesium sulfate, filtered and then concentrated to dryness under reduced pressure (2.7 kPa) to give 2 g of a residue which is purified by flash chromatography [eluent: dichloromethane/methanol/acetonitrile (92/4/4 by volume)]. After stirring in pentane, filtration and drying (2.7 kPa) at 20° C., 0.81 g of (16R)-16-deoxo-16-fluoro-14-O-[5-(morpholin4-yl)pentanoyl]pristinamycin $II_B$ is thus obtained in the form of a beige solid.

$^1$H NMR spectrum (400 MHz, CDCl$_3$, δ in ppm): 0.96 (d, J=6.5 Hz: 3H); 1.00 (d, J=6.5 Hz: 3H); 1.10 (d, J=6.5 Hz: 3H); 1.52 (mt: 2H); from 1.55 to 2.05 (mt: 7H); 1.89 (s: 3H); from 2.10 to 2.35 (mt: 2H); 2.32 (mt: 4H); 2.42 (unresolved complex: 4H); 2.76 (mt: 1H); 2.99 (dt, J=17 and 6 Hz: 1H); 3.24 (mt: 1H); 3.48 (mt: 1H); 3.72 (t, J=5 Hz: 4H); 3.86 (mt: 1H); 4.07 (mt: 1H); 4.53 (mt: 1H); 4.78 (dd, J=10 and 2 Hz: 1H); 4.82 (dd, J=9 and 3 Hz: 1H); 5.11 (decoupled doublet, $J_{HF}$=48 Hz: 1H); 5.30 (d, J=9 Hz: 1H); from 5.70 to 5.85 (mt: 2H); 5.82 (dd, J=16.5 and 2 Hz: 1H); 5.96 (mt: 1H); 6.19 (d, J=16 Hz: 1H); 6.51 (dd, J=16.5 and 5 Hz: 1H); 8.12 (s: 1H).

(16R)-16-Deoxo-16-fluoro-14-O-(5-chloropentanoyl) pristinamycin $II_B$ may be prepared in the following manner:

2.1 cm$^3$ of triethylamine, 2 cm$^3$ of 5-chloropentanoyl chloride and 0.18 g of 4-dimethylaminopyridine are added, at 28° C., to 4 g of (16R)-16-deoxo-16-fluoropristinamycin $II_B$ (prepared as described in Example 1) in solution in 100 cm$^3$ of dichloromethane. After stirring for 2 hours at 28° C., the reaction mixture is poured over 100 cm$^3$ of water. The organic phase is decanted off and the aqueous phase is extracted with 100 cm$^3$ of dichloromethane. The organic phases are combined, washed with twice 200 cm$^3$ of water, dried over magnesium sulfate, filtered and then concentrated to dryness under reduced pressure (2.7 kPa) to give 6 g of a brown solid which is purified by flash chromatography [eluent: dichloromethane/methanol (98/2 by volume)]. After stirring in pentane, filtration and drying (2.7 kPa) at 20° C., 3.77 g of (16R)-16-deoxo-16-fluoro-14-O-(5-chloropentanoyl)pristinamycin $II_B$ are thus obtained in the form of a white solid.

$^1$H NMR spectrum (400 MHz, CDCl$_3$, δ in ppm): 0.96 (d, J=6.5 Hz: 3H); 1.00 (d, J=6.5 Hz: 3H); 1.10 (d, J=6.5 Hz: 3H); from 1.65 to 2.05 (mt: 9H); 1.89 (s: 3H); 2.15 (mt: 1H); 2.24 (mt: 1H); 2.33 (t, J=7 Hz: 2H); 2.76 (mt: 1H); 2.99 (mt: 1H); 3.24 (mt: 1H); 3.49 (mt: 1H); 3.55 (t, J=7 Hz: 2H); 3.86 (mt: 1H); 4.06 (mt: 1H); 4.52 (mt: 1H); 4.78 (dd, J=10 and 2 Hz: 1H); 4.82 (dd, J=9 and 3 Hz: 1H); 5.11 (decoupled doublet, $J_{HF}$=48 Hz: 1H); 5.30 (d, J=9 Hz: 1H); from 5.75 to 5.85 (mt: 1H); 5.76 (mt: 1H); 5.82 (dd, J=17 and 2 Hz: 1H); 5.96 (mt: 1H); 6.19 (d, J=16 Hz: 1H); 6.51 (dd, J=17 and 5 Hz: 1H); 8.13 (s: 1H).

EXAMPLE 31

(16R)-16-Deoxo-16-fluoro-14-O-[5-(imidazol-1-yl) pentanoyl]pristinamycin $II_B$ methanesulfonate 10.2 cm$^3$ of a 0.095 N ethanolic methanesulfonic acid solution are added, at 20° C., to 0.66 g of (16R)-16-deoxo-16-fluoro-14-O-[5-(imidazol-1-yl)pentanoyl]pristinamycin $II_B$ in solution in 10 cm$^3$ of ethanol. After stirring for 10 minutes, the reaction mixture is concentrated to dryness under reduced pressure (2.7 kPa) to give a residue which is stirred in 20 cm$^3$ of ether. After filtration, washing of the solid with 5 cm$^3$ of diethyl ether and drying under reduced pressure (2.7 kPa), 0.712 g of (16R)-16-deoxo-16-fluoro-14-O-[5-(imidazol-1-yl)pentanoyl]pristinamycin $II_B$ is obtained in the form of a yellow oil melting at around 126° C. (dec.).

$^1$H NMR spectrum (400 MHz, (CD$_3$)$_2$SO d6, δ in ppm): 0.85 (d, J=6.5 Hz: 3H); 0.94 (d, J=6.5 Hz: 3H); 1.03 (d, J=6.5 Hz: 3H); from 1.40 to 1.60 (mt: 3H); from 1.70 to 2.30 (mt: 8H); 1.76 (s: 3H); 2.32 (s: 3H); 2.37 (t, J=7 Hz: 2H); 2.77 (mt: 1H); from 3.10 to 3.40 (mt: 2H); 3.58 (mt: 1H); 3.67 (mt: 1H); 3.80 (mt: 1H); 3.97 (mt: 1H); 4.21 (t, J=7 Hz: 2H); from 4.65 to 4.80 (mt: 2H); 5.08 (decoupled doublet, $J_{HF}$=48 Hz: 1H); 5.40 (d, J=9 Hz: 1H); 5.61 (mt: 1H); 5.73 (mt: 1H); 5.80 (broad d, J=16 Hz: 1H); 6.18 (d, J=16 Hz: 1H); 6.63 (dd, J=16 and 4 Hz: 1H); 7.72 (broad s: 1H); 7.80 (broad s: 1H); 8.15 (t, J=6 Hz: 1H); 8.52 (s: 1H); 9.14 (broad s: 1H).

(16R)-16-Deoxo-16-fluoro-14-O-[5-(imidazol-1-yl)pentanoyl]pristinamycin $II_B$ may be prepared in the following manner:

0.29 g of imidazole and 0.32 g of sodium iodide are added, at 20° C., to 1.4 g of (16R)-16-deoxo-16-fluoro-14-O-(5-chloropentanoyl)pristinamycin $II_B$ (prepared as described in Example 30) in solution in 20 cm$^3$ of tetrahydrofuran. After stirring for 20 hours under reflux, 1 cm$^3$ of dimethylformamide and 0.29 g of imidazole are added. After stirring for an additional 8.5 hours under reflux, 0.29 g of imidazole is added. After stirring for another 15.5 hours under reflux, the reaction mixture is diluted with 50 cm$^3$ of dichloromethane and then washed with 100 cm$^3$ of water. The organic phase is decanted off and the aqueous phase is extracted with 50 cm$^3$ of dichloromethane. The organic phases are combined, dried over magnesium sulfate, filtered and then concentrated to dryness under reduced pressure (2.7 kPa) to give 1.6 g of an orange-colored solid which is purified by two successive flash chromatographies [eluent: dichloromethane/methanol (97/3 by volume)]. After stirring in ethyl ether, filtration and drying (2.7 kPa) at 20° C., 0.66 g of (16R)-16-deoxo-16-fluoro-14-O-[5-(imidazol-1-yl) pentanoyl]pristinamycin $II_B$ is thus obtained in the form of a yellow solid.

$^1$H NMR spectrum (400 MHz, CDCl$_3$, δ in ppm): 0.96 (d, J=6.5 Hz: 3H); 1.00 (d, J=6.5 Hz: 3H); 1.11 (d, J=6.5 Hz: 3H); from 1.60 to 2.05 (mt: 9H); 1.90 (s: 3H); from 2.10 to 2.25 (mt: 2H); 2.31 (t, J=7 Hz: 2H); 2.76 (mt: 1H); 3.00 (mt: 1H); 3.25 (dt, J=17 and 5.5 Hz: 1H); 3.51 (mt: 1H); 3.84 (mt:

1H); 3.94 (t, J=7 Hz: 2H); 4.06 (mt: 1H); 4.56 (mt: 1H); from 4.75 to 4.90 (mt: 2H); 5.06 (decoupled doublet, $J_{HF}$=48 Hz: 1H); 5.24 (d, J=9 Hz: 1H); from 5.75 to 5.90 (mt: 2H); 5.90 (dd, J=16 and 1.5 Hz: 1H); 6.17 (d, J=15 Hz: 1H); 6.52 (mt: 1H); 6.57 (dd, J=16 and 5 Hz: 1H); 6.89 (s: 1H); 7.06 (s: 1H); 7.45 (s: 1H); 8.10 (s: 1H).

EXAMPLE 32

(16R)-16-Deoxo-16-fluoro-14-O-{5-[4-(pyrrolidin-1-ylcarbonylmethyl)piperazin-1-yl]pentanoyl}pristinamycin II$_B$ 1.1 g of (pyrrolidine-1-ylcarbonylmethyl)piperazine and 0.42 g of sodium iodide are added, at 20° C., to 1.8 g of (16R)-16-deoxo-16-fluoro-14-O-(5-chloro-pentanoyl)pristinamycin II$_B$ (prepared as described in Example 30) in solution in 20 cm$^3$ of dimethylformamide. After stirring for 27.5 hours at 50° C., 0.55 g of (pyrrolidin-1-ylcarbonylmethyl)piperazine is added. After stirring for an additional 27.5 hours at 54° C., the reaction mixture is concentrated to dryness under reduced pressure (2.7 kPa) to give a residue which is diluted in 100 cm$^3$ of dichloromethane. The solution obtained is washed with four times 300 cm$^3$ of water. The organic phase is dried over magnesium sulfate, filtered and concentrated to dryness under reduced pressure (2.7 kPa) to give 1.61 g of a yellow solid which is purified by flash chromatography [eluent: dichloromethane/methanol (95/5 by volume)]. After stirring in pentane, filtration and drying (2.7 kPa), 0.726 g of (16R)-16-deoxo-16-fluoro-14-O-{5-[4-(pyrrolidine-1-ylcarbonylmethyl)piperazin-1-yl]pentanoyl}pristinamycin II$_B$ is thus obtained in the form of a beige solid melting at around 100° C. (dec.).

$^1$H NMR spectrum (400 MHz, CDCl$_3$, δ in ppm): 0.96 (d, J=6.5 Hz: 3H); 1.00 (d, J=6.5 Hz: 3H); 1.09 (d, J=6.5 Hz: 3H); 1.51 (mt: 2H); from 1.55 to 1.80 (mt: 3H); from 1.75 to 2.05 (mt: 8H); 1.88 (s: 3H); 2.15 (mt: 1H); 2.23 (mt: 1H); from 2.25 to 2.40 (mt: 4H); 2.50 (unresolved complex: 4H); 2.58 (unresolved complex: 4H); 2.76 (mt: 1H); 2.99 (dt, J=17 and 6 Hz: 1H); 3.11 (s: 2H); 3.24 (mt: 1H); from 3.45 to 3.55 (mt: 5H); 3.86 (mt: 1H); 4.06 (mt: 1H); 4.53 (mt: 1H); 4.78 (dd, J=10 and 2 Hz: 1H); 4.82 (dd, J=9 and 3 Hz: 1H); 5.09 (decoupled doublet, $J_{HF}$=48 Hz: 1H); 5.30 (d, J=9 Hz: 1H); from 5.75 to 5.90 (mt: 1H); 5.75 (mt: 1H); 5.83 (dd, J=17 and 1.5 Hz: 1H); 6.04 (mt: 1H); 6.19 (d, J=16 Hz: 1H); 6.53 (dd, J=17 and 5 Hz: 1H); 8.12 (s: 1H).

EXAMPLE 33

(16R)-16-Deoxo-16-fluoro-14-O-[(RR,SS)-trans-2-(morpholinomethyl)-1-cyclopropanecarbonyl]pristinamycin II$_B$, mixture of two diastereoisomers in the proportions 50/50

1.1 g of (RR,SS)-trans-2-(morpholinomethyl)-1-cyclopropanecarboxylic acid, 1.24 g of N,N'-dicyclohexylcarbodiimide and 0.73 g of 4-dimethylaminopyridine are added, at 20° C., under an argon atmosphere, to 2.1 g of (16R)-16-deoxo-16-fluoro-pristinamycin II$_B$ (prepare as described in Example 1) in solution in 80 cm$^3$ of dichloromethane. After stirring for 16 hours, the reaction mixture is filtered to remove the insoluble matter and then concentrated to dryness under reduced pressure (2.7 kPa) to give 4.2 g of a residue which is purified by flash chromatography [eluent: dichloromethane/methanol gradient (98/2 to 95/5 by volume)]. A solid is obtained which is stirred in diisopropyl ether, filtered and dried (2.7 kPa) at 20° C., to give 1.5 g of (16R)-16-deoxo-16-fluoro-14-O-[(RR,SS)-trans-2-(morpholinomethyl)-1-cyclo-propanecarbonyl]pristinamycin II$_B$, mixture of two diastereoisomers in the proportions 50/50, in the form of a whitish powder.

$^1$H NMR spectrum (400 MHz, CDCl$_3$, δ in ppm). The presence of two diastereoisomers in the proportions 50-50 is observed: 0.77 (mt: 1H); 0.96 (d, J=6.5 Hz: 3H); 1.00 (d, J=6.5 Hz: 3H); 1.09 (d, J=6.5 Hz: 3H); 1.24 (mt: 1H); 1.41 (mt: 1H); 1.52 (mt: 1H); from 1.60 to 2.05 (mt: 5H); 1.87 (s: 3H); from 2.05 to 2.45 (mt: 4H); 2.50 (unresolved complex: 4H); 2.76 (mt: 1H); 2.99 (mt: 1H); 3.24 (mt: 1H); 3.49 (mt: 1H); 3.73 (t, J=5 Hz: 4H); 3.84 (mt: 1H); 4.06 (mt: 1H); 4.53 (mt: 1H); from 4.75 to 4.85 (mt: 2H); 5.09 (decoupled doublet, $J_{HF}$=48 Hz: 1H); 5.30 (mt: 1H); from 5.70 to 5.85 (mt: 3H); 5.96 and 6.03 (2 mts: 1H in total); 6.19 (d, J=16 Hz: 1H); 6.51 (mt: 1H); 8.12 (s: 1H).

(RR,SS)-trans-2-(Morpholinomethyl)-1-cyclopropanecarboxylic acid may be prepared in the following manner:

10 cm$^3$ of a 1 N aqueous sodium hydroxide solution are added, at 20° C., to 1.0 g of ethyl (RR,SS)-trans-2-(morpholinomethyl)-1-cyclopropanecarboxylate in solution in 50 cm$^3$ of ethanol. After stirring for 2 hours at 80° C., the ethanol is concentrated under reduced pressure (2.7 kPa) and the residual aqueous phase is washed with 50 cm$^3$ of ethyl acetate. The aqueous phase is adjusted to pH 6 by addition of a 1 N aqueous hydrochloric acid solution and then concentrated to dryness under reduced pressure (2.7 kPa). Twice, the residue is covered with 50 cm$^3$ of toluene and concentrated to dryness under reduced pressure (2.7 kPa). The residue is taken up in 50 cm$^3$ of ethanol at 50° C., the insoluble matter is removed by filtration and the filtrate is concentrated under reduced pressure (2.7 kPa). 0.9 g of (RR,SS)-trans-2-(morpholinomethyl)-1-cyclopropanecarboxylic acid is thus obtained in the form of a yellow oil.

$^1$H NMR spectrum (400 MHz, CDCl$_3$, δ in ppm): 0.68 (mtt: 1H); 1.20 (mt: 1H); 1.46 (mt: 1H); 1.56 (mt: 1H); 2.28 (dd, J=13 and 8 Hz: 1H); 2.60 (dd, J=13 and 5 Hz: 1H); 2.66 (unresolved complex: 2H); 2.77 (unresolved complex: 2H); 3.78 (t, J=5 Hz: 4H).

Ethyl (RR,SS)-trans-2-(morpholinomethyl)-1-cyclopropanecarboxylate may be prepared in the following manner:

1.74 cm$^3$ of morpholine and 6.36 g of sodium tris(aceto-O)hydridoborate are added, at 20° C., under an argon atmosphere, to 2.82 g of ethyl (RR,SS)-trans-2-formyl-1-cyclopropanecarboxylate in solution in 100 cm$^3$ of dichloromethane. After stirring for four hours, 100 cm$^3$ of distilled water are added. After stirring, the organic phase is decanted off and then washed with 100 cm$^3$ of distilled water. The organic phase is dried over magnesium sulfate, filtered and then concentrated to dryness under reduced pressure (2.7 kPa). 1.1 g of ethyl (RR,SS)-trans-2-(morpholinomethyl)-1-cyclo-propanecarboxylate are thus obtained in the form of a yellow oil.

$^1$H NMR spectrum (400 MHz, CDCl$_3$, δ in ppm): 0.76 (mt: 1H); from 1.20 to 1.35 (mt: 4H); 1.44 (mt: 1H); 1.54 (mt: 1H); 2.31 (dd, J=13 and 7 Hz: 1H); 2.36 (dd, J=13 and 7 Hz: 1H); 2.50 (broad t, J=5 Hz: 4H); 3.73 (t, J=5 Hz :4H); 4.13 (mt: 2H).

EXAMPLE 34

(16R)-16-Deoxo-16-fluoro-14-O-[6-(imidazol-1-yl)hexanoyl]pristinamycin II$_B$ 0.34 g of imidazole and a few crystals of sodium iodide are added, at 20° C., to 1.42 g of (16R)-16-deoxo-16-fluoro-14-O-(6-bromohexanoyl)pristinamycin II$_B$ in solution in 7 cm³ of dimethyl sulfoxide. After stirring for 2 hours at 53° C. and then for 16 hours at 20° C., the reaction mixture is poured over 35 cm³ of water and filtered on sintered glass. The insoluble matter is washed with water and dissolved in 70 cm³ of ethyl acetate. The resulting solution is extracted with 25 cm³ of a 0.1 N aqueous hydrochloric acid solution. The aqueous phase is decanted off, extracted with 10 cm³ of ethyl acetate and then neutralized with 0.5 cm³ of a 5 N aqueous sodium hydroxide solution. The aqueous phase is then extracted with twice 25 cm³ of ethyl acetate. The organic phases are combined, dried over magnesium sulfate, filtered and then concentrated to dryness under reduced pressure (2.7 kPa) to give 1 g of a pale yellow solid which is purified by flash chromatography (eluent: dichloromethane/methanol/acetonitrile (88/6/6 by volume)]. 0.59 g of a white solid is obtained, which solid is taken up in 5 cm³ of dichloromethane. The organic phase is filtered on Celite®. The Celite® is rinsed with dichloromethane. The filtrate is concentrated to dryness under reduced pressure (2.7 kPa) at 20° C., to give 0.58 g of (16R)-16-deoxo-16-fluoro-14-O-[6-(imidazol-1-yl)hexanoyl]pristinamycin $II_B$, in the form of a white solid melting at around 90° C. (dec.).

¹H NMR spectrum (400 MHz, $CDCl_3$, 67 in ppm): 0.95 (d, J=6.5 Hz: 3H); 0.99 (d, J=6.5 Hz: 3H); 1.10 (d, J=6.5 Hz: 3H); 1.27 (mt: 2H); from 1.60 to 2.10 (mt: 5H); 1.63 (mt: 2H); 1.78 (mt: 2H); 1.88 (s: 3H); from 2.10 to 2.25 (mt: 2H); 2.27 (t, J=7 Hz: 2H); 2.75 (mt: 1H); 3.00 (mt: 1H); 3.25 (dt, J=17 and 5 Hz: 1H); 3.51 (mt: 1H); 3.82 (mt: 1H); 3.94 (t, J=7 Hz: 2H); 4.08 (mt: 1H); 4.58 (mt: 1H); from 4.75 to 4.85 (mt: 2H); 5.07 (decoupled doublet, $J_{HF}$=48 Hz: 1H); 5.20 (d, J=9 Hz: 1H); from 5.75 to 5.85 (mt: 2H); 5.90 (dd, J=16 and 1.5 Hz: 1H); 6.18 (d, J=16 Hz: 1H); 6.56 (dd, J=16 and 5 Hz: 1H); 6.77 (mt: 1H); 6.90 (s: 1H); 7.10 (s: 1H); 7.45 (s: 1H); 8.12 (s: 1H).

(16R)-16-Deoxo-16-fluoro-14-O-(6-bromohexanoyl) pristinamycin $II_B$ may be prepared in the following manner:

1.7 cm³ of triethylamine and 1.8 cm³ of 6-bromohexanoyl chloride are added, at 28° C., to 5.32 g of (16R)-16-deoxo-16-fluoropristinamycin $II_B$ (prepared as described in Example 1) in solution in 150 cm³ of dichloromethane. After stirring for 21.5 hours at 23° C., 0.43 cm³ of triethylamine and 0.45 cm³ of 6-bromohexanoyl chloride are added. After stirring for an additional 21 hours at 28° C., the reaction mixture is poured over 50 cm³ of water. The organic phase is decanted off, dried over magnesium sulfate, filtered and then concentrated to dryness under reduced pressure (2.7 kPa) to give 8.05 g of a brown solid which is purified by flash chromatography [eluent: dichloromethane/methanol/ acetonitrile (96/2/2 by volume)]. 5.6 g of (16R)-16-deoxo-16-fluoro-14-O-(6-bromohexanoyl)pristinamycin $II_B$ are thus obtained in the form of a pale yellow solid.

¹H NMR spectrum (400 MHz, $CDCl_3$, δ in ppm): 0.96 (d, J=6.5 Hz: 3H); 1.00 (d, J=6.5 Hz: 3H); 1.09 (d, J=6.5 Hz: 3H); 1.48 (mt: 2H); from 1.60 to 2.05 (mt: 9H); 1.88 (s: 3H); 2.15 (mt: 1H); 2.24 (mt: 1H); 2.31 (t, J=7.5 Hz: 2H); 2.76 (mt: 1H); 2.99 (mt: 1H); 3.24 (mt: 1H); 3.41 (t, J=7 Hz: 2H); 3.49 (mt: 1H); 3.86 (mt: 1H); 4.06 (mt: 1H); 4.53 (mt: 1H); 4.78 (dd, J=10 and 2 Hz: 1H); 4.82 (dd, J=9 and 3 Hz: 1H); 5.11 (decoupled doublet, $J_{HF}$=48 Hz: 1H); 5.31 (d, J=9 Hz: 1H); from 5.75 to 5.85 (mt: 1H); 5.75 (mt: 1H); 5.82 (dd, J=17 and 2 Hz: 1H); 5.95 (mt: 1H); 6.19 (d, J=16 Hz: 1H); 6.51 (dd, J=17 and 4 Hz: 1H); 8.13 (s: 1H).

EXAMPLE 35

(16R)-16-Deoxo-16-fluoro-14-O-[6-(4-methylpiperazin-1-yl)hexanoyl]pristinamycin $II_B$ 0.67 cm³ of N-methylpiperazine is added, at 20° C., to 1.42 g of (16R)-16-deoxo-16-fluoro-14-O-(6-bromohexanoyl)pristinamycin $II_B$ (prepared as described in Example 34) solution in 7 cm³ of dimethyl sulfoxide. After stirring for 0.5 hour at 60° C., the reaction mixture is poured over 35 cm³ of ice-cold water and extracted with 50 cm³ of dichloromethane. The organic phase is washed with 25 cm³ of a saturated aqeuous sodium chloride solution, dried over magnesium sulfate, filtered and then concentrated to dryness under reduced pressure (2.7 kPa) to give 1.2 g of an orange-colored solid which is dissolved in 30 cm³ of ethyl acetate. The resulting solution is extracted successively with 20 cm³ of a 0.1 N aqueous hydrochloric acid solution and 10 cm³ of water. The aqueous phases are combined and neutralized with 0.4 cm³ of a 5 N aqueous sodium hydroxide solution. The aqueous phase is extracted with twice 25 cm³ of dichloromethane. The organic phases are combined, dried over magnesium sulfate, filtered and then concentrated to dryness under reduced pressure (2.7 kPa) to give 0.94 g of a yellow solid which is purified by flash chromatography [eluent: dichloromethane/methanol (90/10 by volume)]. 0.27 g of a white solid is obtained, which solid is taken up in 5 cm³ of dichloromethane. The organic phase is filtered on Celite®. The Celite® is rinsed with dichloromethane. The filtrate is concentrated to dryness under reduced pressure (2.7 kPa) at 20° C., to give 0.26 g of (16R)-16-deoxo-16-fluoro-14-O-[6-(4-methylpiperazin-1-yl)hexanoyl]pristinamycin $II_B$, in the form of a white solid melting at around 95° C. (dec.).

¹H NMR spectrum (400 MHz, $CDCl_3$, δ in ppm): 0.96 (d, J=6.5 Hz: 3H); 1.00 (d, J=6.5 Hz: 3H); 1.09 (d, J=6.5 Hz: 3H); 1.33 (mt: 2H); 1.51 (mt: 2H); from 1.55 to 2.05 (mt: 7H); 1.88 (s: 3H); from 2.10 to 2.65 (mt: 14H); 2.29 (s: 3H); 2.76 (mt: 1H); 2.99 (mt: 1H); 3.24 (mt: 1H); 3.48 (mt: 1H); 3.86 (mt: 1H); 4.06 (mt: 1H); 4.53 (mt: 1H); 4.78 (dd, J=10 and 2 Hz: 1H); 4.82 (dd, J=9 and 3 Hz: 1H); 5.10 (decoupled doublet, $J_{HF}$=48 Hz: 1H); 5.30 (d, J=9 Hz: 1H); from 5.75 to 5.85 (mt: 1H); 5.75 (mt: 1H); 5.82 (dd, J=17 and 2 Hz: 1H); 5.98 (mt: 1H); 6.19 (d, J=16 Hz: 1H); 6.52 (dd, J=17 and 5 Hz: 1H); 8.13 (s: 1H).

EXAMPLE 36

(16R)-16-Deoxo-16-fluoro-14-O-{6-[4-(pyrrolidin-1-ylcarbonylmethyl)piperazin-1-yl] hexanoyl}pristinamycin $II_B$ 1.18 g of (pyrrolidin-1-ylcarbonylmethyl)piperazine are added, at 20° C., to 1.35 g of (16R)-16-deoxo-16-fluoro-14-O-(6-bromohexanoyl)pristinamycin $II_B$ (prepared as described in Example 34) in solution in 7 cm³ of dimethyl sulfoxide. After stirring for 3 hours at 60° C., the reaction mixture is poured over 35 cm³ of ice-cold water and then extracted with twice 25 cm³ of ethyl acetate. The organic phases are combined, dried over magnesium sulfate, filtered and then concentrated to dryness under reduced pressure (2.7 kPa) to give 1.53 g of a gummy residue which is purified by flash chromatography [eluent: dichloromethane/methanol (90/10 by volume)]. 0.96 g of a sticky gum is obtained, which gum is taken up in 10 cm³ of dichloromethane. The solution is filtered on CELITE®. The CELITE® is rinsed with dichloromethane. The filtrate is concentrated to dryness under reduced pressure (2.7 kPa) to give a gum which is stirred successively in diethyl ether and pentane. After filtration and then drying under reduced pressure (2.7 kPa), 0.78 g of (16R)-16-deoxo-16-fluoro-14-O-{6-[4-(pyrrolidin-1-ylcarbonylmethyl)piperazin-1-yl] hexanoyl}pristinamycin II$_B$ is obtained in the form of a yellow solid melting at around 80° C. (dec.).

$^1$H NMR spectrum (400 MHz, CDCl$_3$, δ in ppm): 0.96 (d, J=6.5 Hz: 3H); 1.00 (d, J=6.5 Hz: 3H); 1.09 (d, J=6.5 Hz: 3H); 1.32 (mt: 2H); 1.50 (mt: 2H); from 1.60 to 2.05 (mt: 11H); 1.88 (s: 3H); from 2.10 to 2.40 (mt: 6H); 2.50 (unresolved complex: 4H); 2.59 (unresolved complex: 4H); 2.76 (mt: 1H); 2.99 (mt: 1H); 3.12 (s: 2H); 3.24 (mt: 1H); from 3.40 to 3.55 (mt: 5H); 3.86 (mt: 1H); 4.05 (mt: 1H); 4.52 (mt: 1H); 4.78 (dd, J=10 and 2 Hz: 1H); 4.82 (dd, J=9 and 3 Hz: 1H); 5.10 (decoupled doublet, J$_{HF}$=48 Hz: 1H); 5.30 (d, J=9 Hz: 1H); from 5.75 to 5.90 (mt: 1H); 5.75 (mt: 1H); 5.82 (dd, J=17 and 2 Hz: 1H); 6.02 (mt: 1H); 6.19 (d, J=16 Hz: 1H); 6.52 (dd, J=17 and 5 Hz: 1H); 8.13 (s: 1H).

EXAMPLE 37

(16R)-16-Deoxo-16-fluoro-14-O-[7-(imidazol-1-yl) heptanoyl]pristinamycin II$_B$ methanesulfonate 2.7 cm$^3$ of a 1 N ethanolic methanesulfonic acid solution are added, at 20° C., to 1.96 g of (16R)-16-deoxo-16-fluoro-14-O-[7-(imidazol-1-yl)heptanoyl]pristinamycin II$_B$ in solution in 10 cm$^3$ of ethanol. After stirring for 10 minutes, the reaction mixture is concentrated to dryness under reduced pressure (2.7 kPa) to give a residue which is stirred in 10 cm$^3$ of ether. After filtration, washing of the solid with 5 cm$^3$ of diethyl ether and drying under reduced pressure (2.7 kPa), 2.13 g of (16R)-16-deoxo-16-fluoro-14-O-[7-(imidazol-1-yl)heptanoyl]pristinamycin II$_B$ methanesulfonate are obtained in the form of a cream-colored solid melting at around 110° C. (dec.).

$^1$H NMR spectrum (400 MHz, CDCl$_3$, δ in ppm): 0.95 (d, J=6.5 Hz: 3H); 0.98 (d, J=6.5 Hz: 3H); 1.09 (d, J=6.5 Hz: 3H); from 1.25 to 1.45 (mt: 4H); from 1.55 to 2.05 (mt: 9H); 1.88 (s: 3H); from 2.10 to 2.30 (mt: 2H); 2.28 (t, J=7.5 Hz: 2H); 2.76 (mt: 1H); 2.85 (s: 3H); 3.00 (dt, J=17 and 6 Hz: 1H); 3.24 (mt: 1H); 3.51 (mt: 1H); 3.84 (mt: 1H); 4.05 (mt: 1H); 4.18 (t, J=7.5 Hz: 2H); 4.49 (mt: 1H); 4.78 (dd, J=10 and 2 Hz: 1H); 4.82 (dd, J=9 and 3 Hz: 1H); 5.09 (decoupled doublet, J$_{HF}$=48 Hz: 1H); 5.28 (d, J=9.5 Hz: 1H); from 5.70 to 5.85 (mt: 2H); 5.84 (dd, J=16 and 2 Hz: 1H); 6.13 (mt: 1H); 6.18 (d, J=16 Hz: 1H); 6.53 (dd, J=16 and 5 Hz: 1H); 7.13 (s: 1H); 7.41 (s: 1H); 8.12 (s: 1H); 8.92 (s: 1H).

(16R)-16-Deoxo-16-fluoro-14-O-[7-(imidazol-1 -yl)heptanoyl]pristinamycin II$_B$ may be prepared in the following manner:)

1.49 g of N,N'-dicyclohexylcarbodiimide, 0.075 g of 4-dimethylaminopyridine, 1.68 g of 7-(imidazol-1-yl)heptanoic acid hydrochloride and 1 cm$^3$ of triethylamine are added, at 23° C., to 3.2 g of (16R)-16-deoxo-16-fluoropristinamycin II$_B$ (prepared as described in Example 1) in solution in 100 cm$^3$ of dichloromethane. After stirring for 84 hours at 23° C., the reaction mixture is filtered and the insoluble matter is rinsed with dichloromethane. The filtrate is concentrated to dryness under reduced pressure (2.7 kPa) to give an oily residue which is diluted in 100 cm$^3$ of ethyl acetate. The resulting solution is washed successively with twice 40 cm$^3$ of water and 40 cm$^3$ of a saturated aqueous sodium chloride solution and then extracted with 60 cm$^3$ of a 0.1 N aqueous hydrochloric acid solution. The acidic aqueous phase is then extracted with 20 cm$^3$ of ethyl acetate, and adjusted to pH 8 by addition of 6 cm$^3$ of a 1 N aqueous sodium hydroxide solution and then extracted with twice 40 cm$^3$ of ethyl acetate. The organic phases are combined, washed with a saturated aqueous sodium chloride solution, dried over magnesium sulfate, filtered and then concentrated to dryness under reduced pressure (2.7 kPa) to give 3.05 g of a pale yellow solid which is purified by flash chromatography [eluent: dichloromethane/methanol/acetonitrile (86/7/7 by volume)]. 2.58 g of a solid are obtained, which solid is taken up in 10 cm$^3$ of dichloromethane. This solution is filtered on Celite®. The Celite® is rinsed with dichloromethane. The filtrate is concentrated to dryness under reduced pressure (2.7 kPa) at 20° C., to give 2.58 g of (16R)-16-deoxo-16-fluoro-14-O-[7-(imidazol-1-yl)heptanoyl]pristinamycin II$_B$, in the form of a white solid melting at around 80° C. (dec.).

$^1$H NMR spectrum (400 MHz, CDCl$_3$, δ in ppm): 0.95 (d, J=6.5 Hz: 3H); 0.99 (d, J=6.5 Hz: 3H); 1.09 (d, J=6.5 Hz: 3H); from 1.25 to 1.40 (mt: 4H); from 1.55 to 2.05 (mt: 9H); 1.88 (s: 3H); from 2.10 to 2.30 (mt: 2H); 2.27 (t, J=7.5 Hz: 2H); 2.76 (mt: 1H); 2.99 (dt, J=17 and 6 Hz: 1H); 3.24 (mt: 1H); 3.48 (mt: 1H); 3.85 (mt: 1H); 3.93 (t, J=7.5 Hz: 2H); 4.06 (mt: 1H); 4.53 (mt: 1H); 4.78 (dd, J=10 and 2 Hz: 1H); 4.82 (dd, J=9 and 3 Hz: 1H); 5.09 (decoupled doublet, J$_{HF}$=48 Hz: 1H); 5.29 (d, J=9 Hz: 1H); from 5.70 to 5.85 (mt: 2H); 5.83 (dd, J=16.5 and 2 Hz: 1H); 6.17 (mt: 1H); 6.19 (d, J=15 Hz: 1H); 6.52 (dd, J=16.5 and 5 Hz: 1H); 6.90 (s: 1H); 7.06 (s: 1H); 7.45 (s: 1H); 8.12 (s: 1H).

7-(Imidazol-1-yl)heptanoic acid hydrochloride may be prepared according to Kinji Iizuka et al, J. Med. Chem., Vol. 24, No. 10, pages 1139 to 1148 (1981).

EXAMPLE 38

(16R)-16-Deoxo-16-fluoro-14-O-(4-methylpiperazin-1-yl)carbonylacetyl-pristinamycin II$_B$ 1.74 g of 4-methylpiperazin-1-ylcarbonylacetic acid, 1.44 g of N,N'-dicyclohexyl-carbodiimide and 0.09 g of 4-dimethylaminopyridine are added, at 20° C., under an argon atmosphere, to 2.5 g of (16R)-16-deoxo-16-fluoropristinamycin II$_B$ (prepared as described in Example 1) in solution in 100 cm$^3$ of dichloromethane. After stirring for 18 hours, the reaction mixture is supplemented with 50 cm$^3$ of dichloromethane, filtered to eliminate the insoluble matter and then washed with four times 50 cm$^3$ of distilled water. The organic phase is decanted off, dried over magnesium sulfate and then concentrated to dryness under reduced pressure (2.7 kPa). The residue (3.4 g) is purified by flash chromatography [eluent: dichloromethane/methanol gradient (97/3 and 92/8 by volume)]. A white solid is obtained which gives, after stirring in diethyl ether, filtration and drying (2.7 kPa), 1.3 g of (16R)-16-deoxo-16-fluoro-14-O-(4-methylpiperazin-1-yl)carbonylacetylpristinamycin II$_B$ in the form of a white solid.

$^1$H NMR spectrum (500 MHz, CDCl$_3$, δ in ppm): 0.96 (d, J=6.5 Hz: 3H); 1.01 (d, J=6.5 Hz: 3H); 1.10 (d, J=6.5 Hz: 3H); from 1.70 to 2.00 (mt: 5H); 1.89 (s: 3H); 2.15 (mt: 1H); from 2.25 to 2.35 (mt: 1H); 2.31 (s: 3H); 2.40 (mt: 4H); 2.76 (mt: 1H); 3.01 (dt, J=16 and 6 Hz: 1H); 3.23 (mt: 1H); from 3.40 to 3.55 (mt: 5H); 3.66 (mt: 2H); 3.87 (mt: 1H); 4.05 (mt: 1H); 4.53 (mt: 1H); 4.78 (broad d, J=10 Hz: 1H); 4.82 (dd, J=9 and 3 Hz: 1H); 5.14 (decoupled doublet, J$_{HF}$=48 Hz: 1H); 5.34 (d, J=9.5 Hz: 1H); 5.77 (mt: 1H); 5.82 (dd, J=16 and 2 Hz: 1H); 5.88 (dt, J=9.5 and 5 Hz: 1H); 5.95 (mt: 1H); 6.20 (d, J=16Hz: 1H); 6.51 (dd, J=16 and 4 Hz: 1H); 8.12 (s: 1H).

4-Methylpiperazin-1-ylcarbonylacetic acid may be prepared in the following manner:

23 cm$^3$ of a 0.1 N aqueous sodium hydroxide solution are added, at 20° C., to 4.5 g of ethyl 4-methylpiperazin-1-ylcarbonylacetate in solution in 100 cm$^3$ of ethanol. After stirring for 24 hours, the reaction mixture is concentrated to dryness under reduced pressure (2.7 kPa). The residue obtained is taken up in 50 cm$^3$ of distilled water and the solution is washed with four times 50 cm$^3$ of dichloromethane. The aqueous phase is brought to pH 5–6 by addition of a 1 N aqueous hydrochloric acid solution, extracted with twice 50 cm$^3$ of dichloromethane and then concentrated to dryness under reduced pressure (2.7 kPa). Three times, the residue is covered with 100 cm$^3$ of toluene and again dried under the same conditions. 4.6 g of a yellow pasty residue are obtained, which residue is stirred in 50 cm$^3$ of ethanol at around 60° C. The insoluble matter is removed by filtration and the filtrate is concentrated to dryness under reduced pressure (2.7 kPa). 3.5 g of 4-methylpiperazin-1-ylcarbonylacetic acid are thus obtained in the form of a hygroscopic sticky mass that is used as it is.

$^1$H NMR spectrum (300 Mz, (CD$_3$)$_2$SO d6, δ in ppm): 2.21 (s: 3H); 2.29 (t, J=5 Hz: 2H); 2.34 (t, J=5 Hz: 2H); from 3.30 to 3.50(mt: 4H); 3.39 (s: 2H).

Ethyl 4-methylpiperazin-1-ylcarbonylacetate may be prepared according to Morren H., Trolin S., Denayer R., Grivsky E., Bull. Soc. Chim. Belg. 1950, 59, 228–232.

EXAMPLE 39

(16R)-14-O-(4-Carboxybutyryl)-16-deoxo-16-fluoropristinamycin II$_B$ 258 mg of glutaric anhydride and 84.5 mg of 4-dimethylaminopyridine are added, at 20° C., to 400 mg of (16R)-16-deoxo-16-fluoropristinamycin II$_B$ (prepared as described in Example 1) in solution in 2 cm$^3$ of pyridine. After stirring for 20 hours, the pyridine is evaporated under reduced pressure (2.7 kPa) and the oil obtained is taken up in 20 cm$^3$ of ethyl acetate. The resulting solution is washed with twice 10 cm$^3$ of distilled water and then with a 0.1 N aqueous hydrochloric acid solution. The aqueous phase is extracted with ethyl acetate and then separated after settling. The organic phase is washed with distilled water and then with twice 2 cm$^3$ of a saturated sodium chloride solution. The organic phase is decanted off, dried over magnesium sulfate, filtered and then concentrated to dryness under reduced pressure (2.7 kPa), to give a light yellow solid which is stirred in 20 cm$^3$ of diethyl ether, filtered and then dried under reduced pressure (2.7 kPa). 363 mg of a solid are obtained, which solid is purified by flash chromatography [eluent: dichloromethane-methanol (97-3 by volume)] to give 100 mg of (16R)-14-O-(4-carboxybutyryl)-16-deoxo-16-fluoropristinamycin II$_B$ in the form of a white solid melting at 98° C.

$^1$H NMR spectrum (400 MHz, CDCl$_3$, δ in ppm): 0.96 (d, J=6.5 Hz: 3H); 1.01 (d, J=6.5 Hz: 3H); 1.10 (d, J=6.5 Hz: 3H); from 1.55 to 2.05 (mt: 7H); 1.89 (s: 3H); 2.17 (mt: 1H); 2.25 (mt: 1H); 2.37 (t, J=7 Hz: 2H); 2.42 (t, J=7 Hz: 2H); 2.77 (mt: 1H); 3.00 (td, J=17 and 6 Hz: 1H); 3.25 (mt: 1H); 3.50 (mt: 1H); 3.86 (mt: 1H); 4.08 (mt: 1H); 4.53 (mt: 1H); 4.79 (dd, J=10 and 1.5 Hz: 1H); 4.82 (dd, J=9 and 3 Hz: 1H); 5.13 (decoupled doublet, J$_{HF}$=48 Hz: 1H); 5.31 (d, J=9.5 Hz: 1H); from 5.75 to 5.90 (mt: 1H); 5.77 (mt: 1H); 5.83 (dd, J=17 and 2 Hz: 1H); 5.97 (mt: 1H); 6.19 (d, J=16 Hz: 1H); 6.53 (dd, J=17 and 5 Hz: 1H); 8.14 (s: 1H).

EXAMPLE 40

(16R)-16-Deoxo-16-fluoro-14-O-[3-(4-methylpiperazin-1-ylcarbonyl)propionyl]-pristinamycin II$_B$ hydrochloride A 3 N hydrochloric ether solution is added to 615 mg of (16R)-16-deoxo-16-fluoro-14-O-[3-(4-methylpiperazin-1-ylcarbonyl)propionyl]pristinamycin II$_B$ dissolved in 6 cm$^3$ of methyl isobutyl ketone until an abundant precipitate is obtained. The latter is filtered, rinsed with twice 2 cm$^3$ of methyl isobutyl ketone and then with three times 10 cm$^3$ of diethyl ether. After drying at 50° C. (90 Pa), 600 mg of (16R)-16-deoxo-16-fluoro-14-O-[3-(4-methylpiperazin-1-ylcarbonyl)propionyl]pristinamycin II$_B$ hydro-chloride in the form of a white powder melting at 160° C. are obtained.

(16R)-16-Deoxo-16-fluoro-14-O-[3-(4-methylpiperazin-1-ylcarbonyl)propionyl]-pristinamycin II$_B$ may be prepared in the following manner:

450 mg of 4-(4-methylpiperazin-1-yl)-4-oxobutyric acid, 1 g of (16R)-16-deoxo-16-fluoropristinamycin II$_B$ (prepared as described in Example 1), 470 mg of N,N'-dicyclohexylcarbodiimide, 140 mg of 4-dimethylaminopyridine and then 20 cm$^3$ of dichloromethane are added to a three-necked flask placed under nitrogen. The reaction is stirred at 20° C. for 48 hours. The reaction mixture is then diluted with 10 cm$^3$ of dichloromethane and then poured over 50 cm$^3$ of distilled water. The mixture obtained is filtered on cotton wool. The organic phase is decanted off and the aqueous phase is extracted with twice 5 cm$^3$ of dichloromethane. The organic phases are combined, dried over sodium sulfate, filtered and then concentrated to dryness under reduced pressure (2.7 kPa), to give 1.66 g of a mixture which is purified by flash chromatography [eluent: dichloromethane-methanol (95-5 by volume)]. 975 mg of a product are thus obtained, which product is stirred in 10 cm$^3$ of diethyl ether, filtered and dried, and then repurified by flash chromatography [eluent: ethyl acetate-methanol (93-7 by volume)]. The fractions are concentrated to give a solid which is taken up in 10 cm$^3$ of diethyl ether and stirred for 30 minutes. The white solid obtained is filtered, rinsed with diethyl ether and then dried at 50° C. (90 Pa) to give 500 mg of (16R)-16-deoxo-16-fluoro-14-O-[3-(4-methylpiperazin-1-ylcarbonyl)-propionyl]pristinamycin II$_B$, in the form of a white powder melting at 130° C.

$^1$H NMR spectrum (400 MHz, CDCl$_3$, δ in ppm): 0.96 (d, J=6.5 Hz: 3H); 1.00 (d, J=6.5 Hz: 3H); 1.10 (d, J=6.5 Hz: 3H); from 1.65 to 2.05 (mt: 5H); 1.88 (s: 3H); 2.15 (mt: 1H); from 2.20 to 2.45 (mt: 5H); 2.31 (s: 3H); from 2.50 to 2.75 (mt: 4H); 2.76 (mt: 1H); 3.00 (mt: 1H); 3.23 (mt: 1H); from 3.40 to 3.55 (mt: 1H); 3.50 (mt: 2H); 3.63 (mt: 2H); 3.87 (mt: 1H); 4.06 (mt: 1H); 4.53 (mt: 1H); 4.78 (broad d, J=10 Hz: 1H); 4.82 (dd, J=9 and 3 Hz: 1H); 5.14 (decoupled doublet, J$_{HF}$=48 Hz: 1H); 5.33 (d, J=9.5 Hz: 1H); from 5.75 to 5.90 (mt: 1H); 5.75 (mt: 1H); 5.81 (broad d, J=16 Hz: 1H); 5.96 (mt 1H); 6.20 (d, J=16 Hz: 1H); 6.51 (dd, J=16 and 5 Hz: 1H); 8.12 (s: 1H).

4-(4-Methylpiperazin-1-yl)-4-oxobutyric acid may be prepared in the following manner:

1.17 g of succinic anhydride and then 1.19 cm$^3$ of N-methylpiperazine are added to 20 cm$^3$ of dioxane. After stirring for 18 hours at room temperature, the precipitate obtained is filtered and then rinsed successively with a minimum of dioxane, with twice 10 cm$^3$ of acetone and with 10 cm$^3$ of diethyl ether. After drying under reduced pressure (2.7 kPa)

at 20° C., 1.09 g of 4-(4-methylpiperazin-1-yl)-4-oxobutyric acid are obtained in the form of a white solid melting at 114° C.

EXAMPLE 41

(16R)-16-Deoxo-16-fluoro-14-O-{3-[4-(pyridin-2-yl)piperazin-1-ylcarbonyl]-propionyl}pristinamycin II$_B$ The procedure is carried out as in Example 40, but starting with 240 mg of 4-oxo-4-[4-(pyridin-2-yl)piperazin-1-yl)]butyric acid, 400 mg of (16R)-16-deoxo-16-fluoropristinamycin II$_B$ (prepared as described in Example 1), 190 mg of N,N'-dicyclohexylcarbodiimide, 46 mg of 4-dimethylaminopyridine and then 6 cm³ of dichloromethane. After stirring for 66 hours and a treatment similar to that in Example 40, 655 mg of a solid are obtained, which solid is purified by flash chromatography [eluent: dichloromethane-methanol (95-5 by volume)]. A solid is isolated which is stirred for 20 minutes in 4 cm³ of diethyl ether. The white solid obtained is filtered, rinsed with diethyl ether and then dried at 50° C. (90 Pa) to give 308 mg of (16R)-16-deoxo-16-fluoro-14-O-{3-[4-(pyridin-2-yl)piperazin-1-yl-carbonyl]propionyl}pristinamycin II$_B$, in the form of a white powder melting at around 140° C. (dec.).

$^1$H NMR spectrum (400 MHz, CDCl$_3$, δ in ppm): 0.96 (d, J=6.5 Hz: 3H); 1.01 (d, J=6.5 Hz: 3H); 1.10 (d, J=6.5 Hz: 3H); from 1.65 to 2.05 (mt: 5H); 1.88 (s: 3H); 2.15 (mt: 1H); 2.30 (mt: 1H); from 2.55 to 2.80 (mt: 4H); 2.76 (mt: 1H); 3.00 (mt: 1H); 3.23 (mt: 1H); 3.46 (mt: 1H); 3.51 (mt: 2H); 3.63 (mt: 4H); 3.75 (mt: 2H); 3.87 (mt: 1H); 4.06 (mt: 1H); 4.53 (mt: 1H); 4.78 (dd, J=10 and 1.5 Hz: 1H); 4.82 (dd, J=9 and 3 Hz: 1H); 5.14 (decoupled doublet, J$_{HF}$=48 Hz: 1H); 5.34 (d, J=9.5 Hz: 1H); from 5.75 to 5.90 (mt: 1H); 5.75 (mt: 1H); 5.81 (dd, J=16 and 1.5 Hz: 1H); 5.96 (mt: 1H); 6.20 (d, J=16 Hz: 1H); 6.51 (dd, J=16 and 5 Hz: 1H); from 6.60 to 6.70 (mt: 2H); 7.52 (mt: 1H); 8.12 (s: 1H); 8.21 (dd, J=5 and 1.5 Hz: 1H).

4-Oxo-4-[4-(pyridin-2-yl)piperazin-1-yl)]butyric acid may be prepared in the following manner:

0.97 g of succinic anhydride and then 1.5 cm³ of 1-(2-pyridyl)piperazine are added to 15 cm³ of dioxane. After stirring for 4.5 hours at 20° C., the solvent is evaporated under reduced pressure (2.7 kPa) at 20° C. to give a solid which is recrystallized hot from 33 cm³ of acetone. After filtration, the solid is rinsed successively with a minimum of acetone and with diethyl ether, and then dried under reduced pressure (2.7 kPa) at 20° C., to give 986 mg of 4-oxo-4-[4-(pyridin-2-yl)piperazin-1-yl)]butyric acid in the form of a white solid melting at 134° C.

EXAMPLE 42

(16R)-16-Deoxo-16-fluoro-14-O-{3-[4-(pyrrolidin-1-yl-carbonylmethyl)piperazin-1-ylcarbonyl]propionyl}pristinamycin II$_B$ Carrying out the procedure as in Example 40, but starting with 750 mg of 4-oxo-4-[4-(2-oxo-2-pyrrolidin-1-ylethyl)piperazin-1-yl)]butyric acid, 1 g of (16R)-16-deoxo-16-fluoropristinamycin II$_B$ (prepared as described in Example 1), 190 mg of N,N'-dicyclohexylcarbodiimide, 60 mg of 4-dimethylaminopyridine and then 20 cm³ of dichloromethane. After stirring for 25 hours, an additional 95 mg of N,N'-dicyclohexylcarbodiimide and 95 mg of 4-dimethylaminopyridine are added and then the stirring is continued for 19 hours. After treatment, 1.54 g of a solid are obtained, which solid is purified by flash chromatography [eluent: dichloromethane-methanol (95/5 by volume)]. The fractions are concentrated to give 530 mg of a solid which is taken up in 5 cm³ of diethyl ether. The white solid obtained is filtered, rinsed with diethyl ether and then dried at 50° C. (90 Pa) to give 480 mg of (16R)-16-deoxo-16-fluoro-14-O-{3-[4-(pyrrolidin-1-ylcarbonylmethyl)piperazin-1-ylcarbonyl]-propionyl}pristinamycin II$_B$, in the form of a white powder melting at 132° C. (dec.).

$^1$H NMR spectrum (400 MHz, CDCl$_3$, δ in ppm): 0.95 (d, J=6.5 Hz: 3H); 1.00 (d, J=6.5 Hz: 3H); 1.09 (d, J=6.5 Hz: 3H); from 1.65 to 2.05 (mt: 9H); 1.88 (s: 3H); 2.14 (mt: 1H); 2.28 (mt: 1H); from 2.45 to 2.75 (mt: 8H); 2.76 (mt: 1H); 3.00 (td, J=17 and 6 Hz: 1H); 3.14 (s: 2H); 3.25 (mt: 1H); from 3.40 to 3.55 (mt: 7H); 3.66 (mt: 2H); 3.87 (mt: 1H); 4.05 (mt: 1H); 4.52 (mt: 1H); 4.78 (dd, J=10 and 1.5 Hz: 1H); 4.81 (dd, J=9 and 3 Hz: 1H); 5.12 (decoupled doublet, J$_{HF}$=48 Hz: 1H); 5.33 (d, J=9.5 Hz: 1H); 5.74 (mt: 1H); from 5.75 to 5.85 (mt: 1H); 5.81 (dd, J=17 and 1.5 Hz: 1H); 6.00 (mt: 1H); 6.19 (d, J=16 Hz: 1H); 6.51 (dd, J=17 and 5 Hz: 1H); 8.12 (s: 1H).

4-Oxo-4-[4-(2-oxo-2-pyrrolidin-1-ylethyl)piperazin-1-yl] butyric acid may be prepared in the following manner:

0.72 g of succinic anhydride and then 1.5 cm³ of 95% 1-(pyrrolidinocarbonylmethyl)-piperazine are added to 20 cm³ of dioxane in a round-bottomed flask kept under a nitrogen atmosphere. After stirring for 4.75 hours at room temperature, the solvent is evaporated under reduced pressure (2.7 kPa) at 20° C., to give 2.4 g of 4-oxo-4-[4-(2-oxo-2-pyrrolidin-1-ylethyl)piperazin-1-yl]butyric acid in the form of a pale yellow paste which is used as it is.

EXAMPLE 43

(16R)-16-Deoxo-14-O-[3-(2-dimethylaminoethylcarbamoyl)propionyl]-16-fluoro-pristinamycin II$_B$ Carrying out the procedure as in Example 40 but starting with 170 mg of N-(2-dimethylaminoethyl)succinamic acid, 400 mg of (16R)-16-deoxo-16-fluoro-pristinamycin II$_B$ (prepared as described in Example 1), 190 mg of N,N'-dicyclohexylcarbodiimide, 46 mg of 4-dimethylaminopyridine and then 6 cm³ of dichloromethane, 580 mg of a solid are obtained, after stirring for 18 heures and a treatment similar to that in Example 40, which solid is taken up in 15 cm³ of dichloromethane and 100 cm³ of distilled water. 0.1 M hydrochloric acid is added so as to adjust the pH to 4. The aqueous phase is extracted with twice 5 cm³ of dichloromethane and then adjusted to pH7 by addition of a sodium bicarbonate solution. After decantation, the aqueous phase is extracted with three times 10 cm³ of dichloromethane. The organic phases are combined, dried over sodium sulfate, filtered and concentrated to dryness under reduced pressure (2.7 kPa) at 20° C., to give a solid which is stirred in 5 cm³ of diethyl ether, filtered and then dried at 50° C. (90 Pa). 112 mg of (16R)-16-deoxo-14-O-[3-(2-dimethylaminoethylcarbamoyl)]-propionyl-16-fluoropristinamycin II$_B$ are obtained in the form of a white powder melting at 114° C. (dec.).

$^1$H NMR spectrum (400 MHz, CDCl$_3$, δ in ppm): 0.97 (d, J=6.5 Hz: 3H); 1.00 (d, J=6.5 Hz: 3H); 1.10 (d, J=6.5 Hz: 3H); from 1.65 to 2.05 (mt: 5H); 1.88 (s: 3H); from 2.10 to 2.35 (mt: 2H); 2.24 (s: 6H); from 2.35 to 2.75 (mt: 4H); 2.41 (t, J=6 Hz: 2H); 2.77 (mt: 1H); 3.00 (td, J=17 and 6 Hz: 1H); 3.23 (mt: 1H); 3.33 (q, J=6 Hz: 2H); 3.47 (mt: 1H); 3.87 (mt: 1H); 4.07 (mt: 1H); 4.54 (mt: 1H); 4.78 (broad d, J=10 Hz: 1H); 4.82 (dd, J=9 and 3 Hz: 1H); 5.13 (decoupled doublet, $J_{HF}$=48 Hz: 1H); 5.32 (d, J=9.5 Hz: 1H); from 5.75 to 5.90 (mt: 1H); 5.75 (mt: 1H); 5.82 (broad d, J=17 Hz: 1H); 5.98 (mt: 1H); from 6.10 to 6.25 (mt: 1H); 6.20 (d, J=16 Hz: 1H); 6.51 (dd, J=17 and 5 Hz: 1H); 8.13 (s: 1H).

N-(2-Dimethylaminoethyl)succinamic acid may be prepared in the following manner:

1.4 g of succinic anhydride and then 1.5 cm³ of 2-dimethylaminoethylamine are added to 15 cm³ of dioxane. After stirring for 18 hours at room temperature, the solvent is evaporated under reduced pressure (2.7 kPa) at 20° C., to give a residue which is taken up hot in 40 cm³ of methyl ethyl ketone. After cooling, the solubilized fraction is removed. The residual gum is crystallized hot from 15 cm³ of acetone. After filtration, the solid is rinsed with a minimum of acetone and then with diethyl ether, and dried under reduced pressure (2.7 kPa) at 20° C. to give 2.03 g of N-(2-dimethylaminoethyl)succinamic acid in the form of a white solid melting at 155° C.

EXAMPLE 44

(16R)-14-O-(3-Carboxypropionyl)-16-deoxo-16-fluoropristinamycin II$_B$

Carrying out the procedure as in Example 39, but starting with 5 g of (16R)-16-deoxo-16-fluoropristinamycin II$_B$ (prepared as described in Example 1), 2.82 g of succinic anhydride, 1.15 g of 4-dimethylaminopyridine and 25 cm³ of pyridine, and after stirring for 4 hours 50 minutes, an orange-yellow oil is obtained which is stirred for 18 hours in diethyl ether to give an off-white powder. The solid is filtered and then stirred in diethyl ether, filtered and dried at 30° C. (90 Pa), to give 4.96 g of solid. One gram of this solid is stirred for one hour in 10 cm³ of dichloromethane, filtered and then rinsed with diethyl ether. The solid obtained is washed three times with distilled water and then with diethyl ether to give 820 mg of (16R)-14-O-[3-carboxypropionyl)-16-deoxo-16-fluoropristinamycin II$_B$, in the form of a white solid melting at around 192° C.

¹H NMR spectrum (400 MHz, CDCl₃, δ in ppm): 0.97 (d, J=6.5 Hz: 3H); 1.01 (d, J=6.5 Hz: 3H); 1.10 (d, J=6.5 Hz: 3H); from 1.55 to 2.05 (mt: 5H); 1.89 (s: 3H); 2.16 (mt: 1H); 2.27 (mt: 1H); from 2.55 to 2.70 (mt: 4H); 2.77 (mt: 1H); 3.00 (td, J=17 and 6 Hz: 1H); 3.25 (mt: 1H); 3.50 (mt: 1H); 3.87 (mt: 1H); 4.07 (mt: 1H); 4.52 (mt: 1H); 4.79 (dd, J=10 and 1.5 Hz: 1H); 4.83 (dd, J=9 and 3 Hz: 1H); 5.12 (decoupled doublet, $J_{HF}$=48 Hz: 1H); 5.33 (d, J=9.5 Hz: 1H); from 5.75 to 5.90 (mt: 1H); 5.77 (mt: 1H); 5.83 (broad d, J=17 Hz: 1H); 5.96 (mt: 1H); 6.20 (d, J=16 Hz: 1H); 6.53 (dd, J=17 and 5 Hz: 1H); 8.13 (s: 1H).

EXAMPLE 45

(16R)-16-Deoxo-16-fluoro-14-O-[4-(2-morpholinoethylcarbamoyl)butyryl)-pristinamycin II$_B$ hydrochloride 0.2 cm³ of 3 M hydrochloric ether is added, at 4° C., to 280 mg of (16R)-16-deoxo-16-fluoro-14-O-[4-(2-morpholinoethylcarbamoyl)butyryl]pristinamycin II$_B$ in solution in 3 cm³ of methyl isobutyl ketone. The precipitate formed is filtered on No. 4 sintered glass, rinsed several times with methyl isobutyl ketone and then with diethyl ether. The white powder obtained is dried at 20° C. (90 Pa) to give 268 mg of (16R)-16-deoxo-16-fluoro-14-O-[4-(2-morpholinoethylcarbamoyl)butyryl]-pristinamycin II$_B$ hydrochloride in the form of a white solid melting at 134° C.

(16R)-16-Deoxo-16-fluoro-14-O-[4-(2-morpholinoethylcarbamoyl)butyryl]-pristinamycin II$_B$ may be prepared in the following manner:

459 mg of (16R)-16-deoxo-16-fluoropristinamycin II$_B$ (prepared as described in Example 1), 388 mg of N,N'-dicyclohexylcarbodiimide and then 23 mg of 4-dimethylaminopyridine are added to 1 g of 5-(2-morpholinoethylamino)-5-oxopentanoic acid in solution in 40 cm³ of dichloromethane. The reaction is stirred at 20° C. for 48 hours. The dicyclohexylurea formed is then filtered on No. 4 sintered glass and then rinsed with ethyl acetate. The filtrate is concentrated to dryness under reduced pressure (2.7 kPa), to give 1.35 g of a solid which is purified by flash chromatography [eluent: dichloromethane-methanol (95-5 by volume)]. 490 mg of a product are thus obtained, which product is again purified by flash chromatography on alumina [eluent: ethyl acetate-methanol (98-2 by volume)]. The fractions are concentrated under reduced pressure (2.7 kPa) to give a solid which is taken up in diethyl ether and stirred for 18 hours. The white solid obtained is filtered, rinsed with twice diethyl ether and then dried at 20° C. (90 Pa) to give 294 mg of (16R)-14-O-[4-(2-morpholinoethylcarbamoyl)butyryl]-16-fluoropristinamycin II$_B$ in the form of a white powder.

¹H NMR spectrum (400 MHz, CDCl₃, δ in ppm): 0.96 (d, J=6.5 Hz: 3H); 1.00 (d, J=6.5 Hz: 3H); 1.10 (d, J=6.5 Hz: 3H); from 1.65 to 2.05 (mt: 5H); 1.90 (s: 3H); 1.95 (mt: 2H); from 2.10 to 2.30 (mt: 2H); 2.25 (t, J=7 Hz: 2H); 2.37 (mt: 2H); 2.47 (mt: 6H); 2.76 (mt: 1H); 2.99 (dt, J=17 and 6 Hz: 1H); 3.24 (mt: 1H); 3.36 (dt, J=7 and 6 Hz: 1H); 3.48 (mt: 1H); 3.71 (t, J=5 Hz: 4H); 3.85 (mt: 1H); 4.07 (mt: 1H); 4.54 (mt: 1H); 4.79 (broad d, J=10 Hz: 1H); 4.82 (dd, J=9 and 3 Hz: 1H); 5.12 (decoupled doublet, $J_{HF}$=48 Hz: 1H); 5.30 (d, J=9 Hz: 1H); from 5.70 to 5.85 (mt: 2H); 5.82 (broad d, J=17 Hz: 1H); 6.00 (mt: 2H); 6.19 (d, J=16 Hz: 1H); 6.52 (dd, J=17 and 5 Hz: 1H); 8.12 (s: 1H).

5-(2-Morpholinoethylamino)-5-oxopentanoic acid may be prepared in the following manner:

There are added to 10 cm³ of dioxane, 1.517 g of glutaric anhydride and then, dropwise, 1.75 cm³ of N-(2-aminoethyl) morpholine. Stirring is continued at 20° C. for 0.75 hours. The white solid formed is filtered, washed successively with dioxane and diethyl ether, and then dried at 20° C. (90 Pa) to give 1.94 g of 5-(2-morpholinoethylamino)-5-oxopentanoic acid in the form of a white solid melting at 96° C.

EXAMPLE 46

(16R)-16-Deoxo-16-fluoro-14-O-{(3RS)-3-methyl-4-[4-(pyrrolidin-1-yl-carbonyl-methyl)piperazin-1-ylcarbonyl]butyryl}pristinamycin II$_B$ hydrochloride 1 g of (16R)-16-deoxo-16-fluoropristinamycin II$_B$ (prepared as described in Example 1) and 40 cm³ of dichloromethane are introduced into a round-bottomed flask placed under nitrogen. The mixture is heated until dissolution is obtained and then 620 mg of 3-methyl-5-oxo-5-[4-(2-oxo-2-pyrrolidin-1-ylethyl)piperazin-1-yl]pentanoic acid, 389 mg of N,N'-dicyclohexylcarbodiimide and then 45 mg of 4-dimethylamino-pyridine are added at 20° C. After stirring for 24 hours at 20° C., an additional 124 mg of 3-methyl-5-oxo-5-[4-(2-oxo-2-pyrrolidin-1-ylethyl)piperazin-1-yl]pentanoic acid, 78 mg of N,N'-dicyclohexylcarbodiimide and 9 mg of 4-dimethylaminopyridine are added. The reaction is stirred at 20° C. for 24 hours and then the reaction mixture is filtered, rinsed with ethyl acetate and concentrated to dryness under reduced pressire (2.7 kPa).

The residue is stirred for 1 hour in a mixture of 30 cm³ of ethyl acetate and 6 cm³ of dichloromethane and then filtered. The insoluble matter is filtered and rinsed with ethyl acetate. The filtrates are combined and washed successively with twice 5 cm³ of a 5% aqueous sodium bicarbonate solution and with 10 cm³ of water saturated with sodium chloride. The resulting organic phase is dried over magnesium sulfate, filtered and then concentrated to dryness under reduced pressure (2.7 kPa). The yellow solid obtained is stirred in 40 cm³ of diethyl ether for 18 hours, filtered and then purified by flash chromatography [eluent: dichloromethane-methanol (95-5 by volume)]. A product is thus obtained which is stirred in diethyl ether, filtered and then dried at 30° C. (90 Pa), to give 610 mg of (16R)-16-deoxo-16-fluoro-14-O-{(3RS)-3-methyl-4-[4-(pyrrolidin-1-yl-carbonylmethyl)piperazin-1-ylcarbonyl]butyryl}-pristinamycin II$_B$, in the form of a white powder.

0.25 cm³ of 3 M hydrochloric ether and then 10 cm³ of diethyl ether are added to this solid dissolved in 3 cm³ of absolute ethanol. The solvents are evaporated under reduced pressure and the resulting solid is concreted in 20 cm³ of diethyl ether. After filtration and drying at 25° C. (90 Pa), 610 mg of (16R)-16-deoxo-16-fluoro-14-O-{(3RS)-3-methyl-[4-(pyrrolidin-1-ylcarbonylmethyl)piperazin-1-ylcarbonyl]-butyryl}pristinamycin II$_B$ hydrochloride are obtained in the form of a white solid melting at 180° C.

$^1$H NMR spectrum (400 MHz, (CD$_3$)$_2$SO d6, δ in ppm): 0.88 (d, J=6.5 Hz: 3H); from 0.90 to 1.00 (mt: 6H); 1.06 (d, J=6.5 Hz: 3H); 1.58 (mt: 1H); from 1.70 to 2.50 (mt: 15H); 1.80 (s: 3H); 2.78 (mt: 1H); from 3.00 to 3.50 (mt: 10H); 3.40 (mt: 4H); 3.65 (mt: 1H); 3.72 (mt: 1H); 3.81 (mt: 1H); 3.95 (mt: 1H); 4.15 (unresolved complex: 2H); from 4.70 to 4.80 (mt: 2H); 5.10 (decoupled doublet, J$_{HF}$=48 Hz: 1H); 5.43 (d, J=9 Hz: 1H); 5.66 (mt: 1H); 5.76 (mt: 1H); 5.83 (dd, J=16 and 1.5 Hz: 1H); 6.20 (d, J=16 Hz: 1H); 6.63 (dd, J=16 and 4 Hz: 1H); 8.04 (t, J=6 Hz: 1H); 8.48 (s: 1H); from 9.85 to 10.50 (very broad unresolved complex: 1H).

(3RS)-3-Methyl-5-oxo-5-[4-(2-oxo-2-pyrrolidin-1-yl-ethyl)piperazin-1-yl]pentanoic acid may be obtained in the following manner:

1.6 g of 3-methylglutaric anhydride and then 2.62 g of pyrrolidinocarbonylmethyl-piperazine are added to 10 cm³ of dioxane. After stirring for 8 hours, an additional 320 mg of 3-methylglutaric anhydride are added and then the stirring is continued at 20° C. for 18 hours. The solvent is then evaporated under reduced pressure and then the resulting oil is dried at 45° C. (90 Pa) to give 4.5 g of (3RS)-3-methyl-5-oxo-5-[4-(2-oxo-2-pyrrolidin-1-ylethyl)piperazin-1-yl]pentanoic acid in the form of an orange-colored oil which is used as it is.

EXAMPLE 47

(16R)-16-Deoxo-16-fluoro-14-O-[4-(4-methylpiperazin-1-ylcarbonyl)butyryl]-pristinamycin II$_B$ hydrochloride Carrying out the procedure as in Example 45, but starting with 580 mg of 5-(4-methylpiperazin-1-yl)-5-oxopentanoic acid, 1.21 g of (16R)-16-deoxo-16-fluoropristinamycin II$_B$ (prepared as described in Example 1), 700 mg of N,N'-dicyclohexylcarbodiimide, 170 mg of 4-dimethylaminopyridine in 25 cm³ of dichloromethane, a solid is obtained which is purified by flash chromatography [eluent: dichloromethanelmethanol (95/5 by volume)]. After concentrating the fractions to dryness under reduced pressure (2.7 kPa) at 20° C., 1.45 g of (16R)-16-deoxo-16-fluoro-14-O-[4-(4-methylpiperazin-1-ylcarbonyl)butyryl]-pristinamycin II$_B$ are thus obtained. 3N hydrochloric ether is added to this solid dissolved in 8 cm³ of methyl isobutyl ketone until complete precipitation is obtained. The solid obtained is filtered, rinsed successively with three times 2 cm³ of methyl isobutyl ketone and with three times 10 cm³ of diethyl ether, and then dried (90 Pa) at 50° C., to give 1.24 g of (16R)-16-deoxo-16-fluoro-14-O-[4-(4-methylpiperazin-1-ylcarbonyl)butyryl]pristinamycin II$_B$ hydrochloride in the form of a white solid melting at around 165° C. (dec.).

$^1$H NMR spectrum (400 MHz, (CD$_3$)$_2$SO d6, δ in ppm): 0.86 (mt: 3H); 0.94 (d, J=6.5 Hz: 3H); 1.04 (d, J=6.5 Hz: 3H); 1.52 (mt: 1H); from 1.65 to 2.15 (mt: 7H); 1.77 (s: 3H); 2.20 (mt: 1H); from 2.25 to 2.45 (mt: 4H); from 2.70 to 2.80 (mt: 1H); 2.76 (s: 3H); from 2.80 to 3.10 (mt: 3H); from 3.10 to 3.50 (mt: 5H); 3.60 (broad d, J=14 Hz: 1H); 3.68 (mt: 1H); 3.81 (mt: 1H); from 3.90 to 4.10 (mt: 2H); 4.43 (unresolved complex: 1H); from 4.70 to 4.80 (mt: 2H); 5.10 (decoupled doublet, J$_{HF}$=48 Hz: 1H); 5.43 (d, J=9 Hz: 1H); 5.61 (mt: 1H); 5.74 (mt: 1H); 5.80 (broad d, J=16 Hz: 1H); 6.19 (d, J=16 Hz: 1H); 6.62 (dd, J=16 and 4 Hz: 1H); 8.17 (mt: 1H); 8.52 (s: 1H); 10.91 (unresolved complex: 1H).

5-(4-Methylpiperazin-1-yl)-5-oxopentanoic acid may be prepared in the following manner:

1.6 g of 3-methylglutaric anhydride and then 2.62 g of piperazin-1-ylcarboxymethylpyrrolidine are added to 20 cm³ dioxane. After stirring for 8 hours, an additional 320 mg of 3-methylglutaric anhydride are added and then the stirring is continued at 20° C. for 18 hours. The solvent is evaporated under reduced pressure and then the resulting oil is dried at 45° C. (90 Pa) to give 4.5 g of 5-(4-methylpiperazin-1-yl)-5-oxopentanoic acid in the form of an orange-colored oil which is used as it is.

EXAMPLE 48

(16R)-16-Deoxo-16-fluoro-14-O-[4-(4-ethylpiperazin-1-ylcarbonyl)butyryl]-pristinamycin II$_B$ hydrochloride 0.35 cm³ of 3 M hydrochloric ether is added, at 20° C., to 390 mg of (16R)-16-deoxo-16-fluoro-14-O-[4-(4-ethylpiperazin-1-ylcarbonyl)butyryl]pristinamycin II$_B$ in solution in 5 cm³ of methyl isobutyl ketone. The precipitate formed is filtered, rinsed successively with a minimum of methyl isobutyl ketone and with diethyl ether, and then dried at 20° C. (90 Pa) to give 340 mg of (16R)-16-deoxo-16-fluoro-14-O-[4-(4-ethylpiperazin-1-ylcarbonyl)butyryl]pristinamycin II$_B$ hydrochloride in the form of a white solid melting at around 150° C. (dec.).

$^1$H NMR spectrum (400 MHz, (CD$_3$)$_2$SO d6, δ in ppm): 0.87 (mt: 3H); 0.95 (d, J=6.5 Hz: 3H); 1.05 (d, J=6.5 Hz: 3H); 1.25 (broad t, J=7 Hz: 3H); 1.53 (mt: 1H); from 1.65 to 2.15 (mt: 7H); 1.79 (s: 3H); 2.20 (mt: 1H); from 2.30 to 2.45 (mt: 4H); 2.77 (mt: 1H); from 2.80 to 3.55 (mt: 10H); 3.61 (broad d, J=15 Hz: 1H); 3.69 (mt: 1H); 3.82 (mt: 1H); 3.96 (mt: 1H); 4.04 (broad d, J=13.5 Hz: 1H); 4.48 (broad d, J=13.5 Hz: 1H); from 4.70 to 4.80 (mt: 2H); 5.10 (decoupled doublet, J$_{HF}$=48 Hz: 1H); 5.43 (d, J=9 Hz: 1H); 5.62 (mt: 1H); 5.75 (mt: 1H); 5.81 (dd, J=16 and 1.5 Hz: 1H); 6.19 (d, J=16 Hz: 1H); 6.63 (dd, J=16 and 4 Hz: 1H); 8.15 (mt: 1H); 8.51 (s: 1H); 10.16 (broad unresolved complex: 1H).

(16R)-16-Deoxo-16-fluoro-14-O-[4-(4-ethylpiperazin-1-ylcarbonyl)butyryl]-pristinamycin II$_B$ may be prepared in the following manner:

Carrying out the procedure as in Example 45, but starting with 430 mg of 5-(4-ethylpiperazin-1-yl)-5-oxopentanoic acid, 1 g of (16R)-16-deoxo-16-fluoro-pristinamycin II$_B$ (prepared as described in Example 1), 390 mg of N,N'-dicyclohexylcarbodiimide, 23 mg of 4-dimethylaminopyridine in 40 cm³ of dichloromethane, and after addition of 50 mg of magnesium sulfate, an additional 43 mg of 5-(4-ethylpiperazin-1-yl)-5-oxopentanoic acid, 39 mg of N,N'-dicyclohexyl-carbodiimide and 2.3 mg of 4-dimethylaminopyridine are added after stirring for 27 hours. After reacting for an additional 4 hours and treatment, 1.16 g of a solid is obtained, which solid is purified by flash chromatography [eluent: dichloromethane-methanol (95/5 by volume)]. After concentrating the fractions to dryness under reduced pressure (2.7 kPa), at 20° C., 260 mg of pure product and 420 mg of a solid are obtained, which solid is repurified by two semipreparative HPLC chromatographies [5 μM Hypersil silica, eluent: dichloromethane/methanol (95/5 by volume) and then a dichloromethane/methanol gradient (97/3 and then 95/5 by volume)]. Both batches thus obtained are combined to give 390 mg of (16R)-16-deoxo-16-fluoro-14-O-[4-(4-ethylpiperazin-1-ylcarbonyl)butyryl]pristinamycin II$_B$, in the form of a white solid.

5-(4-Ethylpiperazin-1-yl)-5-oxopentanoic acid may be prepared in the following manner:

1.5 g of 1-ethylpiperazine and 1.5 g of glutaric anhydride in solution in 5 cm³ of dioxane are added, under argon, to 10 cm³ of dioxane. The stirring is continued at 25° C. for 19 hours. The solvents are evaporated under reduced pressure (2.7 kPa) to give a brown oil which is stirred in ethyl ether. The solid obtained is filtered, rinsed with diethyl ether and then dried at 20° C. (90 Pa) to give 1.95 g of 5-(4-ethylpiperazin-1-yl)-5-oxopentanoic acid in the form of a hygroscopic pink solid which is used as it is.

EXAMPLE 49

(16R)-16-Deoxo-14-O-[4-(4-ethoxycarbonylmethylpiperazin-1-ylcarbonyl)butyryl]-16-fluoropristinamycin II$_B$ 1 g of (16R)-16-deoxo-16-fluoropristinamycin II$_B$ (prepared as described in Example 1) and 30 cm³ of dichloromethane are introduced into a round-bottomed flask placed under nitrogen. The mixture is heated until dissolution is obtained and then cooled. 540 mg of 5-[4-(ethoxycarbonylmethylpiperazin-1-yl)]-5-oxopentanoic acid in solution in 10 cm³ of dichloromethane, 23 mg of 4-dimethylaminopyridine and then 390 mg of N,N'-dicyclohexylcarbodiimide are added at 20° C. After stirring for 18 hours at 20° C., an additional 54 mg of 5-[4-(ethoxycarbonylmethylpiperazin-1-yl)]-5-oxopentanoic acid, 39 mg of N,N'-dicyclohexylcarbodiimide and 2.3 mg of 4-dimethylaminopyridine are added. The reaction is stirred at 20° C. for 2 days, and then the reaction mixture is filtered, rinsed with dichloromethane and concentrated to dryness under reduced pressure (2.7 kPa). The resulting solid is stirred for 20 hours in 40 cm³ of diethyl ether, filtered, dried at 20° C. (90 Pa) and then purified by flash chromatography [eluent: dichloromethane-methanol (98–2 by volume)]. A product is thus obtained which is stirred in diethyl ether, filtered and then dried at 20° C. (90 Pa) to give 640 mg of (16R)-16-deoxo-14-O-[4-(4-ethoxycarbonylmethylpiperazin-1-ylcarbonyl)butyryl]-16-fluoropristinamycin II$_B$ in the form of a white powder.

0.35 cm³ of 3 M hydrochloric ether is added to this solid dissolved in 7 cm³ of methyl ethyl ketone. The precipitate obtained is filtered on No. 3 sintered glass, rinsed with three times 10 cm³ of methyl ether ketone and then with three times 15 cm³ of diethyl ether. After drying at 20° C. (90 Pa), 450 mg of (16R)-16-deoxo-14-O-[4-(4-ethoxy-carbonylmethylpiperazin-1-ylcarbonyl)butyryl]-16-fluoropristinamycin II$_B$ hydrochloride are obtained in the form of a white solid melting at 156° C.

¹H NMR spectrum (400 MHz, (CD$_3$)$_2$SO d6, δ in ppm): 0.88 (d, J=6.5 Hz: 3H); 0.96 (d, J=6.5 Hz: 3H); 1.06 (d, J=6.5 Hz: 3H); 1.27 (t, J=7 Hz: 3H); 1.57 (mt: 1H); from 1.70 to 2.35 (mt: 8H); 1.79 (s: 3H); 2.37 (mt: 4H); 2.78 (mt: 1H); from 2.90 to 3.50 (mt: 12H); 3.65 (mt: 1H); 3.72 (mt: 1H); 3.81 (mt: 1H); 3.95 (mt: 1H); 4.23 (q, J=7 Hz: 2H); from 4.70 to 4.80 (mt: 2H); 5.10 (decoupled doublet, J$_{HF}$=48 Hz: 1H); 5.42 (d, J=9 Hz: 1H); 5.66 (mt: 1H); 5.76 (mt: 1H); 5.82 (dd, J=16 and 1.5 Hz: 1H); 6.19 (d, J=16 Hz: 1H); 6.63 (dd, J=16 and 4 Hz: 1H); 8.03 (t, J=6 Hz: 1H); 8.48 (s: 1H).

5-[4-(Ethoxycarbonylmethylpiperazin-1-yl)]-5-oxopentanoic acid may be obtained in the following manner:

1.5 g of glutaric anhydride and then 2.26 g of N-ethoxycarbonylmethylpiperazine in solution in 5 cm³ of dioxane are added to 10 cm³ of dioxane in a round-bottomed flask kept under an argon atmosphere. After stirring for 2 hours at room temperature, the solvent is evaporated under reduced pressure to give 3.66 g of 5-[4-(ethoxycarbonyl-methylpiperazin-1-yl)]-5-oxopentanoic acid in the form of an orange-colored oil which is used as it is.

EXAMPLE 50

(16R)-16-Deoxo-16-fluoro-14-O-{4-[4-(pyrrolidin-1-ylcarbonylmethyl)piperazin-1-ylcarbonyl]butyryl}pristinamycin II$_B$ Carrying out the procedure as in Example 46, but starting with 1.75 g of 5-oxo-5-[4-(2-oxo-2-pyrrolidin-1-yl]pentanoic acid, 2.5 g of (16R)-16-deoxo-16-fluoropristinamycin II$_B$ (prepared as described in Example 1), 1.16 g of N,N'-dicyclohexylcarbodiimide and 113 mg of 4-dimethylaminopyridine in 100 cm³ of dichloromethane, a solid is obtained after stirring for 4 hours at 20° C. and after a treatment similar to that in Example 46, which solid is purified by flash chromatography [eluent: dichloromethane-methanol (95–5 by volume)]. After concentrating the fractions to dryness under reduced pressure (2.7 kPa) at 20° C., and then stirring the solid obtained in diethyl ether for 18 hours, filtration and drying (90 Pa) at 20° C., 2.46g of (16R)-16-deoxo-16-fluoro-14-O-{4-[4-(pyrrolidin-1-yl-carbonylmethyl)piperazin-1-ylcarbonyl]butyryl}pristinamycin II$_B$, in the form of a pale yellow powder melting at 135° C.

¹H NMR spectrum (500 MHz, CDCl$_3$, δ in ppm): 0.96 (d, J=6.5 Hz: 3H); 1.00 (d, J=6.5 Hz: 3H); 1.10 (d, J=6.5 Hz: 3H); from 1.65 to 2.05 (mt: 11H); 1.89 (s: 3H); from 2.10 to 2.30 (mt: 2H); 2.37 (mt: 4H); 2.54 (t, J=5 Hz: 2H); 2.57 (t, J=5 Hz: 2H); 2.76 (mt: 1H); 2.99 (dt, J=17 and 6 Hz: 1H); 3.14 (s: 2H); 3.23 (mt: 1H); 3.48 (mt: 7H); 3.66 (t, J=5 Hz: 2H); 3.86 (mt: 1H); 4.06 (mt: 1H); 4.53 (mt: 1H); 4.79 (dd, J=10 and 2 Hz: 1H); 4.82 (dd, J=9 and 3 Hz: 1H); 5.10 (decoupled doublet, J$_{HF}$=48 Hz: 1H); 5.30 (d, J=9 Hz: 1H); from 5.70 to 5.85 (mt: 3H); 6.06 (mt: 1H); 6.18 (d, J=16 Hz: 1H); 6.52 (dd, J=16.5 and 5 Hz: 1H); 8.12 (s: 1H).

5-Oxo-5-[4-(2-oxo-2-pyrrolidin-1-ylethyl)piperazin-1-yl]pentanoic acid may be prepared in the following manner:

1.52 g of glutaric anhydride and then 2.62 g of pyrrolidinocarbonylmethylpiperazine are added to 10 cm$^3$ of dry didoxane. After stirring for 4 hours, the precipitate formed is diluted with 10 cm$^3$ of dioxane and then stirred for 1 hour. The insoluble matter is filtered on No. 4 sintered glass, rinsed several times with diethyl ether and then dried (90 Pa) at 20° C. to give 3.36 g of 5-oxo-5-[4-(2-oxo-2-pyrrolidin-1-yl ethyl)piperazin-1-yl]pentanoic acid in the form of a white solid.

EXAMPLE 51

(16R)-16-Deoxo-16-fluoro-14-O-[4-(cis-3,5-dimethylpiperazin-1-ylcarbonyl)butyryl]-pristinamycin II$_B$ hydrochloride 0.58 cm$^3$ of 3 M hydrochloric ether are added, at 20° C., to 680 mg of (16R)-16-deoxo-16-fluoro-14-O-[4-(cis-3,5-dimethylpiperazin-1-ylcarbonyl)butyryl]pristinamycin II$_B$ in solution in 12 cm$^3$ of methyl isobutyl ketone and the quantity of ethanol which is sufficient to dissolve the product while hot. The mixture is concentrated to dryness under reduced pressure (2.7 kPa) at 20° C. and the solid obtained is stirred for 1.5 hours in 10 cm$^3$ of diethyl ether. The solid is filtered on No. 4 sintered glass and then dried at 20° C. (90 Pa) to give 650 mg of (16R)-16-deoxo-16-fluoro-14-O-[4-(cis-3,5-dimethylpiperazin-1-ylcarbonyl)butyryl]pristinamycin II$_B$ hydrochloride in the form of a white solid melting at 205° C.

$^1$H NMR spectrum (600 MHz, (CD$_3$)$_2$SO d6, δ in ppm): 0.87 (mt: 3H); 0.95 (d, J=6.5 Hz: 3H); 1.05 (d, J=6.5 Hz: 3H); 1.27 (d, J=6.5 Hz: 6H); 1.53 (mt: 1H); from 1.65 to 1.85 (mt: 3H); 1.78 (s: 3H); from 1.85 to 2.00 (mt: 3H); 2.11 (mt: 1H); 2.21 (mt: 1H); from 2.25 to 2.50 (mt: 5H); 2.61 (mt: 1H); 2.78 (mt: 1H); from 3.05 to 3.30 (mt: 4H); 3.61 (broad d, J=15 Hz: 1H); 3.69 (mt: 1H); 3.82 (mt: 1H); from 3.90 to 4.05 (mt: 2H); 4.50 (broad d, J=13.5 Hz: 1H); from 4.70 to 4.80 (mt: 2H); 5.11 (decoupled doublet, J$_{HF}$=48 Hz: 1H); 5.44 (d, J=9 Hz: 1H); 5.62 (mt: 1H); 5.75 (mt: 1H); 5.81 (broad d, J=15.5 Hz: 1H); 6.20 (d, J=15 Hz: 1H); 6.63 (dd, J=15.5 and 4 Hz: 1H); 8.17 (t, J=6 Hz: 1H); 8.52 (s: 1H); 9.14 (mt: 1H); 9.56 (mt: 1H).

(16R)-16-Deoxo-16-fluoro-14-O-[4-(3,5-dimethylpiperazin-1-ylcarbamoyl)butyryl]-pristinamycin II$_B$ may be prepared in the following manner:

Carrying out the procedure as in Example 45, but starting with 470 mg of 5-(3,5-dimethylpiperazin-1-yl)-5-oxopentanoic acid, 1 g of (16R)-16-deoxo-16-fluoropristinamycin II$_B$ (prepared as described in Example 1), 430 mg of N,N'-dicyclohexylcarbodiimide, 23 mg of 4-dimethylaminopyridine, but in a mixture of 40 cm$^3$ of dichloromethane and 5 cm$^3$ of dimethylformamide, and after stirring for 60 hours, 2.5 g of a brown oil are isolated, which oil is purified by flash chromatography [eluent: dichloromethane-methanol (97–3 by volume)]. After concentrating the fractions to dryness under reduced pressure (2.7 kPa) at 20° C., and then stirring the solid obtained in 10 cm$^3$ of diethyl ether, filtration and drying (90 Pa) at 50° C., 680 mg of (16R)-16-deoxo-16-fluoro-14-O-[4-(3,5-dimethylpiperazin-1-ylcarbonyl)butyryl]pristinamycin II$_B$ are thus obtained in the form of a white solid.

5-(3,5-dimethylpiperazin-1-yl)-5-oxopentanoic acid may be prepared in the following manner:

1.5 g of 2,6-dimethylpiperazine are added, under argon, to a mixture of 30 cm$^3$ of dioxane and 5 cm$^3$ of dichloromethane. After stirring, the residual insoluble matter is filtered and the filtrate is placed in a three-necked flask. 1.5 g of glutaric anhydride in solution in 10 cm$^3$ of dioxane are added dropwise and then the stirring is continued at 25° C. for 2 hours. The solvents are evaporated under reduced pressure (2.7 kPa) to give a solid which is taken up in 100 cm$^3$ of diethyl ether, filtered, rinsed with diethyl ether and then dried at 20° C. (90 Pa) to give 2.19 g of 5-(3,5-dimethylpiperazin-1-yl)-5-oxopentanoic acid in the form of a white solid which is used as it is.

EXAMPLE 52

(16R)-16-Deoxo-16-fluoro-14-O-{4-[4-(methylphenylcarbamoylmethyl)piperazin-1-ylcarbonyl]butyryl}pristinamycin II$_b$ hydrochloride 0.3 cm$^3$ of 3 M hydrochloric ether is added, at 4° C., to 470 mg of (16R)-16-deoxo-16-fluoro-14-O-{4-[4-(methylphenylcarbamoylmethyl)piperazin-1-ylcarbonyl)]butyryl}pristinamycin II$_B$, in solution in 5 cm$^3$ of methyl isobutyl ketone. After stirring for one hour, the precipitate formed is filtered on No. 4 sintered glass and then rinsed successively with a minimum of methyl isobutyl ketone and with diethyl ether. The solid obtained is dried at 20° C. (90 Pa) to give 463 mg of (16R)-16-deoxo-16-fluoro-14-O-{4-[4-(methylphenylcarbamoylmethyl)piperazin-1-ylcarbonyl)]butyryl}-pristinamycin II$_B$ hydrochloride, in the form of a white solid melting at around 155° C.

$^1$H NMR spectrum (500 MHz, (CD$_3$)$_2$SO d6, δ in ppm): 0.87 (mt: 3H); 0.95 (d, J=6.5 Hz: 3H); 1.05 (d, J=6.5 Hz: 3H); 1.53 (mt: 1H); from 1.65 to 1.85 (mt: 3H); 1.77 (s: 3H); from 1.85 to 2.05 (mt: 3H); 2.11 (mt: 1H); 2.19 (mt: 1H); 2.34 (mt: 4H); 2.78 (mt: 1H); from 2.85 to 3.55 and from 3.80 to 4.05 (mt: 1H in total); 3.26 (s: 3H); 3.60 (broad d, J=15 Hz: 1H); 3.69 (mt: 1H); 3.81 (mt: 1H); 3.95 (mt: 1H); from 4.25 to 4.60 (unresolved complex: 1H); from 4.70 to 4.80 (mt: 2H); 5.09 (decoupled doublet, J$_{HF}$=48 Hz: 1H); 5.42 (d, J=9.5 Hz: 1H); 5.62 (mt: 1H); 5.74 (mt: 1H); 5.81 (dd, J=16 and 2 Hz: 1H); 6.19 (d, J=15.5 Hz: 1H); 6.63 (dd, J=16 and 4 Hz: 1H); from 7.25 to 7.60 (mt: 5H); 8.14 (mt: 1H); 8.52 (s: 1H); 10.13 (broad unresolved complex).

(16R)-16-Deoxo-16-fluoro-14-O-{4-[4-(methylphenylcarbamoylmethyl)piperazin-1-ylcarbonyl]butyryl}pristinamycin II$_B$ may be prepared in the following manner:

Carrying out the procedure as in Example 45, but starting with 653 mg of 5-[4-(methylphenylcarbamoylmethyl)piperazin-1-yl]-5-oxopentanoic acid, 1 g of (16R)-16-deoxo-16-fluoropristinamycin II$_B$ (prepared as described in Example 1), 388 mg of N,N'-dicyclohexylcarbodiimide in solution in 10 cm$^3$ of dichloromethane which are added dropwise over 3 hours, 23 mg of 4-dimethylaminopyridine in 50 cm$^3$ of dichloromethane, and after stirring for 22 hours, 1.49 g of a solid are obtained, which solid is purified by flash chromatography [eluent: dichloromethane-methanol (97–3 by volume)]. After concentrating the fractions to dryness under reduced pressure (2.7 kPa) at 20° C., and then stirring the solid obtained in diethyl ether, filtration and drying (90 Pa) at 50° C., 470 mg of (16R)-16-deoxo-16-fluoro-14-O-{4-[4-(methylphenylcarbamoylmethyl)piperazin-1-ylcarbonyl]butyryl}pristinamycin II$_B$ are thus obtained in the form of a white solid.

5-[4-(Methylphenylcarbamoylmethyl)piperazin-1-yl]-5-oxopentanoic acid may be obtained in the following manner:

1.517 g of glutaric anhydride and then 1.715 g of N-[2-(piperazin-1-yl)acetyl]-N-methylaniline are added to 15 cm$^3$ of dioxane. After stirring for 19 hours at 25° C., the white precipitate formed is filtered on No. 4 sintered glass, rinsed with dioxane and then with diethyl ether and then dried at 20° C. (90 Pa) to give 2 g of 5-[4-(methylphenylcarbamoylmethyl)piperazin-1-yl]-5-oxopentanoic acid in the form of a white solid which is used as it is.

EXAMPLE 53

(16R)-16-Deoxo-16-fluoro-14-O-{4-[4-(2-methoxyethyl)piperazin-1-ylcarbonyl]-butyryl}pristinamycin $II_B$ 1 g of (16R)-16-deoxo-16-fluoropristinamycin $II_B$ (prepared as described in Example 1) and 40 cm$^3$ of dichloromethane are added to a round-bottomed flask placed under nitrogen. The mixture is heated until dissolution is obtained and then cooled. 485 mg of 5-[4-(2-methoxyethyl)piperazin-1-yl]-5-oxopentanoic acid and then 45 mg of 4-dimethylaminopyridine are added at 20° C. 388 mg of N,N'-dicyclohexyl-carbodiimide in solution in 10 cm$^3$ of dichloromethane are then added dropwise over 3 hours. After stirring for 18 hours at 20° C., an additional 48 mg of 5-[4-(2-methoxyethyl)piperazin-1-yl]-5-oxopentanoic acid and 38 mg of N,N'-dicyclohexylcarbodiimide in solution in 5 cm$^3$ of dichloromethane are added. The reaction is stirred at 20° C. for 3 hours, and then the reaction mixture is filtered, rinsed with ethyl acetate and the filtrate is concentrated to dryness under reduced pressure (2.7 kPa). The residue obtained is stirred for 0.5 hour in 40 cm$^3$ of ethyl acetate and then filtered. The insoluble matter is rinsed with ethyl acetate. The filtrates are combined and then washed with 10 cm$^3$ of an aqueous solution of water saturated with sodium chloride, dried over magnesium sulfate, filtered and concentrated to dryness under reduced pressure (2.7 kPa). The solid obtained is stirred, first, in 40 cm$^3$ of diisopropyl ether for 18 hours and then filtered and again stirred in a mixture of 40 cm$^3$ of diisopropyl ether and 10 cm$^3$ of ethyl ether. The resulting solid is filtered and then purified by flash chromatography [eluent: dichloromethane-methanol (97-3 by volume)]. A product is thus obtained which is stirred in 40 cm$^3$ of diisopropyl ether, filtered and then dried at 30° C. (90 Pa) to give 815 mg of (16R)-16-deoxo-16-fluoro-14-O-{4-[4-(2-methoxyethyl)piperazin-1-ylcarbonyl]butyryl}pristinamycin $II_B$, in the form of a white powder.

0.35 cm$^3$ of 3 M hydrochloric ether and then, slowly, 20 cm$^3$ of diethyl ether are added to this solid dissolved in 4 cm$^3$ of absolute ethanol. The solvents are evaporated under reduced pressure and the resulting solid is stirred in 20 cm$^3$ of diethyl ether. After filtration and drying at 20° C. (90 Pa), 800 mg of (16R)-16-deoxo-16-fluoro-14-O-{4-[4-(2-methoxyethyl)piperazin-1-ylcarbonyl]butyryl}pristinamycin $II_B$ hydrochloride are obtained in the form of a white solid melting at 170° C.

$^1$H NMR spectrum (400 MHz, (CD$_3$)$_2$SO d6, δ in ppm): 0.86 (d, J=6.5 Hz: 3H); 0.95 (d, J=6.5 Hz: 3H); 1.04 (d, J=6.5 Hz: 3H); 1.52 (mt: 1H); from 1.65 to 2.05 (mt: 6H); 1.77 (s: 3H); from 2.05 to 2.30 (mt: 2H); 2.37 (mt: 4H); 2.78 (mt: 1H); from 2.85 to 3.55 (mt: 13H); 3.59 (mt: 1H); from 3.65 to 3.75 (mt: 3H); 3.81 (mt: 1H); from 3.90 to 4.10 (mt: 2H); 4.42 (broad d, J=13 Hz: 1H); from 4.70 to 4.80 (mt: 2H); 5.10 (decoupled doublet, J$_{HF}$=48 Hz: 1H); 5.43 (d, J=9 Hz: 1H); 5.61 (mt: 1H); 5.74 (mt: 1 H); 5.81 (dd, J=16 and 1.5 Hz: 1H); 6.20 (d, J=16 Hz: 1H); 6.64 (dd, J=16 and 4 Hz: 1H); 8.18 (t, J=6 Hz: 1H); 8.52 (s: 1H); 10.46 (broad) unresolved complex: 1H).

5-[4-(2-Methoxyethyl)piperazin-1-yl]-5-oxopentanoic acid may be obtained in the following manner:

1.52 g of glutaric anhydride and then 1.92 g of 1-(2-methoxyethyl)piperazine in solution in 3 cm$^3$ of dioxane are added to 13 cm$^3$ of dioxane. After stirring for 5 hours at room temperature, an additional 300 mg of glutaric anhydride are added and then the stirring is continued at 20° C. for 18 hours. The solvent is evaporated under reduced pressure and the resulting oil is dried at 20° C. (90 Pa) to give 3.4 g of 5-[4-(2-methoxyethyl)piperazin-1-yl]-5-oxopentanoic acid in the form of an orange-colored lacquer which is used as it is.

EXAMPLE 54

(16R)-16-Deoxo-16-fluoro-14-O-[4-(4-propylpiperazin-1-ylcarbonyl)butyryl]-pristinamycin $II_B$ Carrying out the procedure as in Example 46, but starting with 0.5 g of 5-oxo-5-(4-propylpiperazin-1-yl)pentanoic acid, 1 g of (16R)-16-deoxo-16-fluoro-pristinamycin $II_B$ (prepared as described in Example 1), 430 mg of N,N'-dicyclohexylcarbodiimide, and 23 mg of 4-dimethylaminopyridine in 50 cm$^3$ of dichloromethane, a solid is obtained after stirring for 4 hours at 20° C. and after filtration and evaporation to dryness under reduced pressure of the solvent (2.7 kPa) at 20° C., which solid is purified by flash chromatography [eluent: dichloromethane-methanol (97/3 by volume)]. After concentrating the fractions to dryness under reduced pressure (2.7 kPa) at 20° C., and then stirring the solid obtained in diethyl ether, filtration and drying (90 Pa) at 20° C., 960 mg of (16R)-16-deoxo-16-fluoro-14-O-[4-(4-propylpiperazin-1-ylcarbonyl)butyryl]pristinamycin $II_B$ are obtained in the form of a white powder.

0.75 cm$^3$ of 3 M hydrochloric ether is added to this solid dissolved in 10 cm$^3$ of methyl ethyl ketone. The precipitate obtained is filtered on No. 3 sintered glass, rinsed with twice 10 cm$^3$ of methyl ethyl ketone and then with twice 15 cm$^3$ of diethyl ether. After filtration and drying at 20° C. (90 Pa), 700 mg of (16R)-16-deoxo-16-fluoro-14-O-[4-(4-propylpiperazin-1-ylcarbonyl)butyryl]pristinamycin $II_B$ hydrochloride are obtained in the form of a white solid melting at 145° C.

$^1$H NMR spectrum (400 MHz, (CD$_3$)$_2$SO d6, δ in ppm): 0.86 (d, J=6.5 Hz: 3H); from 0.90 to 1.00 (mt: 6H); 1.04 (d, J=6.5 Hz: 3H); 1.54 (mt: 1H); from 1.60 to 2.25 (mt: 10H); 1.78 (s: 3H); from 2.30 to 2.45 (mt: 4H); 2.76 (mt: 1H); from 2.80 to 3.10 (mt: 6H); 3.21 (mt: 1H); from 3.40 to 3.55 (mt: 3H); 3.60 (mt: 1H); 3.68 (mt: 1H); 3.82 (mt: 1H); from 3.90 to 4.10 (mt: 2H); 4.45 (broad d, J=14 Hz: 1H); from 4.70 to 4.80 (mt: 2H); 5.09 (decoupled doublet, J$_{HF}$=48 Hz: 1H); 5.41 (d, J=9 Hz: 1H); 5.61 (mt: 1H); 5.74 (mt: 1H); 5.80 (broad d, J=16 Hz: 1H); 6.19 (d, J=15.5 Hz: 1H); 6.62 (dd, J=16 and 4 Hz: 1H); 8.14 (broad t, J=5.5 Hz: 1H); 8.48 (s: 1H); 10.41 (broad unresolved complex: 1H).

5-Oxo-5-(4-propylpiperazin-1-yl)pentanoic acid may be obtained in the following manner:

1.5 g of glutaric anhydride and then 1.66 g of N-propylpiperazine in solution in 5 cm$^3$ of dioxane are added to 10 cm$^3$ of dioxane in a round-bottomed flask kept under an argon atmosphere. After stirring for 2.5 hours at room temperature, the solvent is evaporated under reduced pressure and then the resulting oil is supplemented with 100 cm$^3$ of diethyl ether. After stirring for one hour, the solid obtained is filtered, dried at 20° C. (90 Pa) to give 2.47 g of 5-oxo-5-(4-propylpiperazin-1-yl)pentanoic acid in the form of a white solid which is used as it is.

EXAMPLE 55

(16R)-16-Deoxo-16-fluoro-14-O-{4-[4-(3-imidazol-1-ylpropyl)piperazin-1-yl-carbonyl]butyryl}pristinamycin $II_B$ 1.42 g of (16R)-14-O-{4-[4-(3-chloropropyl)piperazin-1-ylcarbonyl]butyryl}-16-deoxo-16-fluoropristinamycin $II_B$, 6 cm³ of dimethylformamide, 0.24 g of imidazole and 10 mg of sodium iodide are added to a round-bottomed flask placed under nitrogen. The mixture is heated at 75° C. for 5 hours and then stirred for 60 hours at 20° C. An additional 0.12 g of imidazole in solution in 2 cm³ of DMF is then added at 20° C. and the stirring is continued for 4 hours at 75° C. and then for 18 hours at 20° C. The mixture obtained is then concentrated to dryness under reduced pressure (2.7 kPa). The resulting solid is taken up in 50 cm³ of dichloromethane and the solution obtained is washed with twice 40 cm³ of distilled water. The organic phase is decanted off, dried over magnesium sulfate, filtered and then concentrated to dryness under reduced pressure to give 1.14 g of a solid which is purified by flash chromatography [eluent: dichloromethane-methanol (gradient 95-5 and then 90-10 by volume)]. A solid is thus obtained which is stirred in diethyl ether for 40 hours, filtered and then dried at 20° C. (90 Pa) to give 290 mg of (16R)-16-deoxo-16-fluoro-14-O-{4-[4-(3-imidazol-1-yl-propyl)piperazin-1-ylcarbonyl]butyryl}pristinamycin $II_B$ in the form of an off-white solid melting at 122° C.

$^1$H NMR spectrum (400 MHz, $CDCl_3$, δ in ppm): 0.96 (d, J=6.5 Hz: 3H); 1.00 (d, J=6.5 Hz: 3H); 1.09 (d, J=6.5 Hz: 3H); from 1.45 to 2.05 (mt: 9H); 1.88 (s: 3H); from 2.10 to 2.30 (mt: 2H); 2.29 (t, J=7 Hz: 2H); 2.37 (mt: 8H); 2.76 (mt: 1H); 2.99 (mt: 1H); 3.23 (mt: 1H); from 3.40 to 3.55 (mt: 3H); 3.62 (mt: 2H); 3.86 (mt: 1H); from 4.00 to 4.10 (mt: 1H); 4.05 (t, J=7 Hz: 2H); 4.53 (mt: 1H); 4.78 (dd, J=10 and 2 Hz: 1H); 4.82 (dd, J=9 and 3 Hz: 1H); 5.12 (decoupled doublet, $J_{HF}$=48 Hz: 1H); 5.31 (d, J=9 Hz: 1H); 5.75 (mt: 1H); from 5.75 to 5.85 (mt: 1H); 5.82 (dd, J=16 and 2 Hz: 1H); 6.00 (mt: 1H); 6.19 (d, J=16 Hz: 1H); 6.52 (dd, J=16 and 5 Hz: 1H); 6.93 (unresolved complex: 1H); 7.08 (broad s: 1H); 7.50 (broads: 1H); 8.12 (s: 1H).

(16R)-14-O-{4-[4-(3-Chloropropyl)piperazin-1-ylcarbonyl]butyryl}-16-deoxo-16-fluoropristinamycin $II_B$ may be obtained by carrying out the procedure as in Example 46 but starting with 0.94 g of 5-[4-(3-chloropropyl)piperazin-1-yl]-5-oxopentanoic acid, 1.5 g of (16R)-16-deoxo-16-fluoropristinamycin $II_B$ (prepared as described in Example 1), 460 mg of N,N'-dicyclohexylcarbodiimide, and 23 mg of 4-dimethyl-aminopyridine in 40 cm³ of dichloromethane. A suspension, which is filtered, is thus obtained after stirring for 23 hours at 20° C. The filtrate is concentrated to dryness under reduced pressure (2.7 kPa) at 20° C., to give a solid which is stirred in diisopropyl ether, filtered and then dissolved in 50 cm³ of dichloromethane. The solution obtained is washed with 30 cm³ of distilled water, decanted off, dried over magnesium sulfate, filtered and concentrated to dryness under reduced pressure (2.7 kPa) at 20° C., to give 1.42 g of (16R)-14-O-{4-[4-(3-chloropropyl)piperazin-1-ylcarbonyl]butyryl}-16-deoxo-16-fluoropristinamycin $II_B$, in the form of a yellow solid which is used as it is.

5-[4-(3-Chloropropyl)piperazin-1-yl]-5-oxopentanoic acid may be obtained in the following manner:

1.5 g of glutaric anhydride and then 2.13 g of N-(chloropropyl)piperazine in solution in 5 cm³ of dioxane and 1 cm³ of dichloromethane are added to 15 cm³ of dioxane in a round-bottomed flask kept under an argon atmosphere. After stirring for 2 hours at 20° C., the solvent is evaporated under reduced pressure (2.7 kPa) at 20° C., to give 3.75 g of 5-[4-(3-chloropropyl)piperazin-1-yl]-5-oxopentanoic acid in the form of a yellow oil which is used as it is.

EXAMPLE 56

(16R)-16-Deoxo-16-fluoro-14-O-[4-(2-morpholino-ethoxycarbonyl)]butyryl}-pristinamycin $II_B$ hydrochloride 0.42 cm³ of 3 M hydrochloric ether is added, at 4° C., to 550 mg of (16R)-16-deoxo-16-fluoro-14-O-[4-(2-morpholinoethoxycarbonyl)]butyryl}pristinamycin $II_B$ in solution in 5.5 cm³ of methyl isobutyl ketone. After stirring for one hour, the precipitate formed is filtered on No. 4 sintered glass, rinsed successively with methyl isobutyl ketone and diethyl ether and then dried at 20° C. (90 Pa) to give 458 mg of (16R)-16-deoxo-16-fluoro-14-O-[4-(2-morpholinoethoxycarbonyl)]butyryl}-pristinamycin $II_B$, in the form of a white solid melting at 168° C.

$^1$H NMR spectrum (500 MHz, $(CD_3)_2SO$ d6, δ in ppm): 0.85 (mt: 3H); 0.94 (d, J=6.5 Hz: 3H); 1.03 (d, J=6.5 Hz: 3H); 1.50 (mt: 1H); from 1.70 to 1.85 (mt: 3H); 1.77 (s: 3H); from 1.85 to 2.05 (mt: 3H); 2.09 (mt: 1H); 2.19 (mt: 1H); 2.38 (mt: 2H); 2.42 (t, J=7 Hz: 2H); 2.77 (mt: 1H); from 3.10 to 3.50 (mt: 8H); 3.58 (broad d, J=15 Hz: 1H); 3.68 (mt: 1H); from 3.70 to 3.85 (mt: 3H); from 3.90 to 4.00 (mt: 3H); 4.39 (mt: 2H); from 4.70 to 4.80 (mt: 2H); 5.09 (decoupled doublet, $J_{HF}$=48 Hz: 1H); 5.42 (d, J=9 Hz: 1H); 5.60 (mt: 1H); 5.74 (mt: 1H); 5.80 (broad d, J=16 Hz: 1H); 6.19 (d, J=16 Hz: 1H); 6.62 (dd, J=16 and 4 Hz: 1H); 8.17 (mt: 1H); 8.52 (s: 1H); 10.50 (broad unresolved complex: 1H).

(16R)-16-Deoxo-16-fluoro-14-O-[4-(2-morpholinoethoxycarbonyl)]butyryl}-pristinamycin $II_B$ may be obtained in the following manner:

Carrying out the procedure as in Example 45, but starting with 461 mg of (2-morpholinoethyl) monoester of glutaric acid, 1 g of (16R)-16-deoxo-16-fluoropristinamycin $II_B$ (prepared as described in Example 1), 388 mg of N,N'-dicyclohexylcarbodiimide, 23 mg of 4-dimethylaminopyridine in 40 cm³ of dichloromethane, and after stirring for 22 hours, 1.33 g of a solid are obtained, which solid is purified by two successive flash chromatographies [eluent: respectively dichloromethane/methanol (97/3 by volume) and dichloromethane/methanol (98/2 by volume)]. After concentrating the fractions to dryness under reduced pressure (2.7 kPa), stirring the solid obtained in diethyl ether, filtration and drying (90 Pa) at 20° C., 550 mg of (16R)-16-deoxo-16-fluoro-14-O-[4-(2-morpholinoethoxycarbonyl)]-butyryl}pristinamycin $II_b$ are obtained in the form of a white solid.

The (2-morpholinoethyl) monoester of glutaric acid may be obtained in the following manner:

1.517 g of glutaric anhydride and then 1.61 cm³ of N-2-hydroxyethylmorpholine are added to 10 cm³ of dioxane. After stirring for 19hours at 25° C., the solvent is evaporated under reduced pressure (2.7 kPa) and the product obtained is dried at 55° C. (90 Pa) to give 3.18 g of the (2-morpholin-4-ylethyl) monoester of glutaric acid in the form of a brown oil which is used as it is.

EXAMPLE 57

(16R)-16-Deoxo-16-fluoro 14-O-{4-[4-(2-morpholinoethyl)piperazin-1-ylcarbonyl]-butyryl}pristinamycin $II_B$ Carrying out the procedure as in Example 46, but starting with 0.7 g of 5-[4-(2-morpholinoethylpiperazin-1-yl)]-5-oxopentanoic acid, 1 g of (16R)-16-deoxo-16-fluoropristinamycin $II_B$ (prepared as described in Example 1), 460 mg of N,N'-dicyclohexylcarbodiimide, and 23 mg of 4-dimethylaminopyridine in 40 cm³ of dichloromethane, a suspension, which is filtered, is obtained after stirring for 4 hours at 20° C. The filtrate is concentrated to dryness under reduced pressure (2.7 kPa) at 20° C., to give a beige powder which is purified by flash chromatography [eluent: dichloromethane-methanol (96-4 by volume)]. After concentrating the fractions to dryness under reduced pressure (2.7 kPa) at 20° C., and then stirring the solid obtained in diisopropyl ether for 36 hours, filtration and drying (90 Pa) at 20° C., 750 mg of a solid are obtained. This solid is again stirred in a mixture of 20 cm³ of diisopropyl ether and 10 cm³ of diethyl ether for 60 hours. After filtration and drying (90 Pa) at 20° C., the solid obtained is stirred at 60° C., in 60 cm³ of diisopropyl ether for 1.5 hours and then filtered and dried (90 Pa) at 20° C. to give 0.55 g of (16R)-16-deoxo-16-fluoro-14-O-{4-[4-(2-morpholinoethyl)piperazin-1-ylcarbonyl]butyryl}pristinamycin II$_B$, in the form of a light yellow powder melting at 116° C.

¹H NMR spectrum (400 MHz, CDCl₃, δ in ppm): 0.96 (d, J=6.5 Hz: 3H); 1.00 (d, J=6.5 Hz: 3H); 1.10 (d, J=6.5 Hz: 3H); from 1.55 to 2,05 (mt: 7H); 1.89 (s: 3H); from 2.10 to 2.30 (mt: 2H); 2.38 (mt: 4H); from 2.40 to 2.60 (mt: 12H); 2.76 (mt: 1H); 2.98 (mt: 1H); 3.23 (mt: 1H); from 3.40 to 3.55 (mt: 3H); 3.61 (mt: 2H); 3.72 (t, J=5 Hz: 4H); 3.86 (mt: 1H); 4.06 (mt: 1H); 4.54 (mt: 1H); 4.79 (dd, J=10 and 1.5 Hz: 1H); 4.82 (dd, J=9 and 3 Hz: 1H); 5.12 (decoupled doublet, J$_{HF}$=48 Hz: 1H); 5.30 (d, J=9 Hz: 1H); 5.75 (mt: 1H); from 5.75 to 5.85 (mt: 1H); 5.82 (dd, J=17 and 1.5 Hz: 1H); 5.96 (mt: 1H); 6.19 (d, J=16 Hz 1H); 6.51 (dd, J=17 and 5 Hz: 1H);8.12(s: 1H).

5-[4-(2-Morpholinoethylpiperazin-1-yl)]-5-oxopentanoic acid may be obtained in the following manner:

1.5 g of glutaric anhydride and then 2.62 g of 1-(2-morpholinoethyl)piperazine in solution in 10 cm³ of dioxane are added to 10 cm³ of dioxane in a round-bottomed flask kept under an argon atmosphere. After stirring for 60 hours at room temperature, the solvent is evaporated under reduced pressure. The resulting oil is supplemented with 100 cm³ of diethyl ether. After cooling to −40° C., the product becomes concreted. The stirring is then continued for 1 hour at 20° C. The solid obtained is filtered, rinsed with diethyl ether and then dried at 20° C. (90 Pa) to give 3.57 g of 5-[4-(2-morpholinoethylpiperazin-1-yl)]-5-oxopentanoic acid in the form of a white solid which is used as it is.

EXAMPLE 58

(16R)-16-Deoxo-16-fluoro-14-O-[(3RS)-3-methyl4 (4-methylpiperazin-1-ylcarbonylbutyryl]pristinamycin II$_B$ hydrochloride Carrying out the procedure as in Example 46, but starting with 516 mg of 3-methyl-5-(4-methylpiperazin-1-yl)-5-oxopentanoic acid, 1 g of (16R)-16-deoxo-16-fluoro-pristinamycin II$_B$ (prepared as described in Example 1), 467 mg of N,N'-dicyclohexylcarbodiimide, and 54 mg of 4-dimethylaminopyridine in 40 cm³ of dichloromethane, 1.25 g of a solid are obtained, which solid is purified by flash chromatography [eluent: dichloromethane/methanol (95/5 by volume)]. After concentrating the fractions to dryness under reduced pressure (2.7 kPa) at 20° C., and then stirring the solid obtained in diisopropyl ether for 18 hours, filtration and drying (90 Pa) at 20° C., 730 mg of (16R)-16-deoxo-16-fluoro-14-O-[(3RS)-3-methyl-4-(4-methylpiperazin-1-ylcarbonyl butyryl]pristinamycin II$_B$ are obtained in the form of a white solid. The latter is dissolved in 3.5 cm³ of absolute ethanol to which 0.34 cm³ of 3 M hydrochloric ether is added. 35 cm³ of diethyl ether are then added and the suspension obtained is stirred for 2 hours at 20° C. The solid is filtered, rinsed with diethyl ether and then dried at 45° C. (90 Pa) to give 645 mg of (16R)-16-deoxo-16-fluoro-14-O-[(3RS)-3-methyl-4-(4-methylpiperazin-1-ylcarbonyl)butyryl]-pristinamycin II$_B$ hydrochloride in the form of a white solid melting at 185° C.

¹H NMR spectrum (400 MHz, (CD₃)₂SO d6, δ in ppm): 0.85 (d, J=6.5 Hz: 3H); from 0.90 to 1.00 (mt: 6H); 1.03 (d, J=6.5 Hz: 3H); 1.51 (mt: 1H); from 1.70 to 2.45 (mt: 11H); 1.77 (s: 3H); from 2.70 to 3.50 (mt: 9H); 2.77 (broad s: 3H); 3.59 (mt: 1H); 3.68 (mt: 1H); 3.80 (mt: 1H); from 3.90 to 4.20 (broad unresolved complex: 1H); 3.97 (mt: 1H); 4,44 (broad unresolved complex: 1H); from 4.70 to 4.80 (mt: 2H); 5.09 (decoupled doublet, J$_{HF}$=48 Hz: 1H); 5.43 (d, J=9 Hz: 1H); 5.61 (mt: 1H); 5.75 (mt: 1H); 5.80 (broad d, J=16 Hz: 1H); 6.19 (d, J=16 Hz: 1H); 6.62 (dd, J=16 and 4 Hz: 1H); 8.17 (t, J=5.5 Hz: 1H); 8.52 (s: 1H); 10.49 (broad unresolved complex: 1H).

(3RS)-3-Methyl-5-(4-methylpiperazin-1-yl)-5-oxopentanoic acid may be obtained in the following manner:

1.6 g of 3-methylglutaric anhydride and then 1.48 cm³ of N-methylpiperazine are added to 20 cm³ of dioxane. After stirring for 4 hours, an additional 320 mg of 3-methylglutaric anhydride are added. The stirring is continued at 20° C. for 18 hours. The solvent is evaporated under reduced pressure (2.7 kPa), at 50° C. The resulting oil is dried at 50° C. (90 Pa) to give 3.1 g of (3RS)-3-methyl-5-(4-methylpiperazin-1-yl)-5-oxopentanoic acid in the form of a yellow lacquer which is used as it is.

EXAMPLE 59

(16R)-16-Deoxo-16-fluoro-14-O-[(RR,SS)-trans-2-(4-methylpiperazin-1-ylcarbonyl)-1-cyclobutanecarbonyl]pristinamycin II$_B$ (50/50 mixture of the two diastereoisomers)

2.0 g of (RR,SS)-trans-2-(4-methylpiperazin-1-ylcarbonyl)-1-cyclobutanecarboxylic acid, 1.24 g of N,N'-dicyclohexylcarbodiimide and 0.49 g of 4-dimethylamino-pyridine are added, at 20° C., under an argon atmosphere, to 2.1 g of (16R)-16-deoxo-16-fluoropristinamycin II$_B$ (prepared as described in Example 1) in solution in 100 cm³ of dichloromethane. After stirring for 24 hours, the reaction mixture is filtered to remove the insoluble matter. The filtrate is concentrated to dryness under reduced pressure (2.7 kPa) to give 5.2 g of a residue which is purified by flash chromatography [eluent: dichloromethane/methanol gradient (97/3 and then 95/5 by volume)]. After stirring in diisopropyl ether, 0.26 g of (16R)-16-deoxo-16-fluoro-14-O-[(RR,SS)-trans-2-(4-methylpiperazin-1-ylcarbonyl)-1-cyclobutanecarbonyl]-pristinamycin II$_B$ (50/50 mixture of the two diastereoisomers) is obtained in the form of a whitish powder.

¹H NMR spectrum (400 MHz, CDCl₃, δ in ppm); (2 diastereoisomers in the proportions 50-50): 0.96 (d, J=6.5 Hz: 3H); 1.00 (d, J=6.5 Hz: 3H); 1.11 (d, J=6.5 Hz: Hz: 3H); from 1.55 to 2.45 (mt: 15H); 1.90 (s: 3H); 2.29 and 2.30 (2 s: 3H in total); 2.77 (mt: 1H); 2.98 (dt, J=17 and 6 Hz: 1H); 3.23 (mt: 1H); from 3.30 to 3.75 (mt: 7H); 3.86 (mt: 1H); 4.06 (mt: 1H); 4.55 (mt: 1H); from 4.75 to 4.85 (mt: 2H); 5.11 (decoupled doublet, J$_{HF}$=48 Hz: 1H); 5.30 (d, J=9 Hz: 1H); from 5.70 to 5.85 (mt: 3H); 5.96 and 6.02 (2 mts: 1H in total); 6.20 (d, J=16 Hz: 1H); 6.52 (mt: 1H); 8.12 (s: 1H).

(RR,SS)-trans-2-(4-Methylpiperazin-1-yl-carbonyl)-1-cyclobutanecarboxylic acid may be prepared in the following manner:

1.1 cm³ of 1-methylpiperazine are added dropwise, at 25° C., under an argon atmosphere, to a solution of 1.8 g of (RR,SS)-trans-1,2-cyclobutanedicarboxylic acid dichloride in 50 cm³ of dichloromethane. After stirring for 4 hours, 10 cm³ of distilled water are added. After stirring for one hour, the reaction mixture is concentrated to dryness under reduced pressure (2.7 kPa) to give a residue which is taken up in 20 cm³ of distilled water. This solution is brought to pH 10 by addition of a 1 N aqueous sodium hydroxide solution. The solution obtained is extracted with 50 cm³ of ethyl acetate, brought to pH 5-6 by addition of a 1 N aqueous hydrochloric acid solution and then concentrated to dryness under reduced pressure (2.7 kPa). Twice, the residue is covered with 50 cm³ of toluene and dried under reduced pressure (2.7 kPa). The residue is taken up in 50 cm³ of ethanol at 50° C., the insoluble matter is removed by filtration and the filtrate is concentrated to dryness under reduced pressure (2.7 kPa). 2.4 g of (RR,SS)-trans-2-(4-methylpiperazin-1-yl-carbonyl)-1-cyclobutanecarboxylic acid are thus obtained in the form of a yellow oil.

(RR,SS)-trans-1,2-cyclobutanedicarboxylic acid dichloride may be prepared in the following manner:

2.2 cm³ of sulfonyl chloride are added, at 20° C., to 1.5 g of (RR,SS)-trans-1,2-cyclobutanedicarboxylic, and then the mixture is heated under reflux for 2 hours. The reaction mixture is then concentrated under reduced pressure (2.7 kPa). Twice, the residue is covered with 50 cm³ of dichloromethane and dried under reduced pressure (2.7 kPa). 1.8 g of (RR,SS)-trans-1,2-cyclobutanedicarboxylic acid dichloride are thus obtained in the form of a yellow oil.

EXAMPLE 60

(16R)-16-Deoxo-16-fluoro-14-O-(1-methylpiperidin-4-ylcarbonyl)pristinamycin II$_A$ methanesulfonate 0.516 g of N,N'-dicyclohexylcarbodiimide is added, at 20° C., to 1.06g of (16R)-16-deoxo-16-fluoropristinamycin II$_A$ (prepared as described in Example 8), 0.23 g of 1-methyl4-piperidinecarboxylic acid, and 0.123 g of 4-dimethylaminopyridine in solution in 40 cm³ of dichloromethane. After stirring for 24 hours, the reaction mixture is washed with 50 cm³ of water, dried over magnesium sulfate, filtered and then concentrated to dryness under reduced pressure (2.7 kPa) to give a residue which is purified by flash chromatography [eluent: dichloromethane/methanol (95/5 by volume)]. A product is obtained which is taken up in 35 cm³ of ethanol and 13.4 cm³ of a 0.1 N aqueous methanesulfonic acid solution and then concentrated to dryness under reduced pressure (2.7 kPa), stirred in diethyl ether, filtered, and concentrated to give a residue which is stirred in 25 cm³ of dichloromethane and 10 cm³ of a 5% aqueous sodium bicarbonate solution. The organic phase is then separated and then concentrated to dryness under reduced pressure (2.7 kPa) to give a residue which is taken up in 20 cm³ of ethanol and 10 cm³ of a 0.1 N aqueous methanesulfonic acid solution. The solution is concentrated to dryness under reduced pressure (2.7 kPa) at 20° C. to give 0.65 g of (16R)-16-deoxo-16-fluoro-14-O-(1-methylpiperidin-4-yl-carbonyl)pristinamycin II$_A$ methanesulfonate in the form of a cream-colored solid.

¹H NMR spectrum (400 MHz, (CD$_3$)$_2$SO d6 at a temperature of 383 K, δ in ppm): 0.93 (d, J=6.5 Hz: 3H); 1.00 (d, J=6.5 Hz: 3H); 1.13 (d, J=6.5 Hz: 3H); from 1.75 to 2.30 (mt: 7H); 1.84 (s: 3H); 2.40 (s: 3H); from 2.55 to 2.85 (mt: 4H); 2.81 (s: 3H); from 2.90 to 3.55 (mt: 6H); 3.79 (broad d, J=16.5 Hz: 1H); 3.94 (dt, J=16.5 and 6.5 Hz: 1H); from 4.05 to 4.25 (mt: 2H); 4.81 (dd, J=9 and 3 Hz: 1H); 4.99 (decoupled doublet, J$_{HF}$=48 Hz: 1H); 5.33 (d, J=9.5 Hz: 1H); 5.75 (dt, J=9.5 and 5 Hz: 1H); 5.81 (mt: 1H); 5.92 (dd, J=16 and 1.5 Hz: 1H); 6.10 (d, J=16 Hz: 1H); 6.28 (t, J=3 Hz: 1H); 6.63 (dd, J=16 and 6.5 Hz: 1H); 7.43 (unresolved complex: 1H); 8.45 (s: 1H); from 8.85 to 9.45 (very broad unresolved complex: 1H).

1-Methyl-4-piperidinecarboxylic acid may be prepared in the following manner:

12.5 cm³ of a 4 N aqueous sodium hydroxide solution are added, at 20° C., to 7.60 g of ethyl 1-methyl-4-piperidinecarboxylate in solution in 35 cm³ of ethanol. After stirring for 20 hours, the reaction mixture is concentrated to a reduced volume and then neutralized with 12.5 cm³ of a 4 N aqueous hydrochloric acid solution and finally concentrated to dryness under reduced pressure (2.7 kPa). The residue is stirred in 60 cm³ of anhydrous ethanol, and then filtered. The filtrate is concentrated to dryness under reduced pressure (2.7 Kpa) at 20° C., to give 6.3 g of 1-methyl-4-piperidinecarboxylic acid in the form of a white solid.

¹H NMR spectrum (300 MHz, (CD$_3$)$_2$SO d6, δ in ppm) 1.56 (mt: 2H); 1.78 (mt: 2H); 1.98 (dt, J=11.5 and 2.5 Hz: 2H); 2.13 (mt: 1H); 2.18 (s: 3H); 2.74 (broad d, J=11.5 Hz: 2H).

Ethyl 1-methyl-4-piperidinecarboxylate may be prepared in the following manner:

12.5 cm³ of a 4 N aqueous sodium hydroxide solution are added, at 20° C., to 9.2 g of ethyl 4-piperidinecarboxylate hydrochloride in 80 cm³ of dichloromethane. After stirring for 5 minutes, the organic phase is dried over magnesium sulfate, filtered and then cooled to 5° C. 7.0 cm³ of formaldehyde and 14.2 g (introduced in two portions) of sodium triacetoxyborohydride are then added under argon. After stirring vigorously for 1 hour at 20° C., the reaction mixture is diluted with 50 cm³ of water, alkalinized with a 4 N aqueous sodium hydroxide solution and then decanted off. The organic phase is dried over magnesium sulfate, filtered and concentrated to dryness under reduced pressure (2.7 kPa) at 20° C., to give 7.6 g of 1-methyl-4-piperidinecarboxylate, in the form of a colorless oil.

¹H NMR spectrum (250 MHz, CDCl$_3$, δ in ppm): 1.24 (t, J=7 Hz: 3H); from 1.65 to 2.05 (mt: 6H); from 2.15 to 2.30 (mt: 1H); 2.25 (s: 3H); 2.81 (broad d, J=11.5 Hz: 2H); 4.13 (q, J=7 Hz: 2H).

EXAMPLE 61

(16R)-16-Deoxo-16-fluoro-14-O-[1-(dimethylaminoacetyl)piperidine-4-carbonyl]-pristinamycin II$_B$ 0.51 g of 1-(dimethylaminoacetyl)piperidine-4-carboxylic acid, 0.5 g of N,N'-dicyclohexylcarbodiimide and 0.15 g of 4-dimethylaminopyridine are added, at 20° C., under an argon atmosphere, to 1.1 g of (16R)-16-deoxo-16-fluoropristinamycin II$_B$ (prepared as described in Example 1) in solution in 50 cm³ of dichloromethane. After stirring for 48 hours, an additional 0.5 g of N,N'-dicyclohexylcarbodiimide and 0.1 g of 4-dimethylaminopyridine are added. After stirring for 48 hours, the reaction mixture is filtered to remove the insoluble matter. The filtrate is concentrated to dryness under reduced pressure (2.7 kPa), to give 1.8 g of a residue which is purified by flash chromatography [eluent: dichloromethane/methanol gradient (97/3 and then 95/5 by volume)]. After stirring in diethyl ether, 0.38 g of (16R)-

16-deoxo-16-fluoro-14-O-[1-(dimethylaminoacetyl)piperidine-4-carbonyl]pristinamycin II$_B$ is obtained in the form of a white solid.

$^1$H NMR spectrum (400 MHz, CDCl$_3$, δ in ppm): 0.96 (d, J=6.5 Hz: 3H); 1.00 (d, J=6.5 Hz: 3H); 1.10 (d, J=6.5 Hz: 3H); from 1.50 to 2.05 (mt: 9H); 1.89 (s: 3H); from 2.10 to 2.35 (mt: 2H); 2.28 (s: 6H); 2.52 (mt: 1H); 2.77 (mt: 1H); 2.80 (mt: 1H); 3.00 (dt, J=17 and 6 Hz: 1H); from 3.05 to 3.20 (mt: 1H); 3.10 (AB, J=14 Hz: 2H); 3.25 (mt: 1H); 3.50 (mt: 1H); 3.85 (mt: 1H); from 4.00 to 4.10 (mt: 2H); 4.38 (mt: 1H); 4.53 (mt: 1H); 4.78 (broad d, J=10 Hz: 1H); 4.82 (dd, J=9 and 3 Hz: 1H); 5.10 (decoupled doublet, J$_{HF}$=48 Hz: 1H); 5.29 (d, J=9 Hz: 1H); from 5.70 to 5.90 (mt: 3H); 5.93 (mt: 1H); 6.19 (d, J=16 Hz: 1H); 6.52 (dd, J=16 and 4 Hz: 1H); 8.12 (s: 1H).

1-(Dimethylaminoacetyl)piperidine-4-carboxylic acid may be prepared in the following manner:

25 cm$^3$ of a 1 N aqueous sodium hydroxide solution are added, at 20° C., to 4.5 g of ethyl 1-(dimethylaminoacetyl)piperidine-4-carboxylate in solution in 50 cm$^3$ of ethanol. After stirring for 16 hours at 50° C., the ethanol is removed under reduced pressure (2.7 kPa) and the residual aqueous phase is extracted with 50 cm$^3$ of ethyl acetate. The aqueous phase is then brought to pH 6 by addition of 1 N hydrochloric acid, and is then concentrated to dyrness under reduced pressure (2.7 kPa). Twice, the residue is covered with 50 cm$^3$ of toluene and dried under reduced pressure (2.7 kPa). The residue is taken up in 50 cm$^3$ of ethanol at 50° C. and the insoluble matter is removed by filtration. The filtrate is concentrated under reduceed pressure (2.7 kPa) to give 4.2 g of 1-(dimethylaminoacetyl)piperidine-4-carboxylic acid in the form of a yellow oil.

$^1$H NMR spectrum (300 MHz, CDCl$_3$, δ in ppm): from 1.50 to 1.80 (mt: 2H); 1.93 (mt: 2H); from 2.40 to 2.60 (mt: 1H); 2.51 (s: 6H); 2.78 (mt: 1H); 3.07 (mt: 1H); 3.25 (d, J=14.5 Hz: 1H); 3.55 (d, J=14.5 Hz: 1H); 3.84 (broad d, J=14 Hz: 1H); 4.39 (broad d, J=14 Hz: 1H).

Ethyl 1-(dimethylaminoacetyl)piperidine-4-carboxylate may be prepared in the following manner:

4.6 g of N-(3-dimethylaminopropyl)-N'-ethylcarbodiimide hydrochloride are added, at 20° C., under an argon atmosphere, to a solution of 2.3 g of N,N-dimethylglycine, 3.2 cm$^3$ of ethyl 4-piperidinecarboxylate, 3.4 cm$^3$ of triethylamine and 0.27 g of hydroxybenzotriazol hydrate in 100 cm$^3$ of dichloromethane. After stirring for 18 hours, the reaction mixture is washed with twice 100 cm$^3$ of distilled water. The organic phase is dried over magnesium sulfate, filtered and then concentrated to dryness under reduced pressure (2.7 kPa). 4.6 g of ethyl 1-(dimethylaminoacetyl)piperidine-4-carboxylate are obtained in the form of a yellow oil.

$^1$H NMR spectrum (250 MHz, (CD$_3$)$_2$SO d6 with addition of a few drops of CD$_3$COOD d4, δ in ppm): 1.22 (t, J=7 Hz: 3H); 1.55 (mt: 2H); 1.88 (mt: 2H); 2.37 (s: 6H); 2.60 (mt: 1H); from 2.90 to 3.15 (mt: 2H); 3.34 (s: 2H); from 3.90 to 4.15 (mt: 2H); 4.11 (q, J=7 Hz: 2H).

EXAMPLE 62

(16R)-16-Deoxo-16-fluoro-14-O-[1-(imidazol-1-ylacetyl)piperidine-4-carbonyl]-pristinamycin II$_B$ 0.15 g of imidazole and 0.18 g of potassium iodide are added, at 20° C., under an argon atmosphere, to 0.8 g of (16R)-16-deoxo-16-fluoro-14-O-(1-chloroacetylpiperidine-4-carbonyl)pristinamycin II$_B$ in solution in 20 cm$^3$ of dimethylformamide. After stirring for 16 hours, 100 cm$^3$ of dichlorome are added. The resulting mixture is washed with twice 50 cm$^3$ of 0.1 N aqueous sodium hydroxide solution. The organic phase is decanted off, dried over magnesium sulfate, filtered and then concentrated to dryness under reduced pressure (2.7 kPa) to give 0.9 g of a residue which is purified by flash chromatography [eluent: dichloromethane/methanol (95/5 by volume)]. After stirring in isopropyl ether, filtration and drying (2.7 kPa) at 20° C., 0.38 g of (16R)-16-deoxo-16-fluoro-14-O-[1-(imidazol-1-ylacetyl)piperidine-4-carbonyl]pristinamycin II$_B$ is obtained in the form of a white powder.

$^1$H NMR spectrum (400 MHz, (CD$_3$)$_2$SO d6, δ in ppm): 0.86 (d, J=6.5 Hz: 3H); 0.95 (d, J=6.5 Hz: 3H); 1.04 (d, J=6.5 Hz: 3H); from 1.35 to 2.30 (mt: 11H); 1.78 (s: 3H); 2.67 (mt: 1H); from 2.75 to 2.85 (mt: 2H); from 3.10 to 3.35 (mt: 3H); 3.61 (broad d, J=15 Hz: 1H); 3.70 (mt: 1H); 3.81 (mt: 2H); 3.97 (mt: 1H); 4.18 (mt: 1H); from 4.70 to 4.80 (mt: 2H); from 4.95 to 5.20 (mt: 1H); 5.00 (limiting AB: 2H); 5.43 (d, J=9 Hz: 1H); 5.62 (mt: 1H); from 5.70 to 5.80 (mt: 1H); 5.80 (dd, J=16 and 2 Hz: 1H); 6.19 (d, J=16 Hz: 1H); 6.63 (dd, J=16 and 4 Hz: 1H); 6.86 (s: 1H); 7.05 (s: 1H); 7.52 (s: 1H); 8.13 (mt: 1H); 8.52 (s: 1H).

(16R)-16-Deoxo-16-fluoro-14-O-(1-chloroacetylpiperidine-4-carbonyl)pristinamycin II$_B$ may be prepared in the following manner:

0.62 g of 1-chloroacetylpiperidine-4-carboxylic acid, 0.62 g of N,N'-dicyclohexyl-carbodiimide and 0.24 g of 4-dimethylaminopyridine are added at 20° C., under an argon atmosphere, to 1.1 g of (16R)-16-deoxo-16-fluoropristinamycin II$_B$ (prepared as described in Example 1) in solution in 50 cm$^3$ of dichloromethane. After stirring for 16 hours at 20° C., the reaction mixture is filtered to remove the insoluble matter. The filtrate is concentrated to dryness under reduced pressure (2.7 kPa) to give 1.8 g of a residue which is purified by flash chromatography [eluent: dichloromethane/methanol (97/3 by volume)]. 0.25 g of (16R)-16-deoxo-16-fluoro-14-O-(1-chloroacetyl-piperidine-4-carbonyl)pristinamycin II$_B$ is thus obtained in the form of a white solid.

$^1$H NMR spectrum (400 MHz, CDCl$_3$, δ in ppm): 0.96 (d, J=6.5 Hz: 3H); 1.01 (d, J=6.5 Hz: 3H); 1.10 (d, J=6.5 Hz: 3H); from 1.70 to 2.05 (mt: 9H); 1.89 (s: 3H); from 2.10 to 2.30 (mt: 2H); 2.55 (mt: 1H); 2.77 (mt: 1H); from 2.90 to 3.05 (mt: 2H); from 3.15 to 3.35 (mt: 2H); 3.51 (mt: 1H); from 3.75 to 3.90 (mt: 2H); from 4.00 to 4.15 (mt: 1H); 4.07 (s: 2H); 4.31 (mt: 1H); 4.52 (mt: 1H); 4.78 (broad d, J=10 Hz: 1H); 4.82 (dd, J=9 and 3 Hz: 1H); 5.10 (decoupled doublet, J$_{HF}$=48 Hz: 1H); 5.29 (d, J=9 Hz: 1H); from 5.75 to 5.90 (mt: 3H); 5.92 (mt: 1H); 6.19 (d, J=16 Hz: 1H); 6.52 (dd, J=17 and 5 Hz: 1H); 8.12 (s: 1H).

1-Chloroacetylpiperidine-4-carboxylic acid may be prepared in the following manner:

10 cm$^3$ of a 1 N aqueous sodium hydroxide solution are added, at 20° C., under an argon atmosphere, to 2.3 g of ethyl 1-chloroacetylpiperidine-4-carboxylate in solution in 25 cm$^3$ of ethanol. After stirring for 16 hours, the ethanol is removed under reduced pressure (2.7 kPa). There are then added to the residue 30 cm$^3$ of distilled water and 1 N hydrochloric acid to pH 4. The solution obtained is concentrated to dryness under reduced pressure (2.7 kPa). Twice, the residue is covered with toluene and dried under reduced pressure (2.7 kPa). 3 g of 1-chloroacetylpiperidine-4-carboxylic acid are thus obtained in the form of a white paste.

$^1$H NMR spectrum (250 MHz, (CD$_3$)$_2$SO d6, δ in ppm): from 1.25 to 1.65 (mt: 2H); from 1.70 to 1.95 (mt: 2H); 2.40

(mt: 1H); 2.79 (mt: 1H); 3.11 (mt: 1H); 3.75 (broad d, J=14 Hz: 1H); from 4.05 to 4.25 (mt: 1H); 4.36 (limiting AB, J=13 Hz: 2H).

Ethyl 1-chloroacetylpiperidine-4-carboxylate may be prepared in the following manner:

8 cm³ of chloroacetyl chloride are added, dropwise over 10 minutes, at 0° C. and under an argon atmosphere, to 15.7 g of ethyl 4-piperidinecarboxylate in solution in 200 cm³ of dichloromethane and 14 cm³ of triethylamine. After stirring for 18 hours at 20° C., the reaction mixture is successively washed with 100 cm³ of distilled water, 100 cm³ of a saturated aqueous sodium hydrogen carbonate solution and 100 cm³ of a saturated aqueous sodium chloride solution. The organic phase is dried over magnesium sulfate, filtered and then concentrated under reduced pressure (2.7 kPa) to give 22 g of ethyl 1-chloroacetylpiperidine-4-carboxylate in the form of a yellow oil.

$^1$H NMR spectrum (400 MHz, $CDCl_3$, δ in ppm): 1.29 (t, J=7 Hz: 3H); from 1.60 to 1.85 (mt: 2H); 1.95 (mt: 2H); 2.54 (mt: 1H); 2.89 (mt: 1H); 3.19 (mt: 1H); 3.81 (broad d, J=14 Hz: 1H); 4.05 (limiting AB, J=12 Hz: 2H); 4.13 (q, J=7 Hz: 2H); 4.31 (broad d, J=14 Hz: 1H).

EXAMPLE 63

(16R)-16-Deoxo-16-fluoro-14-O-[1-(4-morpholin-4-ylbutyryl)piperidine-4-carbonyl]-pristinamycin $II_B$:

The procedure is carried out in a manner similar to that described in Example 60, but starting with 1.80 g of (16R)-16-deoxo-16-fluoropristinamycin $II_B$ (prepared as described in Example 1), 1.20 g of 1-(4-morpholin4-ylbutyryl)piperidine-4-carboxylic acid, 0.24 g of 4-dimethylaminopyridine, 30 cm³ of dimethylformamide, and 0.82 g of N,N'-dicyclohexylcarbodiimide. After treatment, the crude product is purified by flash chromatography [eluent: dichloromethane/methanol (97/3 by volume)] and then by two chromatographies on a CBT1 alumina column [eluent: respectively ethyl acetate/methanol (98/2 by volume) and acetonitrile/diisopropyl ether (50/50 by volume)] to give 0.12 g of (16R)-16-deoxo-16-fluoro-14-O-[1-(4-morpholin-4-ylbutyryl)piperidine-4-carbonyl]pristinamycin $II_B$, in the form of a white solid.

$^1$H NMR spectrum (500 MHz, $(CD_3)_2SO$ d6, δ in ppm). The presence of rotamers is observed in the proportions 60-40: 0.87 (mt: 3H); 0.95 (d, J=6.5 Hz: 3H); 1.04 (mt: 3H); from 1.20 to 2.30 (mt: 13H); 1.70 and 1.78 (2 s: 3H in total); 2.27 (t, J=7.5 Hz: 2H); 2.33 (mt: 6H); 2.62 (mt: 1H); from 2.70 to 2.80 (mt: 2H); 3.10 (mt: (mt: 1H); 3.24 (mt: 1H); from 3.50 to 4.00 (mt: 6H); 3.57 (mt: 4H); 4.22 (mt: 1H); from 4.70 to 4.90 (mt: 2H); 5.09 and from 5.40 to 5.55 (respectively decoupled doublet, $J_{HF}$=48 Hz and mt: 1H in total); from 5.40 to 5.70 (mt: 2H); from 5.70 to 5.85 (mt: 2H); 6.19 and 6.24 (2 d, J=16 Hz: 1H in total); 6.63 (dd, J=16 and 4.5 Hz: 1H); 8.12 and 8.22 (respectively mt and t, J=6 Hz: 1H in total); 8.47 and 8.51 (2 s: 1H in total).

1-(4-Morpholin-4-ylbutyryl)piperidine-4-carboxylic acid may be prepared in the following manner:

6.0 cm³ of a 1 N aqueous sodium hydroxide solution are added to 1.30 g of ethyl 1-(4-morpholin-4-ylbutyryl)piperidine-4-carboxylate in solution in 20 cm³ of ethanol. After stirring for 1.5 hours at 50° C., the reaction mixture is concentrated almost to dryness, diluted in 20 cm³ of water, and the pH is adjusted to 5 by addition of a 1 N aqueous hydrochloric acid solution. After concentrating to dryness under reduced pressure (2.7 kPa), 1.6 g 1-(4-morpholin-4-ylbutyryl)-4-piperidine-carboxylic acid are obtained in the form of a whitish paste.

$^1$H NMR spectrum (400 MHz, $(CD_3)_2SO$ d6, δ in ppm): 1.33 (mt: 1H); 1.46 (mt: 1H); 1.64 (mt: 2H); 1.80 (mt: 2H); from 2.20 to 2.40 (mt: 8H); 2.43 (mt: 1H); 2.69 (mt: 1H); 3.05 (mt: 1H); 3.55 (t, J=4.5 Hz: 4H); 3.79 (broad d, J=13.5 Hz: 1H); 4.20 (broad d, J=13.5 Hz: 1H).

Ethyl 1-(4-morpholin-4-ylbutyryl)piperidine-4-carboxylate may be prepared in the following manner:

0.95 g of N-(3-dimethylaminopropyl)-N'-ethylcarbodiimide in solution in 20 cm³ of dichloromethane is added, at 20° C., to 1.0 g of 4-morpholinobutyric acid, 0.78 g of ethyl isonipecotate, 2.1 cm³ of triethylamine and 20 mg of hydroxybenzotriazole hydrate, in solution in 80 cm³ of dichloromethane. After stirring for 20 hours at 20° C., the reaction mixture is washed with 20 cm³ of water. The organic phase is dried over magnesium sulfate, filtered and concentrated to dryness under reduced pressure (2.7 kPa) to give a pale yellow oil which is purified by chromatography on a CBT1 alumina column [eluent: dichloromethane/methanol (97/3 by volume)]. 1.30 g of ethyl 1-(4-morpholin-4-ylbutyryl)4-piperidinecarboxylate are thus obtained in the form of a pale yellow oil.

$^1$H NMR spectrum (300 MHz, $(CD_3)_2SO$ d6, δ in ppm): 1.20 (t, J=7 Hz: 3H); from 1.25 to 1.60 (mt: 2H); 1.65 (mt: 2H); 1.84 (mt: 2H); from 2.20 to 2.40 (mt: 8H); 2.59 (mt: 1H); 2.70 (mt: 1H); 3.08 (mt: 1H); 3.57 (t, J=5 Hz: 4H); 3.82 (broad d, J=14 Hz: 1H); 4.08 (q, J=7 Hz: 2H); 4.24 (broad d, J=14 Hz: 1H).

4-Morpholinobutyric acid may be prepared according to P. A. Cruickshank, et al., J. Amer. Chem. Soc., 83, 2891 (1961).

EXAMPLE 64

(16R)-16-Deoxo-16-fluoro-14-O-[cis4-(4-morpholinobutyrylamino)-1-cyclohexane-carbonyl]pristinamycin $II_B$:

The procedure is carried out in a manner similar to that described in Example 60, but starting with 3.2 g of (16R)-16-deoxo-16-fluoropristinamycin $II_B$ (prepared as described in Example 1), 2.0 g of cis-4-(4-morpholinobutyrylamino)-1-cyclohexanecarboxylic acid, 0.40 g of 4-dimethylaminopyridine, 75 cm³ of dimethylformamide, and 1.50 g of N,N'-dicyclohexylcarbodiimide. After treatment, the crude product is purified by chromatography on a CBT1 alumina column [eluent: dichloromethane/methanol gradient (100/0 and then 98/2 by volume)], and then by flash chromatography [eluent: dichcloromethane/methanol gradient (100/0; 98/2; 95/5 and then 90/10 by volume)] and again by chromatography on CBT1 alumina [eluent: ethyl acetate/methanol (99/1 by volume)]. 0.40 g of (16R)-16-deoxo-16-fluoro-14-O-[cis-4-(4-morpholinobutyrylamino)-1-cyclohexanecarbonyl]pristinamycin $II_B$ is thus obtained in the form of a white solid.

$^1$H NMR spectrum (500 MHz, $(CD_3)_2SO$ d6, δ in ppm): 0.86 (d, J=6.5 Hz: 3H); 0.94 (d, J=6.5 Hz: 3H); 1.04 (d, J=6.5 Hz: 3H); from 1.35 to 1.70 (mt: 8H); from 1.75 to 2.25 (mt: 9H); 1.78 (s: 3H); 2.08 (t, J=7.5 Hz: 2H); 2.22 (t, J=7.5 Hz: 2H); 2.31 (unresolved complex: 4H); 2.48 (mt: 1H); 2.77 (mt: 1H); from 3.15 to 3.30 (mt: 2H); 3.56 (t, J=5 Hz: 4H); 3.62 (broad d, J=15 Hz: 1H); from 3.65 to 3.75 (mt: 2H); 3.82 (mt: 1H); 3.95 (mt: 1H); from 4.70 to 4.80 (mt: 2H); 5.09 (decoupled doublet, $J_{HF}$=48 Hz: 1H); 5.42 (d, J=9.5 Hz: 1H); 5.62 (mt: 1H); 5.75 (mt: 1H); 5.80 (broad d, J=16 Hz: 1H); 6.19 (d, J=16 Hz: 1H); 6.62 (dd, J=16 and 5 Hz: 1H); 7.65 (d, J=7.5 Hz: 1H); 8.12 (t, J=6 Hz: 1H); 8.51 (s: 1H).

cis-4-(4-Morpholinobutyrylamino)-1-cyclohexanecarboxylic acid may be prepared in the following manner:

6.0 cm³ of a 1 N aqueous sodium hydroxide solution are added to 1.30 g of methyl cis-4-(4-morpholinobutyrylamino)-1-cyclohexanecarboxylate in solution in 20 cm³ of ethanol. After stirring for 1.5 hours at 50° C., the reaction mixture is concentrated almost to dryness, then diluted in 20 cm³ of water and the pH is adjusted to, 5 by addition of a 1 N aqueous hydrochloric acid solution. After concentrating to dryness under reduced pressure (2.7 kPa), 1.5 g of cis-4-(4-morpholinobutyrylamino)-1-cyclohexanecarboxylic acid are obtained in the form of a whitish paste which is used as it is in the next stage.

$^1$H NMR spectrum (400 MHz, CDCl$_3$, δ in ppm): from 1.50 to 1.75 (mt: 6H); from 1.85 to 2.00 (mt: 4H); 2.25 (t, J=7.5 Hz: 2H); 2.44 (mt: 1H); 2.61 (t, J=7.5 Hz: 2H); 2.72 (unresolved complex: 4H); 3.80 (mt: 4H); 3.96 (mt: 1H); 6.72 (d, J=8 Hz: 1H).

Methyl cis-4-(4-morpholinobutyrylamino)-1-cyclohexanecarboxylate may be prepared in the following manner:

The procedure is carried out in a manner similar to that described in Example 63, but starting with 4.20 g of methyl cis-4-aminocyclohexane-1-carboxylate hydrochloride, 4.0 g of 4-morpholinobutyric acid, 50 mg of hydroxybenzotriazole hydrate, 11.2 cm³ of triethylamine, 200 cm³ of dichloromethane and 4.2 g of N-(3-dimethylaminopropyl)-N'-ethylcarbodiimide hydrochloride. After a treatment similar to that in Example 60, the crude product is purified by flash chromatography [eluent: dichloromethane/methanol (95/5 by volume)] to give 5.0 g of methyl cis-4-(4-morpholinobutyrylamino)-1-cyclohexanecarboxylate in the form of a yellow oil.

$^1$H NMR spectrum (400 MHz, (CD$_3$)$_2$SO d6, δ in ppm): from 1.40 to 2.00 (mt: 10H); 2.10 (t, J=7.5 Hz: 2H); 2.25 (t, J=7.5 Hz: 2H); 2.34 (unresolved complex: 4H); from 2.45 to 2.60 (mt: 1H); 3.59 (t, J=5 Hz: 4H); 3.65 (s: 3H); 3.72 (mt: 1H); 7.68 (d, J=7 Hz: 1H).

Methyl cis-4-aminocyclohexane-1-carboxylate hydrochloride may be prepared in the following manner:

5 cm³ of sulfonyl chloride are added dropwise to 50 cm³ of methanol cooled to –10° C. After stirring for 10 minutes at 20° C., 5.0 g of cis-4-aminocyclohexane-1-carboxylic acid are slowly added in fractions. After stirring for 2 hours at ,20° C., the reaction mixture is concentrated to dryness under reduced pressure (2.7 kPa) at 20° C., to give 7.5 g of methyl cis-4-aminocyclohexane-1-carboxylate hydrochloride, in the form of a white powder.

$^1$H NMR spectrum (500 MHz, (CD$_3$)$_2$SO d6 at a temperature of 373 K, δ in ppm). A mixture of diastereoisomers is observed in the proportions 80-20: 1.46 and from 1.60 to 1.70 (2 mts: 4H in total); 1.85 and from 1.95 to 2.15 (2 mts: 4H in total); 2.30 and 2.60 (2 mts: 1H in total); 3.00 and 3.13 (2 mts: 1H in total); 3.64 and 3.67 (2 s: in total); 8.12 (unresolved complex: 3H).

EXAMPLE 65

(16R)-16-Deoxo-16-fluoro-14-O-[N-(4-methylpiperazin-1-ylcarbonyl)glycinyl]-pristinamycin II$_B$ 1.21 g of N,N'-dicyclohexylcarbodiimide, 1.07 g of N-(4-methylpiperazin-1-ylcarbonyl)glycine and 0.13 g of 4-dimethylaminopyridine are added, at 20° C., to 3 g of (16R)-16-deoxo-16-fluoropristinamycin II$_B$ (prepared as described in Example 1) in solution in 100 cm³ of dichloromethane. After stirring for 24 hours at 20° C., 0.6 g of N,N'-dicyclohexylcarbodiimide and 0.065 g of 4-dimethylaminopyridine are added. After stirring for an additional 24 hours at 20° C., the reaction mixture is filtered and the insoluble matter is washed with 70 cm³ of dichloromethane. After two other washing/filtration cycles, the filtrate is concentrated to dryness under reduced pressure (2.7 kPa). The residue is dissolved in 50 cm³ of ethanol and the pH is adjusted to 2 by addition of methanesulfonic acid. After concentrating under reduced pressure (2.7 kPa), the residue is taken up in 50 cm³ of water and extracted with twice 50 cm³ of ethyl acetate. The aqueous phase is decanted off, adjusted to pH 8/9 by addition of a 1 N aqueous sodium hydroxide solution and then extracted with three times 60 cm³ of dichloromethane. The organic phases are combined, washed with 50 cm³ of water, dried over magnesium sulfate, filtered and then concentrated to dryness under reduced pressure (2.7 kPa) to give 2 g of a red oil which is purified by flash chromatography [eluent: dichloro-methane/methanol/acetonitrile gradient (90/5/5 to 80/10/10 by volume)]. 0.222 g of a yellow solid is thus obtained, which solid is stirred for 2 hours in 20 cm³ of diethyl ether to give, after filtration, washing with twice 10 cm³ of diethyl ether and drying under reduced pressure (2.7 kPa), 0.181 g of (16R)-16-deoxo-16-fluoro-14-O-[N-(4-methylpiperazin,-1-ylcarbonyl)glycinyl]pristinamycin II$_B$, in the form of a white solid melting at around 140° C. (dec.).

$^1$H NMR spectrum (400 MHz, CDCl$_3$, δ in ppm): 0.96 (d, J=6.5 Hz: 3H); 1.00 (d, J=6.5 Hz: 3H); 1.09 (d, J=6.5 Hz: 3H); from 1.60 to 2.05 (mt: 5H); 1.89 (s: 3H); 2.15 (mt: 1H); from 2.20 to 2.35 (mt: 1H); 2.31 (s: 3H); 2.40 (mt: 4H); 2.76 (mt: 1H); 2.99 (dt, J=17 and 6 Hz: 1H); 3.23 (mt: 1H); 3.43 (mt: 4H); 3.49 (mt: 1H); 3.85 (mt: 1H); 3.94 (dd, J=18 and 5 Hz: 1H); from 4.00 to 4.10 (mt: 2H); 4.54 (mt: 1H); 4.78 (broad d, J=10 Hz: 1H); 4.82 (dd, J=9 and 3 Hz: 1H); 4.91 (mt: 1H); 5.13 (decoupled doublet, J$_{HF}$=48 Hz: 1H); 5.32 (d, J=9 Hz: 1H); 5.77 (mt: 1H); 5.82 (broad d, J=17 Hz: 1H); 5.86 (mt: 1H); 5.95 (mt: 1H); 6.19 (d, J=16 Hz: 1H); 6.51 (dd, J=17 and 4 Hz: 1H); 8.12 (s: 1H).

N-(4-Methylpiperazin-1-ylcarbonyl)glycine may be prepared in the following manner:

2.36 g of benzyl N-(4-methylpiperazin-1-ylcarbonyl)glycinate are added, at 20° C., under an argon atmosphere, to 0.15 g of 5% palladium on carbon in suspension in 100 cm³ of methanol. After stirring for 2.5 hours at 22° C., under 1.6 bar of hydrogen, 50 cm³ of water are added and the mixture is filtered on Clarcel. The cake is washed with three times 70 cm³ of water at 60° C. The filtrate is then concentrated to dryness under reduced pressure (2.7 kPa) at 50° C. The residue is dried under reduced pressure (2.7 kPa) at 50° C. to give 1.5 g of N-(4-methylpiperazin-1-ylcarbonyl)glycine.

$^1$H NMR spectrum (400 MHz, (CD$_3$)$_2$SO d6 with addition of a few drops of CD$_3$COOD d4, δ in ppm): 2.65 (s: 3H); 2.98 (mt: 4H); 3.51 (mt: 4H); 3.68 (s: 2H).

Benzyl N-(4-methylpiperazin-1-ylcarbonyl)glycinate may be prepared in the following manner:

4.2 cm³ of triethylamine and 3.02 g of benzyl glycinate hydrochloride are added, at 20° C., to 3 g of 4-methylpiperazin-1-ylcarbonyl chloride hydrochloride in solution in 150 cm³ of tetrahydrofuran. After stirring for 16 hours at 60° C., the reaction mixture is concentrated to dryness under reduced pressure (2.7 kPa) and the residue is taken up in 70 cm³ of dichloromethane. The organic phase is successively washed with twice 100 cm³ of a saturated aqueous sodium bicarbonate solution and 70 cm³ of water, and then dried over magnesium sulfate, filtered and concentrated to dryness under reduced pressure (2.7 kPa) to give 1.9 g of benzyl N-(4-methylpiperazin-1-ylcarbonyl)-glycinate in the form of a white solid.

$^1$H NMR spectrum (400 MHz, $(CD_3)_2SO$ d6, δ in ppm): 2.18 (s: 3H); 2.25 (t, J=5 Hz: 4H); 3.30 (t, J=5 Hz: 4H); 3.80 (d, J=6 Hz: 2H); 5.13 (s: 2H); 7.02 (mt: J=6 Hz: 1H); from 7.30 to 7.45 (mt: 5H).

EXAMPLE 66

(16R)-16-Deoxo-16-fluoro-14-O-{4-[(3-carboxy) propyldisulfanyl]butyryl}-pristinamycin II$_B$ 1.25 g of 4,4'-dithiodibutanoic acid, 1.03 g of N,N'-dicyclohexylcarbodiimide and 0.06 g of 4-dimethylaminopyridine are added, at 20° C., under an argon atmosphere, to 1.75 g of (16R)-16-deoxo-16-fluoropristinamycin II$_B$ (prepared as described in Example 1) in solution in 50 cm$^3$ of dichloromethane. After stirring for 18 hours, the reaction mixture is supplemented with 70 cm$^3$ of dichloromethane and then filtered to remove the insoluble matter. The filtrate is then concentrated to dryness under reduced pressure (2.7 kPa), to give 3.3 g of a residue which is purified by two successive flashs chromatographies [eluent: dichloromethane/methanol (96/4 and 97.5/2.5 by volume)]. A residue is obtained which is taken up in 25 cm$^3$ of distilled water and then dissolved by addition of a saturated aqueous sodium hydrogen carbonate solution. The aqueous phase (pH 7–8) is washed with four times 50 cm$^3$ of ethyl acetate and then acidified with a 1 N aqueous hydrochloric acid solution to pH 2–3. A pasty precipitate appears which is dissolved by addition of 250 cm$^3$ of dichloromethane. The organic phase is separated, dried over magnesium sulfate, filtred and then concentrated to dryness under reduced pressure (2.7 kPa), to give 0.7 g of (16R)-16-deoxo-16-fluoro-14-O-{4-[(3-carboxy)propyldisulfanyl]butyryl}-pristinamycin II$^B$ in the form of a white solid.

$^1$H NMR spectrum (400 MHz, CDCl$_3$, δ in ppm): 0.96 (d, J=6.5 Hz: 3H); 0.99 (d, J=6.5 Hz: 3H); 1.11 (d, J=6.5 Hz: 3H); from 1.50 to 2.30 (mt: 11H); 1.90 (s: 3H); from 2.35 to 2.55 (mt: 4H); from 2.65 to 2.85 (mt: 5H); 3.04 (mt: 1H); 3.26 (dt, J=17 and 5 Hz: 1H); 3.56 (mt: 1H); 3.85 (mt: 1H); 4.07 (mt: 1H); 4.53 (mt: 1H); from 4.75 to 4.85 (mt: 2H); 5.08 (decoupled doublet, J$_{HF}$=48 Hz: 1H); 5.29 (d, J=9 Hz: 1H); from 5.75 to 5.90 (mt: 1H); 5.79 (mt: 1H); 5.88 (dd, J=16 and 1.5 Hz: 1H); from 6.10 to 6.25 (mt: 1H); 6.17 (d, J=15.5 Hz: 1H); 6.58 (dd, J=16 and 5 Hz: 1H); 8.13 (s: 1H).

EXAMPLE 67

(16R)-16-Deoxo-16-fluoro-14-O-{4-[3-(4-methylpiperazin-1-ylcarbonyl)propyldi-sulfanyl]butyryl}pristinamycin II$_B$ 0.97 g of N,N'-dicyclohexylcarbodiimide, 0.5 cm$^3$ of 1-methylpiperazine and 0.08 g of 4-dimethylaminopyridine are added, at 20° C., under an argon atmosphere, to 1 g of (16R)-16-deoxo-16-fluoro-14-O-{4-[(3-carboxy)propyldisulfanyl]butyryl}-pristinamycin II$_B$ (prepared as described in Example 70) in solution in 93 cm$^3$ of dichloromethane. After stirring for 96 hours, the reaction mixture is filtered to remove the insoluble matter. The filtrate is concentrated to dryness under reduced pressure (2.7 kPa) to give 2 g of a residue which is purified by flash chromatography [eluent: dichloromethane/methanol (96/4 by volume)]. 0.5 g of (16R)-16-deoxo-16-fluoro-14-O-{4-[3-(4-methylpiperazin-1-ylcarbonyl)propyldisulfanyl]butyryl}pristinamycin II$_B$ is obtained in the form of a white solid.

$^1$H NMR spectrum (400 MHz, CDCl$_3$, δ in ppm): 0.96 (d, J=6.5 Hz: 3H); 1.00 (d, J=6.5 Hz: 3H); 1.10 (d, J=6.5 Hz: 3H); from 1.65 to 2.10 (mt: 9H); 1.88 (s: 3H); 2.15 (mt: 1H); 2.24 (mt: 1H); 2.32 (s: 3H); from 2.35 to 2.50 (mt: 8H); from 2.70 to 2.80 (mt: 1H); 2.71 (t, J=7.5 Hz: 2H); 2.75 (t, J=7 Hz: 2H); 3.00 (mt: 1H); 3.24 (mt: 1H); from 3.40 to 3.55 (mt: 3H); 3.64 (t, J=5 Hz: 2H); 3.86 (mt: 1H); 4.06 (mt: 1H); 4.55 (mt: 1H); 4.78 (dd, J=10 and 2 Hz: 1H); 4.82 (dd, J=9 and 3 Hz: 1H); 5.11 (decoupled doublet, J$_{HF}$=48 Hz: 1H); 5.30 (d, J=9.5 Hz: 1H); from 5.75 to 5.85 (mt: 1H); 5.76 (mt: 1H); 5.81 (dd, J=16 and 2 Hz: 1H); 6.01 (mt: 1H); 6.19 (d, J=16Hz: 1H); 6.52 (dd, J=16 and 5 Hz: 1H); 8.12 (s: 1H).

EXAMPLE 68

(16R)-14-O-(3-Carboxypropionyl)-16-deoxo-16-fluoropristinamycin II$_A$ 560 mg of (16R)-16-Deoxo-16-fluoropristinamycin II$_A$ (prepared as described in Example 8) in solution in 3 cm$^3$ of pyridine are placed in a three-necked flask and then 286 mg of succinic anhydride and then 120 mg of 4-dimethylaminopyridine are added at 20° C. After stirring for 18 hours, the reaction mixture is poured over 50 cm$^3$ of distilled water and 10 cm$^3$ of dichloromethane. The quantity of 0.1 N hydrochloric acid which is sufficient to adjust the pH to 4 is then added. The mixture is filtered on cotton wool to remove the insoluble matter and then decanted off. The aqueous phase is washed with twice 10 cm$^3$ of dichloromethane. The organic phases are combined, supplemented with methanol to complete the solubilization, dried over magnesium sulfate and concentrated to dryness under reduced pressure (2.7 kPa) to give 670 mg of a solid which is purified by flash chromatography [eluent: dichloromethane-methanol (97-3 by voluume)]. 530 mg of a product are thus obtained, which product is again purified by flash chromatography [eluent: dichloromethane-methanol (95-5 by volume)] to give a white solid which is stirred for 15 minutes in 5 cm$^3$ of diethyl ether, filtered and then dried at 50° C. (90 Pa). 147 mg of (16R)-14-O-3-carboxypropionyl)-16-deoxo-16-flouropristinamycin II$_A$ are obtained in the form of a white solid melting at around 156° C. (dec.).

$^1$H NMR spectrum (400 MHz, CDCl$_3$, δ in ppm): 0.99 (mt: 6H); 1.13 (d, J=6.5 Hz: 3H); 1.83 (s: 3H); from 1.90 to 2.10 (mt: 2H); 2.27 (mt: 1H); from 2.50 to 2.90 (mt: 7H); 3.08 (mt: 1H); 3.28 (mt: 1H); 4.00 (broad d, J=18 Hz: 1H); 4.12 (mt: 1H); 4.20 (mt: 1H); 4.30 (mt: 1H); 4.72 (decoupled doublet, J$_{HF}$=48 Hz: 1H); from 4.85 to 5.00 (mt: 2H); 5.67 (mt: 1H); 5.71 (mt: 1H); 5.96 (d, J=16 Hz: 1H); 5.98 (d, J=17 Hz: 1H); 6.18 (broad t, J=2 Hz: 1H); 6.61 (dd, J=17 and 7 Hz: 1H); 7.02 (mt: 1H); 7.96 (s: 1H).

EXAMPLE 69

(16R)-16-Deoxo-16-fluoro-14-O-[3-(4-methylpiperazin-1-ylcarbonyl)propionyl]-pristinamycin II$_A$ hydrochloride To 355 mg of (16R)-16-deoxo-16-fluoro-14-O-[3-(4-methylpiperazin-1-ylcarbonyl)-propionyl]pristinamycin II$_A$ dissolved in 3.5 cm$^3$ of absolute ethanol, there are added 0.167 cm$^3$ of 3 M hydrochloric ether and then, slowly, 7 cm$^3$ of diethyl ether until the product precipitates. After stirring for 15 minutes, the product is filtered, rinsed with a minimum of an ethanol-ether (1/2) mixture and then dried at 20°

C. (90 Pa) to give 305 mg of (16R)-16-deoxo-16-fluoro-14-O-[3-(4-methylpiperazin-1-ylcarbonyl)-propionyl]pristinamycin II$_A$ hydrochloride, in the form of a white solid melting 192° C.

$^1$H NMR spectrum (400 MHz, (CD$_3$)$_2$SO d6, δ in ppm): 0.87 (d, J=6.5 Hz: 3H); 0.96 (d, J=6.5 Hz: 3H); 1.10 (d, J=6.5 Hz: 3H); 1.78 (s: 3H); 1.93 (mt: 1H); 2.02 (mt: 1H); 2.18 (mt: 1H); from 2.50 to 2.80 (mt: 7H); 2.78 (s: 3H); from 2.80 to 3.55 (mt: 8H); 3.66 (broad d, J=16 Hz: 1H); from 3.90 to 4.25 (mt: 3H); 4.14 (mt: 1H); from 4.25 to 4.55 (unresolved complex: 1H); 4.77 (dd, J=9 and 1.5 Hz: 1H); 5.05 (decoupled doublet, J$_{HF}$=48 Hz: 1H); 5.38 (d, J=9.5 Hz: 1H); 5.71 (mt: 2H); 5.88 (d, J16 Hz: 1H); 6.12 (d, J=16 Hz: 1H); 6.36 (broad t, J=2 Hz: 1H); 6.62 (dd, J=16 and 5.5 Hz: 1H); 8.03 (mt 1H); 8.61 (s: 1H); 10.58 (unresolved complex: 1H).

(16R)-16-Deoxo-16-fluoro-14-O-[3-(4-methylpiperazin-1-ylcarbonyl)propionyl]pristinamycin II$_A$ may be prepared in the following manner:

848 mg of (16R)-16-deoxo-16-fluoropristinamycin II$_A$ (prepared as described in Example 8), 24 cm$^3$ of dichloromethane and 352 mg of 4-(4-methylpiperazin-1-yl)-4-oxobutyric acid are introduced into a round-bottomed flask placed under nitrogen. The mixture obtained is heated until dissolution is obtained and then there are added, at room temperature, 360 mg of N,N'-dicyclohexylcarbodiimide and 20 mg of 4-dimethylaminopyridine. After stirring for 18 hours at 20° C., an additional 36 mg of N,N'-dicyclohexylcarbodiimide and 20 mg of 4-dimethylaminopyridine are added. The reaction medium is then stirred at 20° C. for 1 week and then filtered, rinsed with ethyl acetate and concentrated to dryness under reduced pressure (2.7 kPa). The thick oil obtained is taken up in 15 cm$^3$ of ethyl acetate and 30 cm$^3$ of dichloromethane. The organic phase is washed with 3 times 30 cm$^3$ of distilled water, decanted off, dried over magnesium sulfate, filtered and then concentrated to dryness under reduced pressure (2.7 kPa) at 20° C., to give 1.05 g of a yellow oil which is purified by flash chromatography [eluent: dichloromethane-methanol (95-5 by volume)]. 840 mg of a product are thus obtained, which product is stirred in 16 cm$^3$ of diethyl ether for 18 hours, filtered and then dried at 20° C. (90 Pa) to give 640 mg of (16R)-16-deoxo-16-fluoro-14-O-[3-(4-methylpiperazin-1-ylcarbonyl)propionyl]pristinamycin II$_A$ in the form of a white solid melting at 130° C.

4-(4-Methylpiperazin-1-yl)-4-oxobutyric acid may be prepared in the following manner:

1.17 g of succinic anhydride and then 1.19 cm$^3$ of N-methylpiperazine are added to 20 cm$^3$ of dioxane. After stirring for 18 hours at room temperature, the precipitate obtained is filtered, rinsed with a minimum of dioxane and then, successively, with twice 10 cm$^3$ of acetone and 10 cm$^3$ of diethyl ether. After drying under reduced pressure (2.7 kPa) at 20° C., 1.09 g of 4-(4-methylpiperazin-1-yl)-4-oxobutyric acid are obtained in the form of a white solid melting at 114° C.

EXAMPLE 70

(16R)-14-O-(4-Carboxybutyryl)-16-deoxo-16-fluoropristinamycin II$_A$ 0.68 g of glutaric anhydride and 0.24 g of 4-dimethylaminopyridine are added, at 20° C., under an argon atmosphere, to 1.05 g of (16R)-16-deoxo-16-fluoropristinamycin II$_A$ (prepared as described in Example 8) in solution in 5.5 cm$^3$ of pyridine. After stirring for 24 hours, the reaction mixture is concentrated to dryness under reduced pressure (2.7 kPa) to give a residue which is taken up in 110 cm$^3$ of ethyl acetate and 55 cm$^3$ of distilled water. The organic phase is decanted off, washed successively with twice 55 cm$^3$ of distilled water, 55 cm$^3$ of a 0.1 N aqueous hydrochloric acid solution, twice 55 cm$^3$ of distilled water and twice 55 cm$^3$ of a saturated aqueous sodium chloride solution. After drying over magnesium sulfate and filtration, the organic phase is concentrated to dryness under reduced pressure (2.7 kPa). 0.95 g of a residue is obtained, which residue is dissolved in 100 cm$^3$ of dichloromethane and extracted with 100 cm$^3$ of a 1% aqueous sodium hydrogen carbonate solution. The emulsion obtained is supplemented with 500 cm$^3$ of ethyl acetate to allow decantation. The aqueous phase is then separated, washed again with three times 100 cm$^3$ of ethyl acetate, acidified with a 1 N aqueous hydrochloric acid solution until a pH of close to 2 is obtained and then extracted three times with dichloromethane (200, 100 and 100 cm$^3$). The organic phases are combined, dried over magnesium sulfate, filtered and then concentrated to dryness under reduced pressure (2.7 kPa). 0.33 g of (16R)-14-O-(4-carboxybutyryl)-16-deoxo-16-fluoro-pristinamycin II$_A$ is thus obtained in the form of a beige solid melting at 116° C. (dec.).

$^1$H NMR spectrum (400 MHz, CDCl$_3$, δ in ppm): 0.98 (mt: 6H); 1.12 (d, J=6.5 Hz): 3H); from 1.80 to 2.10 (mt: 4H); 1.82 (s: 3H); from 2.15 to 2.45 (mt: 5H); from 2.65 to 2.90 (mt: 3H); 3.08 (mt: 1H); 3.26 (dt, J=16 and 3.5 Hz: 1H); 3.99 (broad d, J=18 Hz: 1H); from 4.05 to 4.35 (mt: 3H); 4.71 (decoupled doublet, J$_{HF}$=48 Hz: 1H); from 4.85 to 5.00 (mt: 2H); from 5.60 to 5.75 (mt: 2H); 5.96 (d, J=16 Hz: 1H); 5.98 (broad d, J=16 Hz: 1H); 6.18 (t, J=3 Hz: 1H); 6.61 (dd, J=16 and 7 Hz: 1H); 7.09 (t, J=5.5 Hz: 1H); 7.95 (s: 1H).

EXAMPLE 71

(16R)-16-Deoxo-16-fluoro-14-O-[4-(4-methylpiperazin-1-ylcarbonyl)butyryl]-pristinamycin II$_A$ 0.48 g of 4-(4-methylpiperazin-1-ylcarbonyl)butyric acid, 0.48 g of N,N'-dicyclohexylcarbodiimide and 0.14 g of 4-dimethylaminopyridine are added, at 20° C., under an argon atmosphere, to 1 g of (16R)-16-deoxo-16-fluoropristinamycin II$_A$ (prepared as described in Example 8) in solution in 30 cm$^3$ of dichloromethane. After stirring for 20 hours at 20° C., the reaction mixture is poured over 50 cm$^3$ of distilled water and 10 cm$^3$ of dichloromethane. The resulting mixture is filtered to remove the insoluble matter. The organic phase is decanted off and then the aqueous phase is extracted with twice 10 cm$^3$ of dichloromethane. The organic phases are combined, dried over magnesium sulfate, filtered, and then concentrated to dryness under reduced pressure (2.7 kPa), to give 1.6 g of a residue which is purified by two successive flash chromatographies [eluent: dichloromethane/methanol (95/5 by volume)]. After stirring in diethyl ether, filtration and drying (2.7 kPa), 0.6 g of (16R)-16-deoxo-16-fluoro-14-O-[4-(4-methylpiperazin-1-ylcarbonyl)butyryl]-pristinamycin II$_A$ is obtained in the form of a pasty solid melting at around 120° C.

$^1$H NMR spectrum (500 MHz, CDCl$_3$, δ in ppm): 0.99 (mt: 6H); 1.13 (d, J=6.5 Hz: 3H); 1.84 (s: 3H); from 1.90 to 2.10 (mt: 2H); 1.92 (mt: 2H); from 2.15 to 2.45 (mt: 9H); 2.30 (s: 3H); from 2.65 to 2.90 (mt: 3H); 3.07 (mt: 1H); 3.27 (dt, J=15 and 3.5 Hz: 1H); 3.46 (mt: 2H); 3.63 (mt: 2H); 3.99 (broad d, J=17.5 Hz: 1H); from 4.10 to 4.25 (mt: 2H); 4.30 (mt: 1H); 4.71 (decoupled doublet, J$_{HF}$=48 Hz: 1H); 4.90(d, J=9.5Hz: 1H); 4.95(dd, J=10 and 2 Hz: 1H); 5.65(dt, J=9.5and 4 Hz: 1H); 5.72 (mt: 1H); 5.96 (d, J=16 Hz: 1H); 5.98 (broad d, J=16.5 Hz: 1H); 6.17 (t, J=3 Hz: 1H); 6.60 (dd, J=16.5 and 7 Hz: 1H); 7.02 (t, J=5.5 Hz: 1H); 7.94 (s: 1H).

4-(4-Methylpiperazin-1-ylcarbonyl)butyric acid may be prepared according to DE 78-2851953.

EXAMPLE 72

(16R)-16-Deoxo-16-fluoro-14-O-{(1R,2R)-[2-(4-methylpiperazin-1-yl)carbonyl]-1-cyclohexanecarbonyl}pristinamycin II$_B$:

The procedure is carried out in a manner similar to that described in Example 60 but starting with 0.83 g of (16R)-16-deoxo-16-fluoropristinamycin II$_B$ (prepared as described in Example 1), 0.40 g of (1R,2R)-2-[(4-methylpiperazin-1-yl)carbonyl]-1-cyclohexanecarboxylic acid, 0.10 g of 4-dimethylaminopyridine, 30 cm$^3$ of dichloromethane, and 0.40 g of N,N'-dicyclohexylcarbodiimide. After a treatment similar to that in Example 60, the crude product is purified by flash chromatography [eluent: dichloromethane/acetonitrile/methanol (90/5/5 by volume)] and then by chromatography on a CBT1 alumina column [eluent: ethyl acetate/methanol (98/2 by volume)] to give 0.40 g of (16R)-16-deoxo-16-fluoro-14-O-{(1R,2R)-[2-(4-methyl-piperazin-1-yl)carbonyl]-1-cyclohexanecarbonyl}pristinamycin II$_B$, in the form of a white solid.

$^1$H NMR spectrum (400 MHz, CDCl$_3$, δ in ppm): 0.95 (d, J=6.5 Hz: 3H); 0.99(d, J=6.5 Hz: 3H); 1.09 (d, J=6.5 Hz: 3H); from 1.20 to 1.45 (mt: 4H); from 1.55 to 2.45 (mt: 17H); 1.83 (s: 3H); 2.50 (mt: 1H); from 2.70 to 2.85 (mt: 3H); 3.00 (mt: 1H); 3.22 (mt: 1H); 3.44 (mt: 1H); from 3.45 to 3.65 (mt: 4H); 3.88 (mt: 1H); 4.04 (mt: 1H); 4.53 (mt: 1H); from 4.70 to 4.85 (mt: 2H); 5.10 (decoupled doublet, J$_{HF}$=48 Hz: 1H); 5.29 (d, J=10 Hz: 1H); from 5.65 to 5.80 (mt: 2H); 5.81 (broad d, J=16 Hz: 1H); 6.02 (mt: 1H); 6.18 (d, J=16 Hz: 1H); 6:50 (dd, J=16 and 4 Hz: 1H); 8.12 (s: 1H).

(1R,2R)-2-[(4-Methylpiperazin-1-yl)carbonyl]-1-cyclohexanecarboxylic acid may be prepared in the following manner:

0.37 cm$^3$ of N-methylpiperazine in solution in 5 cm$^3$ of dioxane is added, under an argon atmosphere, to 0.50 g of (−)-trans-1,2-cyclohexanedicarboxylic anhydride in solution at −15° C. in 20 cm$^3$ of dioxane. After 1.25 hours at 20° C., the reaction mixture is filtered, the solid is washed with 20 cm$^3$ of diethyl ether, drained, and then dried under reduced pressure (2,7 kPa) at 20° C., to give 0.65 g of (1R,2R)-2-(4-methylpiperazin-1-yl)carbonyl]-1-cyclohexanecarboxylic acid in the form of a white solid.

$^1$H NMR spectrum (400 MHz, CDCl$_3$, δ in ppm): from 1.20 to 1.60 (mt: 4H); from 1.65 to 1.90 (mt: 3H); from 2.05 to 2.35 (mt: 3H); 2.37 (s: 3H); from 2.70 to 2.95 (mt: 5H); 3.43 (mt: 1H); 3.84 (broad d, J=13.5 Hz: 1H); 4.30 (d, J=12.5 Hz: 1H).

EXAMPLE 73

(16R)-16-Azido-16-deoxopristinamycin II$_B$

Carrying out the procedure in a manner similar to Example 4, but starting with tetra-n-butylammonium azide, (16R)-16-azido-16-deoxopristinamycin II$_B$ is obtained in the form of a white solid melting at around 135° C. (dec.).

$^1$H NMR spectrum (400 MHz, CDCl$_3$, δ in ppm): 0.96 (d, J=6.5 Hz: 3H); 1.01 (d, J=6.5 Hz: 3H); 1.10 (d, J=6.5 Hz: 3H); from 1.50 to 1.65 (mt: 1H); from 1.75 to 2.05 (mt: 5H); 1.88 (s: 3H); 2.15 (mt: 1H); 2.77 (mt: 1H); 2.90 (dd, J=17 and 6 Hz: 1H); 3.15 (dd, J=17 and 7 Hz: 1H); 3.49 (mt: 1H); 3.88 (mt: 1H); from 3.95 to 4.15 (mt: 2H); 4.54 (mt: 1H); from 4.70 to 4.80 (mt: 2H); 4.83 (dd, J=9 and 3 Hz: 1H); 5.37 (d, J=9.5 Hz: 1H); 5.75 (mt: 1H); 5.82 (dd, J=17 and 1.5 Hz: 1H); 5.97 (mt: 1H); 6.22 (d, J=16 Hz: 1H); 6.52 (dd, J=17 and 5 Hz: 1H); 8.15 (s: 1H).

The present invention also relates to the pharmaceutical compositions containing at least one streptogramin derivative according to the invention, in the pure state, combined with at least one group B streptogramin derivative, where appropriate in salt form, and/or in the form of a combination with one or more compatible and pharmaceutically acceptable diluents or adjuvants.

The compositions according to the invention may be used by the oral, parenteral, topical or rectal routes or in the form of aerosols.

As solid compositions for oral administration, tablets, pills, gelatin capsules, powders or granules may be used. In these compositions, the active product according to the invention, generally in the form of a combination, is mixed with one or more inert diluents or adjuvants, such as sucrose, lactose or starch. These compositions may comprise substances other than diluents, for example a lubricant such as magnesium stearate or a coating intended for a controlled release.

As liquid compositions for oral administration, there may be used solutions which are pharmaceutically acceptable, suspensions, emulsions, syrups and elixirs containing inert diluents such as water or paraffin oil. These compositions may also comprise substances other than diluents, for example wetting, sweetening or flavoring products.

Compositions for parenteral administration may be emulsions or sterile solutions. As solvent or vehicle, there may be used propylene glycol, a polyethylene glycol, vegetable oils, in particular olive oil, or injectable organic esters, for example ethyl oleate. These compositions may, also contain adjuvants, in particular wetting, isotonizing, emulsifying, dispersing and stabilizing agents.

Sterilization may be carried out in several ways, for example with the aid of a bacteriological filter, by irradiation or by heating. They may also be prepared in the form of sterile solid compositions which may be dissolved at the time of use in sterile water or any other injectable sterile medium.

Compositions for topical administration may be, for example, creams, ointments, lotions or aerosols.

Compositions for rectal administration are suppositories or rectal capsules which contain, in addition to the active ingredient, excipients such as cocoa butter, semisynthetic glycerides or polyethylene glycols.

The compositions may also be aerosols. For use in the form of liquid aerosols, the compositions may be stable sterile solutions or solid compositions which are dissolved at the time of use in apyrogenic sterile water, in saline or any other pharmaceutically acceptable vehicle. For use in the form of dry aerosols intended to be directly inhaled, the active ingredient is finely decoupled and combined with a water-soluble solid diluent or vehicle with a particle size distribution of 30 to 80 μm, for example dextran, mannitol or lactose.

In human therapy, the new streptogramin derivatives according to the invention are particularly useful in the treatment of infections of bacterial origin. The doses depend on the desired effect and the duration of treatment. The doctor will determine the dosage which he judges to be the most appropriate depending on the treatment, depending on the age, weight and degree of infection and other factors specific to the subject to be treated. Generally, the doses are between 0.5 and 3 g of active product in 2 or 3 doses per day orally or parenterally for an adult.

The following example illustrates a composition according to the invention.

EXAMPLE

Tablets containing a dose of 250 mg of active product and having the following composition are prepared according to the usual technique:

| | |
|---|---|
| (16R)-16-deoxo-16-fluoropristinamycin IIB | 175 mg |
| pristinamycin $I_B$ | 75 mg |
| excipient: starch, hydrated silica, dextrin, gelatin, magnesium stearate: qs | 500 mg |

The invention claimed is:

1. A pharmaceutical composition comprising (1) at least one group A streptogramin compound of formula (I) or a salt thereof, (2) at least one group B streptogramin compound, and optionally (3) at least one pharmaceutically acceptable diluent or adjuvant, wherein formula (I) has the following formula:

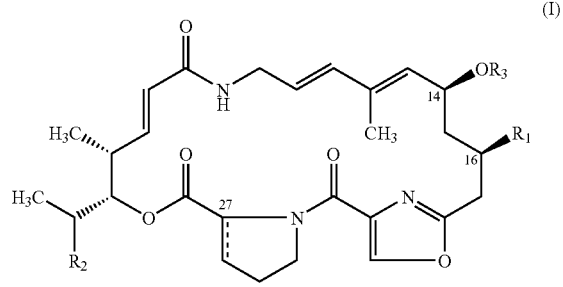

in which $R_1$ is chosen from a halogen atom, an azido group, and a thiocyanato group;

$R_2$ is chosen from a hydrogen atom, a methyl group, and an ethyl group;

$R_3$ is chosen from a hydrogen atom, an aliphatic ester, a cycloaliphatic ester, an aromatic ester, an araliphatic ester, a heterocyclic ester, and a heterocyclylaliphatic ester, wherein said esters may be substituted or unsubstituted; and the bond --- represents a single bond (stereochemistry 27R) or a double bond.

2. A pharmaceutical composition according to claim 1, wherein the group B streptogramin compound is chosen from pristinamycin $I_A$, pristinamycin $I_B$, pristinamycin $I_C$, pristinamycin $I_D$, pristinamycin $I_E$, pristinamycin $I_F$, pristinamycin $I_G$, virginiamycin $S_1$, $S_3$, and $S_4$, vernamycin B and C, and etamycin.

3. A pharmaceutical composition according to claim 2, wherein the group B streptogramin compound is chosen from a semisynthetic compound of formula (A):

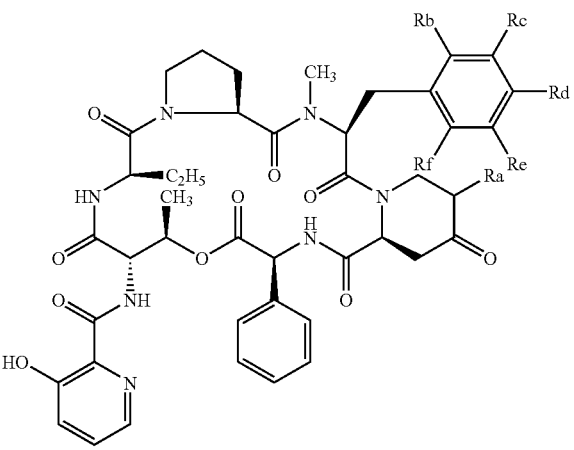

wherein, (1) Rb, Rc, Re and Rf are each a hydrogen atom;

Rd is chosen from a hydrogen atom and a dimethylamino group; and

Ra is chosen from:
(A) —CH$_2$R'a, wherein R'a is chosen from (i) 3-pyrrolidinylthio, (ii) 3-piperidylthio, (iii) 4-piperidylthio, wherein said groups (i)–(iii) may each be unsubstituted or substituted with at least one alkyl, (iv) alkylthio substituted with 1 or 2 groups chosen from:
(a) hydroxysulfonyl, (b) alkylamino, (c) dialkylamino, (d) unsubstituted or substituted piperazine rings, (e) morpholino, (f) thiomorpholino, (g) piperidino, (h) 1-pyrrolidinyl, (i) 2-piperidyl, (j) 3-piperidyl, (k) 4-piperidyl, (l) 2-pyrrolidinyl, or (m) 3-pyrrolidinyl;
(B) =CHR'a, wherein R'a is chosen from:
(i) 3-pyrrolidinylamino, 3-piperidylamino, 4-piperidylamino, 3-pyrrolidinyloxy, 3-piperidyloxy, 4-piperidyloxy, 3-pyrrolidinylthio, 3-piperidylthio, and 4-piperidylthio, which may each be substituted with at least one alkyl, and
(ii) alkylamino, alkyloxy, and alkylthio wherein said alkylamino, said alkyloxy, and said alkylthio are substituted with 1 or 2 groups chosen from:
(a) hydroxysulfonyl, (b) alkylamino, (c) dialkylamino unsubstituted or substituted with dialkylamino, (d) trialkylammonio, (e) 4-imidazolyl, (f) 5-imidazolyl, (g) unsubstituted or substituted piperazine rings, (h) morpholino, (i) thiomorpholino, (j) piperidino, (k) 1-pyrrolidinyl, (l) 2-piperidyl, (m) 3-piperidyl, (n) 4-piperidyl, (o) 2-pyrrolidinyl, or (p) 3-pyrrolidinyl; and
(C) a 3- or 4-quinuclidinylthiomethyl group; or (2) Ra is a hydrogen atom, and Rb, Rc, Rd, Re, and Rf are chosen from:
(a) Rb, Re, and Rf are each a hydrogen atom,
Rd is chosen from —NHCH$_3$ and —N(CH$_3$)$_2$, wherein when Rd is —NHCH$_3$, Rc is chosen from chlorine and bromine, and wherein when Rd is —N(CH$_3$)$_2$, then Rc is chosen from chlorine, bromine, and an alkenyl group containing from 3 to 5 carbon atoms, (b) Rb, Rd, Re and Rf are each a hydrogen atom, and
Rc is chosen from a halogen atom, an aminomonoalkyl, an aminodialkyl, an alkyloxy, a trifluoromethyloxy, a thioalkyl, a ($C_1$ to $C_3$) alkyl group, and a trihalomethyl group,
(c) Rb, Rc, Re, and Rf are each a hydrogen atom, and
Rd is chosen from a halogen atom, an ethylamino, a diethylamino, a methylethylamino, an alkyloxy, a trifluoromethyloxy, a thioalkyl, an ($C_1$ to $C_6$) alkyl group, an aryl group, and a trihalomethyl group,
(d) Rb, Re, and Rf are each a hydrogen atom,
Rc is chosen from a halogen atom, an aminomonoalkyl, an aminodialkyl, an alkyloxy, a trifluoromethyloxy, a thioalkyl, and a ($C_1$ to $C_6$) alkyl group, and
Rd is chosen from a halogen atom, an amino, an aminomonoalkyl, an aminodialkyl, an alkyloxy, a trifluoromethyloxy, a thioalkyl, a ($C_1$ to $C_6$) alkyl group, and a trihalomethyl group, and
(e) Rc, Re and Rf are each a hydrogen atom, and
Rb and Rd are each a methyl group.

4. A pharmaceutical composition according to claim 1, wherein the group B streptogramin compound is a semisynthetic compound of formula (B) or a salt thereof:

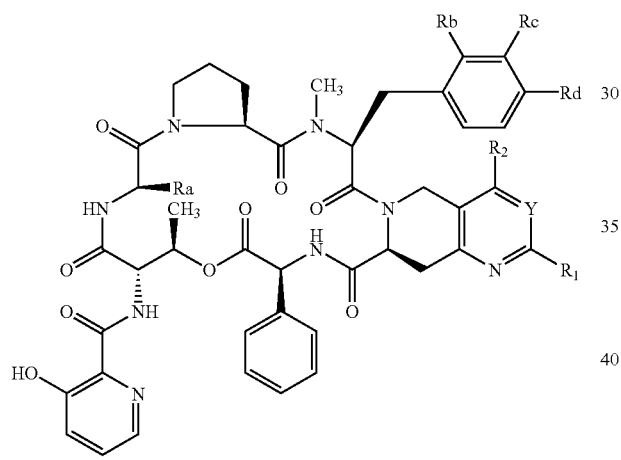

(B)

wherein,
Y is $=CR_3-$;
$R_1$ is chosen from:
(1) a hydrogen atom,
(2) a ($C_1$ to $C_8$) alkyl group,
(3) a ($C_2$ to $C_8$) alkenyl group,
(4) a ($C_3$ to $C_8$) cycloalkyl group,
(5) a ($C_3$ to $C_8$) saturated or unsaturated heterocyclyl group,
(6) an unsubstituted phenyl group,
(7) a substituted phenyl group which is substituted with one or more halogen atoms, hydroxyl groups, alkyl groups, alkyloxy groups, alkylthio groups, alkylsulfinyl groups, alkylsulfonyl groups, amino groups, alkylamino groups, or dialkylamino groups, and
(8) a group NR'R", wherein R' and R", which may be identical or different, are chosen from: (i) a hydrogen atom, (ii) a ($C_1$ to $C_3$) alkyl group, (iii) a halomethyl, (iv) a hydroxymethyl, (v) an alkyloxymethyl, (vi) an alkylthio-methyl in which the alkyl portion may be unsubstituted or substituted with NR'R", (vii) an alkylsulfinylmethyl, (viii) an alkylsulfonylmethyl, (ix) an acyloxymethyl, (x) a benzoyloxy-methyl, (xi) a cyclopropylaminomethyl, (xii) a $-(CH_2)_nNR'R"$ group, wherein n is an integer ranging from 1 to 4, and (xiii) a 3- to 8-membered heterocycle formed with the nitrogen atom to which they are attached, and if $R_3$ is a hydrogen atom, $R_1$ may also be chosen from a formyl, a carboxyl, an alkyloxycarbonyl, and a $-CO-NR'R"$ group, wherein R' and R' are defined as above;

$R_2$ is chosen from a hydrogen atom and a ($C_1$ to $C_3$) alkyl group;

$R_3$ is chosen from a hydrogen atom, an alkyl group, a carboxyl group, an alkyloxycarbonyl group, and a $-CO-NR'R"$ group, wherein R' and R" are defined as above;

Ra is chosen from a methyl group and an ethyl group; and

Rb, Rc and Rd are defined below:
a) Rb and Rc are each a hydrogen atom; and
Rd is chosen from a hydrogen atom, a methylamino group, and a dimethylamino group; or
b) Rb is a hydrogen atom;
Rc is chosen from a hydrogen atom, chlorine, bromine, and a ($C_3$ to $C_5$) alkenyl group; and
Rd is $-Nme-R'''$, wherein R''' is chosen from:
(1) an alkyl, a ($C_2$ to $C_4$) hydroxyalkyl, or a ($C_2$ to $C_8$) alkenyl which is unsubstituted or substituted with:
(i) a phenyl, (ii) a ($C_3$ to $C_6$) cycloalkylmethyl, (iii) an unsubstituted benzyl, (iv) a substituted benzyl which is substituted with one or more halogen atoms, hydroxyl groups, alkyl groups, alkyloxy groups, alkylthio groups, alkylsulfinyl groups, alkylsulfonyl groups, amino groups, alkylamino groups, dialkylamino groups, (v) a heterocyclylmethyl or heterocyclylethyl in which the heterocyclyl portion is saturated or unsaturated and contains 5 to 6 members and at least one heteroatom chosen from sulfur, oxygen, and nitrogen, wherein the heterocyclyl portion is unsubstituted or substituted with:
an alkyl group, a ($C_2$ to $C_8$) alkenyl group, a ($C_3$ to $C_6$) cycloalkyl group, a ($C_4$ to $C_6$) saturated or unsaturated heterocyclyl group, a phenyl group, a benzyl group, or a phenyl group which is substituted with a group chosen from a hydrogen atom, a ($C_1$ to $C_8$) alkyl group, a ($C_2$ to $C_8$) alkenyl group, a ($C_3$ to $C_8$) cycloalkyl group, a ($C_3$ to $C_8$) saturated or unsaturated heterocyclyl group, an unsubstituted phenyl group, a substituted phenyl group substituted with one or more halogen atoms, hydroxyl groups, alkyl groups, alkyloxy groups, alkylthio groups, alkylsulfinyl groups, alkylsulfonyl groups, amino groups, alkylamino groups, or dialkylamino groups, and a group NR'R";
(2) a cyanomethyl group or a $-CH_2CORe$ group,
wherein Re is chosen from:
(a) $-OR'e$, wherein R'e is chosen from: (i) a hydrogen atom, (ii) ($C_1$ to $C_6$) alkyl, (iii) ($C_2$ to $C_6$) alkenyl, (iv) benzyl and (v) heterocyclylmethyl in which the heterocyclyl portion contains 5 to 6 members and 1 or 2 heteroatoms chosen from sulfur, oxygen, and nitrogen; and (b) an alkylamino group, an alkylmethylamino group, a heterocyclylamino group, and a heterocyclylmethylamino group in which the heterocyclyl portion is saturated and contains from 5 to 6 members and one or two heteroatoms chosen from sulfur, oxygen, and nitrogen which may themselves be unsubstituted or substituted with an alkyl, benzyl or alkyloxycarbonyl group;

c) Rb is a hydrogen atom;

Rd is chosen from —NHCH$_3$ and —N(CH$_3$)$_2$, wherein when Rd is —NHCH$_3$, Rc is chosen from chlorine and bromine, and wherein when Rd is —N(CH$_3$)$_2$, then Rc is chosen from chlorine, bromine, and an alkenyl group containing from 3 to 5 carbon atoms;

d) Rb and Rd are each hydrogen atom; and

Rc is chosen from a halogen atom, an alkylamino, a dialkylamino, an alkyloxy, a trifluoromethoxy, a thioalkyl, a ($C_1$ to $C_6$) alkyl, and a trihalomethyl group;

e) Rb and Rc are each hydrogen atom, and

Rd is chosen from a halogen atom, an ethylamino, a diethylamino, a methylethylamino, an alkyloxy, a trifluoromethoxy, an alkylthio, an alkylsulfinyl, an alkylsulfonyl, a ($C_1$ to $C_6$) alkyl, a phenyl group, and a trihalomethyl group;

f) Rb is a hydrogen atom;

Rc is chosen from a halogen atom, an alkylamino, a dialkylamino, an alkyloxy, a trifluoromethoxy, a thioalkyl, and a ($C_1$ to $C_3$) alkyl group; and Rd is chosen from a halogen atom, an amino, an alkylamino, a dialkylamino, an alkyloxy, a trifluoromethoxy, a thioalkyl, a ($C_1$ to $C_6$) alkyl, and a trihalomethyl group; and g) Rc is a hydrogen atom; and Rb and Rd are each a methyl group.

5. The pharmaceutical composition according to claim 3, wherein the dialkylamino of (1)(A)(iv)(c) is substituted with mercapto or dialkylamino.

6. A pharmaceutical composition according to claim 3, wherein said 4-imidazolyl, said 5-imidazolyl, said unsubstituted or substituted piperazine rings, said morpholino, said thiomorpholino, said piperidino, said 1-pyrrolidinyl, said 2-piperidyl, said 3-piperidyl, said 4-piperidyl, said 2-pyrrolidinyl, or said 3-pyrrolidinyl may be substituted with alkyl.

7. A pharmaceutical composition according to claim 4, wherein the 3-to 8-membered saturated or unsaturated heterocyclyl group of $R_1$ further comprises another heteroatom chosen from oxygen, sulfur, and nitrogen.

8. A pharmaceutical composition according to claim 4, wherein the 3- to 8-membered saturated or unsaturated heterocyclyl group is substituted with at least one group chosen from an alkyl, a ($C_2$ to $C_8$) alkenyl group, a ($C_3$ to $C_6$) cycloalkyl group, a ($C_4$ to $C_6$) saturated or unsaturated heterocyclyl group, a benzyl group, a phenyl group, and a phenyl group which is substituted with one or more halogen atoms, hydroxyl groups, alkyl groups, alkyloxy groups, alkylthio groups, alkylsulfinyl groups, alkylsulfonyl groups, amino groups, alkylamino groups, or dialkylamino groups.

9. A pharmaceutical composition according to claim 1, wherein the group B streptogramin compound is a semisynthetic compound of formula (B) or a salt thereof:

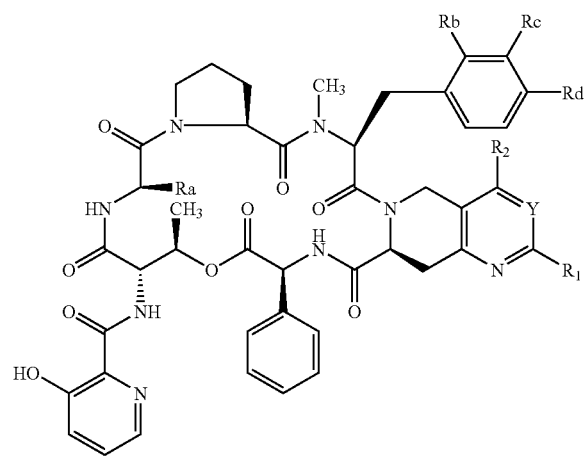

wherein,

Y is nitrogen;

$R_1$ is chosen from:

(1) a hydrogen atom, (2) a ($C_1$ to $C_8$) alkyl group, (3) a ($C_2$ to $C_8$) alkenyl group, (4) a ($C_3$ to $C_8$) cycloalkyl group, (5) a ($C_3$ to $C_8$) saturated or unsaturated heterocyclyl group, (6) an NH group, (7) an unsubstituted phenyl group, (8) a substituted phenyl group which is substituted with one or more halogen atoms, hydroxyl groups, alkyl groups, alkyloxy groups, alkylthio groups, alkylsulfinyl groups, alkylsulfonyl groups, amino groups, alkylamino groups, or dialkylamino groups, (9) a group NR'R", wherein R' and R", which may be identical or different, are chosen from: (i) a hydrogen atom, (ii) a ($C_1$ to $C_3$) alkyl group, (iii) a halomethyl, (iv) a hydroxymethyl, (v) an alkyloxymethyl, (vi) an alkylthio-methyl in which the alkyl portion is optionally substituted with NR'R", (vii) an alkylsulfinylmethyl, (viii) an alkylsulfonylmethyl, (ix) an acyloxymethyl, (x) a benzoyloxy-methyl, (xi) a cyclopropylaminomethyl, (xii) a —(CH$_2$)$_n$NR'R" group, wherein n is an integer from 1 to 4, and (xiii) a 3- to 8-membered heterocycle formed with the nitrogen atom to which they are attached, and

(10) —XR°, wherein

X is an oxygen atom, a sulfur atom, a sulfinyl group, or a sulfonyl group, and

R° is chosen from a ($C_1$ to $C_8$) alkyl group, a ($C_3$ to $C_6$) cycloalkyl group, a ($C_3$ to $C_8$) saturated or unsaturated heterocyclyl group, and a ($C_3$ to $C_8$) heterocyclylmethyl group in which the heterocyclyl portion is attached to the methyl group by a carbon atom, a phenyl group, a phenyl group which is substituted with one or more halogen atoms, hydroxyl groups, alkyl groups, alkyloxy groups, alkylthio groups, alkylsulfinyl groups, alkylsulfonyl groups, amino groups, alkylamino groups, dialkylamino groups, or a —$(CH_2)_n$NR'R" group, wherein n is an integer ranging from 2 to 4, and wherein if X is NH, R° may also be a hydrogen atom; and if $R_3$ is a hydrogen atom, $R_1$ may also be chosen from a formyl, a carboxyl, an alkyloxycarbonyl, and a —CO—NR'R" group, wherein R' and R" are defined as above;

$R_2$ is chosen from a hydrogen atom and a ($C_1$ to $C_3$) alkyl group;

$R_3$ is chosen from a hydrogen atom, an alkyl group, a carboxyl group, an alkyloxycarbonyl group, and a —CO—NR'R", wherein R' and R" are defined as above;

Ra is chosen from a methyl group and an ethyl group; and Rb, Rc and Rd are defined below:

a) Rb and Rc are each hydrogen atom; and
  Rd is chosen from a hydrogen atom, a methylamino group, and a dimethylamino group; or
b) Rb is a hydrogen atom;
  Rc is chosen from a hydrogen atom, chlorine, bromine, and a ($C_3$ to $C_5$) alkenyl group; and
  Rd is —Nme-R'" wherein R'" is chosen from:
    (1) an alkyl, a ($C_2$ to $C_4$) hydroxyalkyl, or a ($C_2$ to $C_8$) alkenyl which is unsubstituted or substituted with:
      (i) a phenyl, (ii) a ($C_3$ to $C_6$) cycloalkylmethyl, (iii) an unsubstituted benzyl, (iv) a substituted benzyl which is substituted with one or more halogen atoms, hydroxyl groups, alkyl groups, alkyloxy groups, alkylthio groups, alkylsulfinyl groups, alkylsulfonyl groups, amino groups, alkylamino groups, or dialkylamino groups, (v) heterocyclylmethyl or heterocyclylethyl in which the heterocyclyl portion is saturated or unsaturated and contains from 5 to 6 members and at least one heteroatom chosen from sulfur, oxygen or nitrogen, wherein the heterocyclyl portion is unsubstituted or substituted with:
        an alkyl group, a ($C_2$ to $C_8$) alkenyl group, a ($C_3$ to $C_6$) cycloalkyl group, a ($C_4$ to $C_6$) saturated or unsaturated heterocyclyl group, a phenyl group, a benzyl group, and a phenyl group which is substituted with a group chosen from a hydrogen atom, a ($C_1$ to $C_8$) alkyl group, a ($C_2$ to $C_8$) alkenyl group, a ($C_3$ to $C_8$) cycloalkyl group, a ($C_3$ to $C_8$) saturated or unsaturated heterocyclyl group, an unsubstituted phenyl group, a substituted phenyl group substituted with one or more halogen atoms, hydroxyl groups, alkyl groups, alkyloxy groups, alkylthio groups, alkylsulfinyl groups, alkylsulfonyl groups, amino groups, alkylamino groups, or dialkylamino groups, and a group NR'R"; or
    (2) a cyanomethyl group or a —$CH_2CO$Re group, wherein Re is chosen from:
      (a) —OR'e, wherein R'e is chosen from: (i) a hydrogen atom, (ii) ($C_1$ to $C_6$) alkyl, (iii) ($C_2$ to $C_6$) alkenyl, (iv) benzyl and (v) heterocyclylmethyl in which the heterocyclyl portion contains 5 to 6 members and 1 or 2 heteroatoms chosen from sulfur, oxygen, and nitrogen; and
      (b) an alkylamino group, an alkylmethylamino group, a heterocyclylamino group, and a heterocyclylmethylamino group in which the heterocyclyl portion is saturated and contains from 5 to 6 members and one or two heteroatoms chosen from sulfur, oxygen, and nitrogen which themselves are unsubstituted or substituted with an alkyl, benzyl or alkyloxycarbonyl group; or c) Rb is a hydrogen atom;
  Rd is chosen from —$NHCH_3$ and —$N(CH_3)_2$, wherein when Rd is —$NHCH_3$, Rc is chosen from chlorine and bromine, and wherein when Rd is —$N(CH_3)_2$, then Rc is chosen from chlorine, bromine, and an alkenyl group containing 3 to 5 carbon atoms; or d) Rb and Rd are each hydrogen atom; and
  Rc is chosen from a halogen atom, an alkylamino, a dialkylamino, an alkyloxy, a trifluoromethoxy, a thioalkyl, a ($C_1$ to $C_6$) alkyl, and a trihalomethyl group; or e) Rb and Rc are each hydrogen atom, and
  Rd is chosen from a halogen atom, an ethylamino, a diethylamino, a methylethylamino, an alkyloxy, a trifluoromethoxy, an alkylthio, an alkylsulfinyl, an alkylsulfonyl, a ($C_1$ to $C_6$) alkyl, a phenyl group, and a trihalomethyl group; or f) Rb is a hydrogen atom;
  Rc is chosen from a halogen atom, an alkylamino, a dialkylamino, an alkyloxy, a trifluoromethoxy, a thioalkyl, and a ($C_1$ to $C_3$) alkyl group; and
  Rd is chosen from a halogen atom, an amino, an alkylamino, a dialkylamino, an alkyloxy, a trifluoromethoxy, a thioalkyl, a ($C_1$ to $C_6$) alkyl, and a trihalomethyl group; or g) Rc is a hydrogen atom; and
  Rb and Rd are each a methyl group.

10. A pharmaceutical composition according to claim 9, wherein the 3- to 8-membered saturated or unsaturated heterocyclyl group of $R_1$ further comprises another heteroatom chosen from oxygen, sulfur, and nitrogen.

11. A pharmaceutical composition according to claim 9, wherein the 3- to 8-membered saturated or unsaturated heterocyclyl group is substituted with at least one group chosen from an alkyl, a ($C_2$ to $C_8$) alkenyl group, a ($C_3$ to $C_6$) cycloalkyl group, a ($C_4$ to $C_6$) saturated or unsaturated heterocyclyl group, a benzyl group, a phenyl group, and a phenyl group which is substituted with at least one halogen atom, hydroxyl, alkyl, alkyloxy, alkylthio, alkylsulfinyl, alkylsulfonyl, amino, alkylamino, or dialkylamino group.

* * * * *

UNITED STATES PATENT AND TRADEMARK OFFICE
CERTIFICATE OF CORRECTION

PATENT NO. : 7,166,594 B2
APPLICATION NO. : 10/310773
DATED : January 23, 2007
INVENTOR(S) : Daniel Achard et al.

It is certified that error appears in the above-identified patent and that said Letters Patent is hereby corrected as shown below:

In claim 1, column 79, line 51, "₃ is" should read --$R_3$ is--.

In claim 3, column 80, line 58, "4-quinuclidinyithiomethyl" should read --4-quinuclidinylthiomethyl--.

In claim 4, column 82, line 9, "R' and R' " should read --R' and R"--.

In claim 7, column 83, line 51, "3-to" should read --3- to--.

Signed and Sealed this

Tenth Day of July, 2007

JON W. DUDAS
*Director of the United States Patent and Trademark Office*